US006951693B2

(12) United States Patent
Hosokawa et al.

(10) Patent No.: US 6,951,693 B2
(45) Date of Patent: Oct. 4, 2005

(54) ORGANIC ELECTROLUMINESCENCE DEVICE

(75) Inventors: Chishio Hosokawa, Chiba-ken (JP); Masakazu Funahashi, Chiba-ken (JP); Hisayuki Kawamura, Chiba-ken (JP); Hiromasa Arai, Chiba-ken (JP); Hidetoshi Koga, Chiba-ken (JP); Hidetsugu Ikeda, Chiba-ken (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 10/179,179

(22) Filed: Jun. 26, 2002

(65) Prior Publication Data

US 2003/0072966 A1 Apr. 17, 2003

Related U.S. Application Data

(62) Division of application No. 09/623,057, filed as application No. PCT/JP99/07390 on Dec. 28, 1999, now Pat. No. 6,743,948.

(30) Foreign Application Priority Data

| Dec. 28, 1998 | (JP) | 10-373921 |
| May 20, 1999 | (JP) | 11-140103 |
| Aug. 5, 1999 | (JP) | 11-223056 |
| Aug. 20, 1999 | (JP) | 11-234652 |
| Dec. 7, 1999 | (JP) | 11-347848 |

(51) Int. Cl.$^7$ .................. H05B 33/12; C09K 11/06; C07C 211/61

(52) U.S. Cl. ............... 428/690; 428/917; 313/504; 313/506; 252/301.16; 564/305; 564/426; 564/427; 564/431

(58) Field of Search ............... 428/690, 704, 428/917; 313/504, 506; 252/301.16; 564/305, 403, 404, 405, 426, 431, 427

(56) References Cited

U.S. PATENT DOCUMENTS

| 5,759,444 | A |   | 6/1998 | Enokida et al. | 252/301.16 |
| 5,837,166 | A |   | 11/1998 | Kawamura et al. | 252/583 |
| 6,074,734 | A |   | 6/2000 | Kawamura et al. | 428/220 |
| 6,203,933 | B1 |   | 3/2001 | Nakaya et al. | 428/690 |
| 6,280,859 | B1 | * | 8/2001 | Onikubo et al. | 428/690 |

FOREIGN PATENT DOCUMENTS

| EP | 0 802 173 | 10/1997 |
| JP | 8-311442 | 11/1996 |
| JP | 9-268284 | 10/1997 |
| JP | 9-304952 | 11/1997 |
| JP | 10-88120 | 7/1998 |
| JP | 10-237438 | 9/1998 |
| JP | 10-251633 | 9/1998 |
| JP | 11-135261 | 5/1999 |

OTHER PUBLICATIONS

Full–length English language translation of JP 9–268284 (Oct. 14, 1997).*

* cited by examiner

Primary Examiner—Marie Yamnitzky
(74) Attorney, Agent, or Firm—Oblon, Spivak, McClelland, Maier & Neustadt, P.C.

(57) ABSTRACT

Materials for organic electroluminescence devices represented by following general formula [1]:

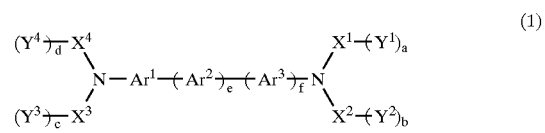

(1)

wherein A represents a substituted or unsubstituted arylene group having 22 to 60 carbon atoms, $X^1$ to $X^4$ each independently represent a substituted or unsubstituted arylene group having 6 to 30 carbon atoms, $X^1$ and $X^2$ may be bonded to each other, $X^3$ and $X^4$ may be bonded to each other, $Y^1$ to $Y^4$ each independently represent an organic group represented by general formula [2], a to d each represent an integer of 0 to 2 and, when the arylene group represented by A has 26 or less carbon atoms, a+b+c+d>0 and the arylene group does not contain two or more anthracene nucleus; general formula [2] being:

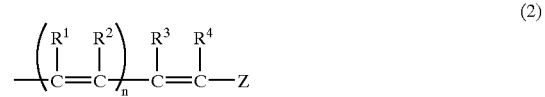

(2)

wherein $R^1$ to $R^4$ each independently represent hydrogen atom, a substituted or unsubstituted alkyl group having 1 to 20 carbon atoms, a substituted or unsubstituted aryl group having 6 to 20 carbon atoms, cyano group or form a triple bond by a linkage of $R^1$ and $R^2$ or $R^3$ and $R^4$, Z represents a substituted or unsubstituted aryl group having 6 to 20 carbon atoms and n represents 0 or 1.

9 Claims, 3 Drawing Sheets

ORGANIC ELECTROLUMINESCENCE DEVICE

This application is a Division of application Ser. No. 09/623,057, filed on Aug. 25, 2000, now U.S. Pat. No. 6,743,948, which was a 371 of International Application No. PCT/JP99/07390, filed Dec. 28, 1999.

TECHNICAL FIELD

The present invention relates to materials for organic electroluminescence devices which are used as a light source such as a planar light emitting member of televisions and a back light of displays, exhibit high efficiency of light emission and have excellent heat resistance and a long life, organic electroluminescence devices using the materials, novel compounds and processes for producing materials for electroluminescence devices.

BACKGROUND ART

Electroluminescence (EL) devices using organic compounds are expected to be used for inexpensive full color display devices of the solid light emission type which can display a large area and development thereof has been actively conducted. In general, an EL device is constituted with a light emitting layer and a pair of electrodes faced to each other at both sides of the light emitting layer. When a voltage is applied between the electrodes, electrons are injected at the side of the cathode and holes are injected at the side of the anode. The electrons are combined with the holes in the light emitting layer and an excited state is formed. When the excited state returns to the normal state, the energy is emitted as light.

Heretofore, organic EL devices require higher driving voltages and show inferior luminance of emitted light and inferior efficiencies of light emission in comparison with inorganic devices. Moreover, properties of organic EL devices deteriorate very rapidly. Therefore, heretofore, organic EL devices have not been used practically. Although the properties of organic EL devices have been improved, organic EL devices exhibiting a sufficient efficiency of light emission and having sufficient heat resistance and life have not been obtained. For example, a phenylanthracene derivative which can be used for EL devices is disclosed in Japanese Patent Application Laid-Open No. Heisei 8(1996)-12600. However, an organic EL device using this compound exhibited an efficiency of light emission as low as about 2 to 4 cd/A and improvement in the efficiency is desired. In Japanese Patent Application Laid-Open No. Heisei 8(1996)-199162, an EL device having a light emitting layer containing a fluorescent dopant of a derivative of an amine or a diamine is disclosed. However, this EL device has a life as short as 700 hours at an initial luminance of emitted light of 300 cd/m$^2$ although the efficiency of light emission is 4 to 6 dc/A and improvement in the life is desired. In Japanese Patent Application Laid-Open No. Heisei 9(1997)-268284, a material for EL devices having phenylanthracene group is disclosed. This material exhibits a marked decrease in the luminance of emitted light when the material is used at a high temperature for a long time and heat resistance is insufficient. Moreover, these devices do not emit light in the region of orange to red color. Since emission of red color is indispensable for the full color display by an EL device, a device emitting light in the region of orange to red color is desired. When these materials are used as the host material and other compounds are used as the doping material, a long life cannot be obtained. It is necessary for practical use that an initial luminance of emitted light of 10,000 d/m$^2$ or greater be exhibited. However, this value has not been achieved. In Japanese Patent Application Laid-Open No. Heisei 11(1999)-152253, an example is disclosed in which a material for organic EL devices having a binaphthalene structure is added to a light emitting layer having the property to transfer electrons such as a layer of an aluminum complex or the like. However, in this example, the aluminum complex or the like emits light and the material for organic EL devices does not function as the light emitting center since the energy gap of the light emitting layer of the aluminum complex or the like is smaller than the energy gap of the material for organic EL devices.

Synthesis of arylamines used as a material for organic EL devices has been conducted by the Ullmann reaction using an amine and an iodobenzene. It is described, for example, in Chem. Lett., pp. 1145 to 1148, 1989; the specification of U.S. Pat. No. 4,764,625; and Japanese Patent Application Laid-Open No. Heisei 8(1996)-48974 that a triarylamine is produced by the reaction of a corresponding iodobenzene and a diarylamine in an inert hydrocarbon solvent such as decaline at 150° C. or higher in the presence of one equivalent or more of copper powder and a base such as potassium hydroxide as the typical example.

However, the process using the Ullmann reaction has drawbacks in that an expensive iodide must be used as the reacting agent, that the reaction cannot be applied to many types of compounds, that the yield of the reaction is not sufficient, that the reaction requires a temperature as high as 150° C. and a long time and that waste liquid containing a great amount of copper is formed since copper powder is used in a great amount and environmental problems arise.

DISCLOSURE OF THE INVENTION

The present invention has been made to overcome the above problems and has an object to provide a material for organic electroluminescence devices, an organic electroluminescence device and a novel compound which exhibit high efficiency of light emission and have a long life and excellent heat resistance and a process for producing the material for organic electroluminescence devices.

As the result of extensive studies by the present inventors to develop the material for organic EL devices having the advantageous properties described above and an organic EL device using the material, it was found that the object can be achieved by using the compounds represented by general formulae [1] and [3] to [10] which are shown below. The present invention has been completed based on this knowledge.

It was also found by the present inventors that the above object can be achieved by using the compounds represented by general formulae [11] and [11'] as the doping material or the light emitting center.

It was further found by the present inventors that a tertiary arylamine which is a material for organic EL devices can be synthesized with a high activity by the reaction of an amine and an aryl halide in the presence of a catalyst comprising a phosphine compound and a palladium compound and a base. The present invention has been completed based on the above knowledge.

The material for organic electroluminescence devices (referred to as the material for organic EL devices) of the present invention is a compound represented by following general formula [1]:

General formula [1]

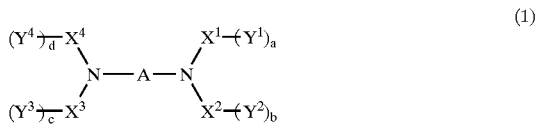
(1)

wherein A represents a substituted or unsubstituted arylene group having 22 to 60 carbon atoms, $X^1$ to $X^4$ each independently represent a substituted or unsubstituted arylene group having 6 to 30 carbon atoms, $X^1$ and $X^2$ may be bonded to each other, $X^3$ and $X^4$ may be bonded to each other, $Y^1$ to $Y^4$ each independently represent an organic group represented by general formula [2], a to d each represent an integer of 0 to 2 and, when the arylene group represented by A has 26 or less carbon atoms, a+b+c+d>0 and the arylene group does not contain two or more anthracene nuclei; general formula [2] being:

General formula [2]

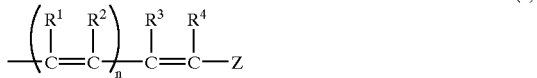
(2)

wherein $R^1$ to $R^4$ each independently represent hydrogen atom, a substituted or unsubstituted alkyl group having 1 to 20 carbon atoms, a substituted or unsubstituted aryl group having 6 to 20 carbon atoms or cyano group or form a triple bond by a linkage of $R^1$ and $R^2$ or $R^3$ and $R^4$, Z represents a substituted or unsubstituted aryl group having 6 to 20 carbon atoms and n represents 0 or 1.

The material for organic electroluminescence devices of the present invention may also be a compound represented by following general formula [3]:

General formula [3]

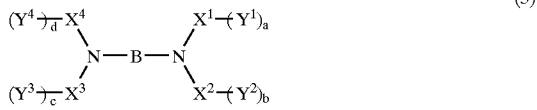
(3)

wherein B represents a substituted or unsubstituted arylene group having 6 to 60 carbon atoms, $X^1$ to $X^4$ each independently represent a substituted or unsubstituted arylene group having 6 to 30 carbon atoms, $X^1$ and $X^2$ may be bonded to each other, $X^3$ and $X^4$ may be bonded to each other, $Y^1$ to $Y^4$ each independently represent an organic group represented by general formula [2] described above, a to d each represent an integer of 0 to 2 and at least one of groups represented by B, $X^1$, $X^2$, $X^3$ and $X^4$ has a chrysene nucleus.

It is preferable that general formula [3] means following general formula [4], general formula [5] or general formula [6].

General formula [4]:

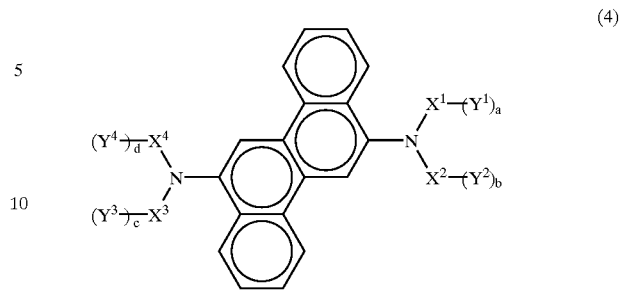
(4)

wherein $X^1$ to $X^4$, $Y^1$ to $Y^4$ and a to d are each independently the same as those in general formula [3].

General formula [5]:

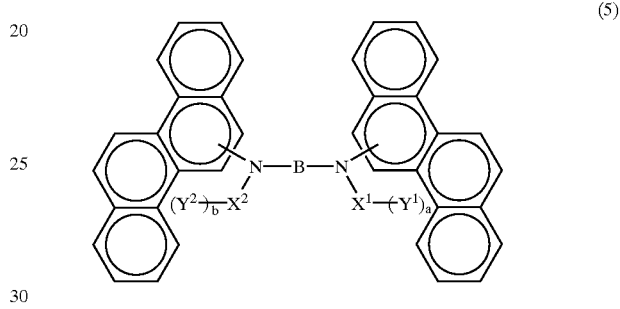
(5)

wherein B, $X^1$, $X^2$, $Y^1$, $Y^2$, a and b are each independently the same as those in general formula [3].

General formula [6]:

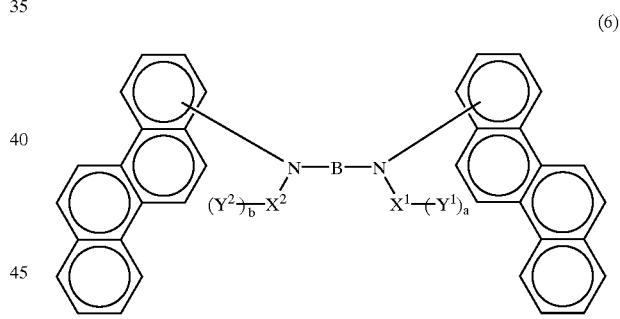
(6)

wherein B, $X^1$, $X^2$, $Y^1$, $Y^2$, a and b are each independently the same as those in general formula [3].

The material for organic electroluminescence devices of the present invention may also be a compound represented by following general formula [7]:

General formula [7]

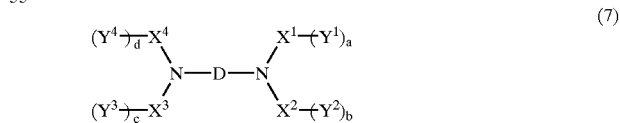
(7)

wherein D represents a divalent group having a tetracene nucleus or a pentacene nucleus, $X^1$ to $X^4$ each independently represent a substituted or unsubstituted arylene group containing 6 to 30 carbon atoms, $X^1$ and $X^2$ may be bonded to each other, $X^3$ and $X^4$ may be bonded to each other, $Y^1$ to $Y^4$ each independently represent an organic group represented by general formula [2] described above and a to d each represent an integer of 0 to 2.

It is preferable that general formula [7] means following general formula [8]:

General formula [8]

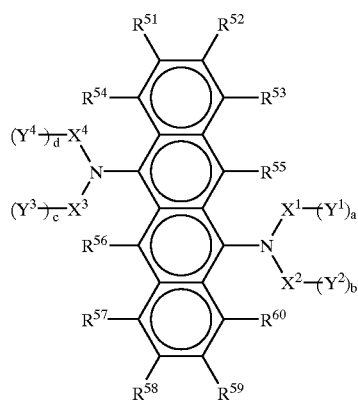

(8)

wherein $X^1$ to $X^4$, $Y^1$ to $Y^4$ and a to d are each independently the same as those in general formula [7], $R^{51}$ to $R^{60}$ each independently represent hydrogen atom, a substituted or unsubstituted alkyl group having 1 to 20 carbon atoms, a substituted or unsubstituted alkoxy group having 1 to 20 carbon atoms, a substituted or unsubstituted aryl group having 6 to 20 carbon atoms or cyano group and adjacent groups among the groups represented by $R^{51}$ to $R^{60}$ may be bonded to each other to form a saturated or unsaturated and substituted or unsubstituted carbon ring.

The material for organic electroluminescence devices of the present invention may also be a compound represented by following general formula [9]:

General formula [9]

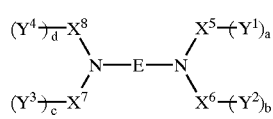

(9)

wherein E represents a divalent group comprising an anthracene nucleus which is substituted with aryl groups or unsubstituted, $X^5$ to $X^8$ each independently represent a substituted or unsubstituted arylene group having 6 to 20 carbon atoms, $X^5$ and $X^6$ may be bonded to each other, $X^7$ and $X^8$ may be bonded to each other, $Y^1$ to $Y^4$ each independently represent an organic group represented by general formula [2], a to d each represent an integer of 0 to 2, and when the group represented by E is an unsubstituted group:

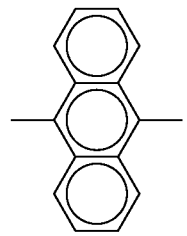

at least two of $X^5$ to $X^8$ contains a substituted or unsubstituted group:

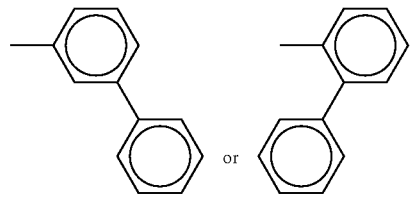

The material for organic electroluminescence devices of the present invention may also be a compound represented by following general formula [10]:

General formula [10]

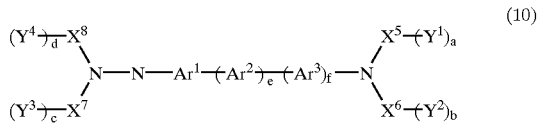

(10)

wherein $Ar^1$ and $Ar^3$ each independently represents a divalent group selected from a group consisting of substituted and unsubstituted phenylene groups, substituted and unsubstituted 1,3-naphthalene groups, substituted and unsubstituted 1,8-naphthalene groups, substituted and unsubstituted fluorene groups and substituted and unsubstituted biphenyl groups, $Ar^2$ represents a divalent group selected from a group consisting of substituted and unsubstituted anthracene nuclei, substituted and unsubstituted pyrene nuclei, substituted and unsubstituted phenanthrene nuclei, substituted and unsubstituted chrysene nuclei, substituted and unsubstituted pentacene nuclei, substituted and unsubstituted naphthacene nuclei and substituted and unsubstituted fluorene nuclei, $X^5$ to $X^8$ each independently represent a substituted or unsubstituted arylene group having 6 to 20 carbon atoms, $X^5$ and $X^6$ may be bonded to each other, $X^7$ and $X^8$ may be bonded to each other, $Y^1$ to $Y^4$ each independently represent an organic group represented by general formula [2] described above, a to d each represent an integer of 0 to 2, a+b+c+d≦2, e represents 0 or 1, f represents 1 or 2 and, when $Ar^2$ represents an anthracene nucleus, a case in which a=b=c=d and $Ar^1$ and $Ar^3$ both represent p-phenylene group is excluded.

The material for organic electroluminescence devices of the present invention may also be a compound represented by following general formula [11]:

General formula [11]

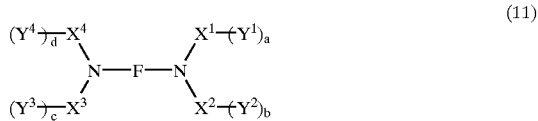

(11)

wherein F represents a substituted or unsubstituted arylene group having 6 to 21 carbon atoms, $X^1$ to $X^4$ each independently represent a substituted or unsubstituted arylene group having 6 to 30 carbon atoms, $X^1$ and $X^2$ may be bonded to each other, $X^3$ and $X^4$ may be bonded to each other, $Y^1$ to $Y^4$ each independently represent an organic group represented by general formula [2] described above, a to d each represent an integer of 0 to 2, and a+b+c+d>0.

It is preferable that the group represented by F in general formula [11] is a group represented by following general formula [12], general formula [13] or general formula [14]:

General formula [12]

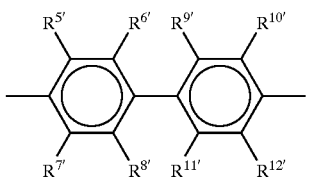

General formula [13]

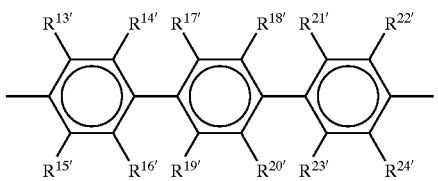

wherein $R^{5'}$ to $R^{24'}$ each independently represent hydrogen atom, a substituted or unsubstituted alkyl group having 1 to 20 carbon atoms, a substituted or unsubstituted aryl group having 6 to 20 carbon atoms or cyano group and adjacent groups among the groups represented by $R^{5'}$ to $R^{24'}$ may be bonded to each other to form a saturated or unsaturated carbon ring;

General formula [14]

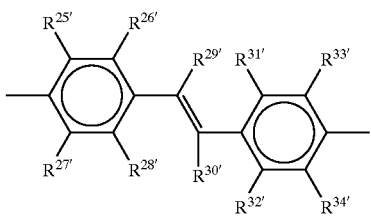

wherein $R^{25'}$ to $R^{34'}$ each independently represent hydrogen atom, a substituted or unsubstituted alkyl group having 1 to 20 carbon atoms, a substituted or unsubstituted aryl group having 6 to 20 carbon atoms or cyano group and adjacent groups among the groups represented by $R^{5'}$ to $R^{24'}$ may be bonded to each other to form a saturated or unsaturated carbon ring.

The material for organic EL devices of the present invention which is represented by any of general formulae [1], [3] to [11] and [11'] can be used also as the light emitting material for organic electroluminescence devices.

The organic electroluminescence (EL) device of the present invention comprises a light emitting layer or a plurality of thin films of organic compounds comprising a light emitting layer disposed between a pair of electrodes, wherein at least one of the thin films of organic compounds is a layer comprising a materials for organic EL devices represented by any of general formulae [1], [3] to [11] and [11'].

It is preferable that, in the above organic EL device, a layer comprising the material for organic EL devices represented by any of general formulae [1], [3] to [11] and [11'] as at least one material selected from a group consisting of a hole injecting material, a hole transporting material and a doping material is disposed between the pair of electrodes.

It is preferable that, in the above organic EL device, the light emitting layer comprises 0.1 to 20% by weight of a material for organic EL devices represented by any of general formulae [1], [3] to [11] and [11'].

It is preferable that, in the above organic electroluminescence device, one or more materials selected from a group consisting of a hole injecting material, a hole transporting material and a doping material each independently comprise 0.1 to 20% by weight of the material for organic EL devices represented by any of general formulae [1], [3] to [11] and [11'].

It is preferable that, in the above organic EL device, the light emitting layer is a layer comprising a stilbene derivative and a material for organic EL devices represented by any of general formulae [1], [3] to [11] and [11'].

In the above organic EL device, a layer comprising an aromatic tertiary amine derivative and/or a phthalocyanine derivative is disposed between a light emitting layer and an anode.

It is preferable that, in the above organic EL device, the energy gap of the material for organic electroluminescence devices represented by general formula [11] is smaller than the energy gap of a host material by 0.07 eV or greater.

The novel compound of the present invention is represented by following general formula [11']:

General formula [11']

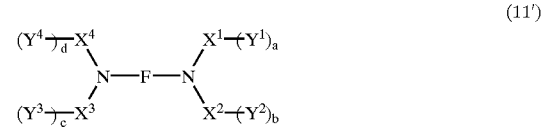

wherein F represents a group represented by general formula [14], $X^1$ to $X^4$ each independently represent a substituted or unsubstituted arylene group having 6 to 30 carbon atoms, $X^1$ and $X^2$ may be bonded to each other, $X^3$ and $X^4$ may be bonded to each other, $Y^1$ to $Y^4$ each independently represent an organic group represented by general formula [2] described above, a to d represent each an integer of 0 to 2, and a+b+c+d>0; general formula [14] being:

General formula [14]

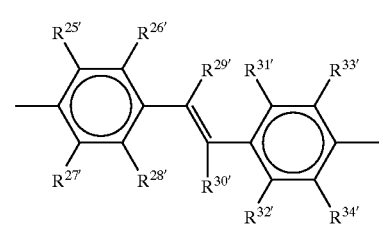

wherein $R^{25'}$ to $R^{34'}$ each independently represent hydrogen atom, a substituted or unsubstituted alkyl group having 1 to 20 carbon atoms, a substituted or unsubstituted aryl group having 6 to 20 carbon atoms or cyano group and adjacent groups among the groups represented by $R^{5'}$ to $R^{24'}$ may be bonded to each other to form a saturated or unsaturated carbon ring.

The process for producing a material for organic EL devices of the present invention comprises reacting, in a presence of a catalyst comprising a phosphine compound and a palladium compound and a base, a primary amine or a secondary amine represented by following general formula [15]:

$$R(NR'H)_k \qquad [15]$$

wherein k represents an integer of 1 to 3; when k represents 1, R and R' represent hydrogen atom, an alkyl group or a substituted or unsubstituted aryl group; and when k represents 2 or 3, R represents an alkylene group or substituted or unsubstituted arylene group and R' represents hydrogen atom, an alkyl group or a substituted or unsubstituted aryl group, with an aryl halide represented by following general formula [16]:

   [16]

wherein Ar represents a substituted or unsubstituted aryl group, X represents F, Cl, Br or I and m represents an integer of 1 to 3, and producing a material for organic electroluminescence devices comprising an arylamine compound.

It is preferable that the arylamine described above is a compound represented by following general formula [17]:

General formula [17]

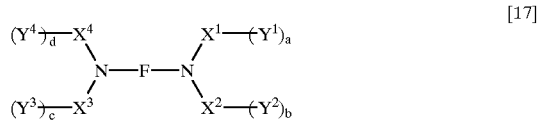   [17]

wherein F represents a substituted or unsubstituted arylene group having 6 to 60 carbon atoms, $X^1$ to $X^4$ each independently represent a substituted or unsubstituted arylene group having 6 to 30 carbon atoms, $X^1$ and $X^2$ may be bonded to each other, $X^3$ and $X^4$ may be bonded to each other, $Y^1$ to $Y^4$ each independently represent an organic group represented by general formula [2] described above, a to d each represent an integer of 0 to 2, and a+b+c+d>0.

It is preferable that the phosphine compound is a trialkylphosphine compound, a triarylphosphine compound or a diphosphine compound.

THE MOST PREFERRED EMBODIMENT TO CARRY OUT THE INVENTION

Figure 1:
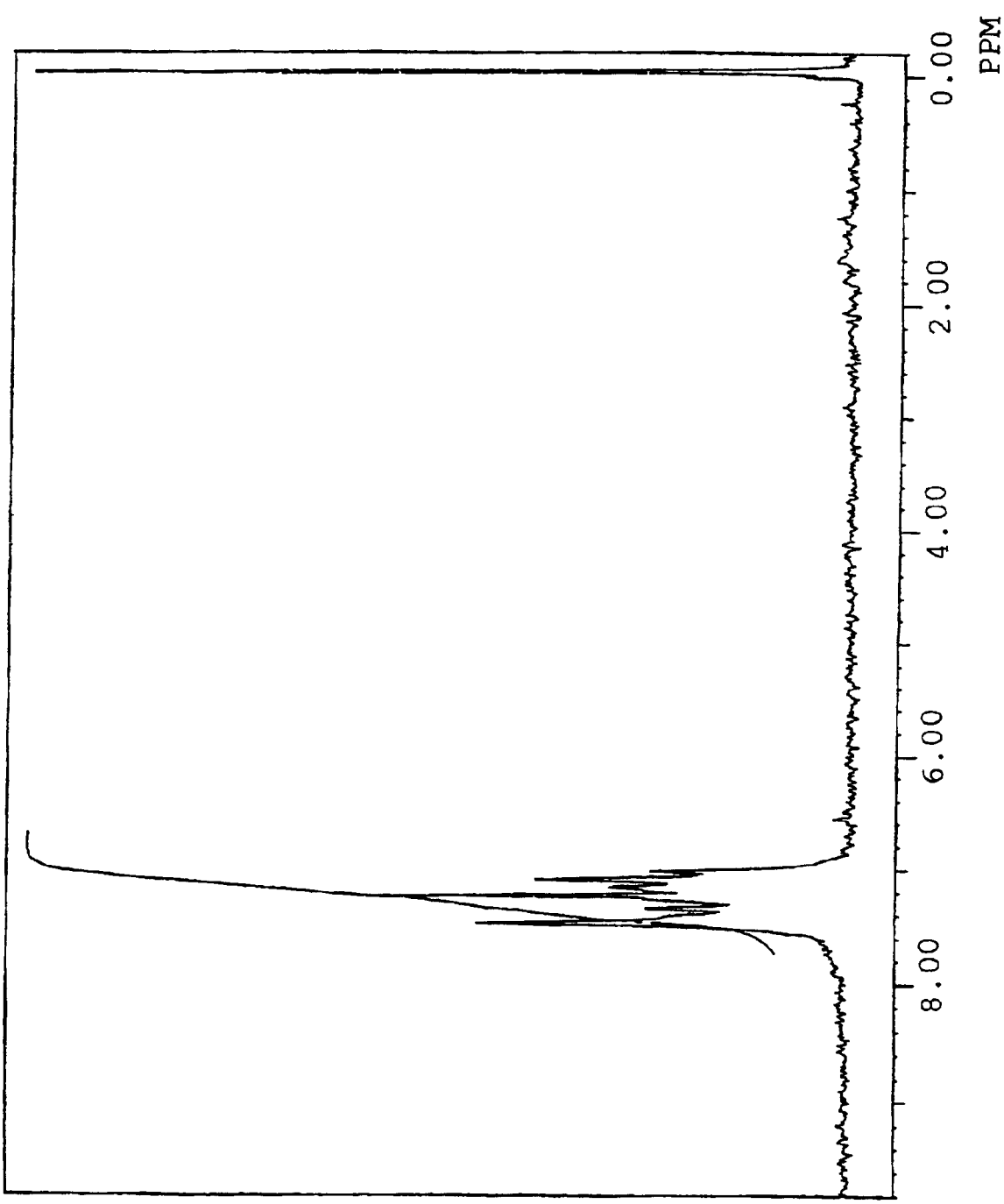
FIG. 1 shows a $^1H_{NMR}$ chart of compound a synthesized in accordance with the process of the present invention.

In general formula [1] in the present invention, A represents a substituted or unsubstituted arylene group having 22 to 60 carbon atoms. Examples of the arylene group include divalent groups formed from biphenyl, terphenyl, naphthalene, anthracene, phenanthrene, pyrene, fluorene, thiophene, coronene and fluoranthene and divalent groups formed by bonding a plurality of these groups to each other. $X^1$ to $X^4$ in general formula [1] each independently represent a substituted or unsubstituted arylene group having 6 to 30 carbon atoms. Examples of the group represented by $X^1$ to $X^4$ include monovalent or divalent groups containing skeleton structures of phenyl, biphenyl, terphenyl, naphthalene, anthrathene, phenanthrene, pyrene, fluorene, thiophene, coronene and chrysene. $X^1$ and $X^2$ may be connected to each other and $X^3$ and $X^4$ may be connected to each other.

The groups used as the substituents to the groups represented by $X^1$ to $X^4$ are each independently an alkyl group having 1 to 20 carbon atoms, an alkoxy group having 1 to 20 carbon atoms or an aryl group having 6 to 20 carbon atoms. Aryloxy groups, arylthio groups, arylalkyl groups and aryl ketone groups are excluded from the above substituent because compounds having the groups excluded above tend to decompose under heating in vapor deposition and the life of the obtained device is short.

In general formula [1], a to d each represent an integer of 0 to 2. However, when the group represented by A has 26 or less carbon atoms, a+b+c+d>0 and the group represented by A does not contain 2 or more anthracene nuclei.

In general formula [2] in the present invention, $R^1$ to $R^4$ each independently represent hydrogen atom, a substituted or unsubstituted alkyl group having 1 to 20 carbon atoms, a substituted or unsubstituted aryl group having 6 to 20 carbon atoms or cyano group. Examples of the group represented by $R^1$ to $R^4$ include substituted and unsubstituted alkyl groups such as methyl group, ethyl group, propyl group, butyl group, sec-butyl group, tert-butyl group, pentyl group, hexyl group, heptyl group, octyl group, stearyl group, 2-phenylisopropyl group, trichloromethyl group, trifluoromethyl group, benzyl group, α-phenoxybenzyl group, α,α-dimethylbenzyl group, α,α-methylphenylbenzyl group, α,α-ditrifluoromethylbenzyl group, triphenylmethyl group and α-benzyloxybenzyl group; and substituted and unsubstituted aryl groups such as phenyl group, 2-methylphenyl group, 3-methylphenyl group, 4-methylphenyl group, 4-ethylphenyl group, biphenyl group, 4-methylbiphenyl group, 4-ethylbiphenyl group, 4-cyclohexylbiphenyl group, terphenyl group, 3,5-dichlorophenyl group, naphthyl group, 5-methylnaphthyl group, anthryl group and pyrenyl group.

In general formula [2] in the present invention, Z represents a substituted or unsubstituted aryl group having 6 to 20 carbon atoms. Examples of the group represented by Z include aryl groups such as phenyl group, biphenyl group, terphenyl group, naphthyl group, anthryl group, phenanthryl group, fluorenyl group, pyrenyl group and thiophene group. The above aryl groups may have substituents. Examples of the substituent include alkyl groups and aryl groups described above as the examples of the group represented by $R^1$ to $R^4$, alkoxy groups, amino group, cyano group, hydroxyl group, carboxylic acid group, ether group and ester groups. In general formula [2], n represents 0 or 1.

As described above, since the compound represented by general formula [1] in the present invention has a diamine structure at the central portion and a styrylamine structure at end portions, the ionization energy is 5.6 eV or smaller and holes can be easily injected. The mobility of holes is $10^{-4}$ $m^2/V \cdot s$ or greater. Therefore, the compound has the excellent properties as the hole injecting material and the hole transporting material. Due to the polyphenyl structure at the center, the electron affinity is 2.5 eV or greater and electrons can be easily injected.

Moreover, since the structure represented by A has 22 or more carbon atoms, an amorphous thin film can be easily formed. The glass transition temperature is raised to 100° C. or higher and heat resistance can be improved. When two or more anthracene groups are contained in the structure represented by A, there is the possibility that the compound represented by general formula [1] decomposes under heating.

Compounds having a structure in which $X^1$ and $X^2$ or $X^3$ and $X^4$ are bonded to each other through a single bond or a carbon ring bond has elevated glass transition temperatures and show improved heat resistance.

In the compounds represented by general formulae [3] to [6] of the present invention, B represents a substituted or unsubstituted arylene group having 6 to 60 carbon atoms. Examples of the group represented by B include divalent groups formed from biphenyl, terphenyl, naphthalene, anthracene, phenanthrene, pyrene, fluorene, thiophene, coronene and fluoranthene and divalent groups formed by bonding a plurality of these groups to each other. $X^1$ to $X^4$, $Y^1$ to $Y^4$ and a to d are the same as those in general formula [1], wherein at least one of the groups represented by B, $X^1$, $X^2$, $X^3$ and $X^4$ has a chrysene nucleus.

As described above, since the compounds represented by general formulae [3] to [6] in the present invention have a diamine structure at the central portion and a styrylamine structure at end portions, the ionization energy is 5.6 eV or smaller and holes can be easily injected. The mobility of holes is $10^{-4}$ m$^2$/V·s or greater. Therefore, the compound has the excellent properties as the hole injecting material and the hole transporting material. Due to the chrysene nucleus contained in at least one of the groups represented by B, $X^1$, $X^2$, $X^3$ and $X^4$, durability and heat resistance are improved. Therefore, driving for a long time is enabled and an organic EL device which can be stored or driven at high temperatures can be obtained.

Moreover, the life of the organic EL device can be extended when the compounds represented by general formulae [3] to [6] are used as the doping material and the efficiency of light emission can be improved when the compounds are used as the material of the light emitting layer.

In the compound represented by general formula [7] of the present invention, D represents a divalent group containing a substituted or unsubstituted tetracene nucleus or pentacene nucleus. Examples of the group represented by D include divalent groups formed by connecting a plurality of at least one group selected from the group consisting of biphenyl, naphthalene, anthracene, phenanthrene, fluorene and thiophene and the tetracene nucleus or the pentacene nucleus. $X^1$ to $X^4$, $Y^1$ to $Y^4$ and a to d are the same as those in general formula [1], wherein $X^1$ and $X^2$ may be bonded to each other and $X^3$ and $X^4$ may be bonded to each other.

In the compound represented by general formula [8] of the present invention, $X^1$ to $X^4$, $Y^1$ to $Y^4$ and a to d each independently represent the same atom and groups as those described above in general formula [1]. $R^{51}$ to $R^{60}$ each independently represent hydrogen atom, a substituted or unsubstituted alkyl group having 1 to 20 carbon atoms, a substituted or unsubstituted alkoxy group having 1 to 20 carbon atoms, a substituted or unsubstituted aryl group having 6 to 20 carbon atoms or cyano group and adjacent groups among the groups represented by $R^{51}$ to $R^{60}$ may be bonded to each other to form a saturated or unsaturated and substituted or unsubstituted carbon ring.

The groups used as the substituent in general formulae [7] and [8] are each independently an alkyl group having 1 to 20 carbon atoms, an alkoxy group having 1 to 20 carbon atoms or an aryl group having 6 to 20 carbon atoms. Aryloxy groups, arylthio groups, arylalkyl groups and aryl ketone groups are excluded from the above substituent because compounds having the groups excluded above tend to decompose under heating in vapor deposition and the life of the obtained device is short.

As described above, the compound represented by general formula [7] in the present invention exhibits strong fluorescence in the region of orange to red color due to the tetracene or pentacene structure. Holes are easily injected due to the diamine structure. When this compound is contained in the light emitting layer, holes are easily trapped and recombination of electrons and holes is promoted. Therefore, a light emitting device emitting yellow color, orange color and red color in a high efficiency can be obtained.

In particular, when the compound represented by general formula [7] is used as the doping material, the obtained light emitting device has a long life and exhibits more excellent stability than that exhibited by any conventional devices.

In the compound represented by general formula [9] in the present invention, E represents a divalent group comprising an anthracene nucleus which is substituted with aryl groups or unsubstituted. $X^5$ to $X^8$ each independently represent a substituted or unsubstituted arylene group having 6 to 20 carbon atoms. Examples of the group represented by $X^5$ to $X^8$ include monovalent and divalent groups containing the skeleton structure of phenylene, biphenyl, terphenyl, naphthalene, anthracene, phenanthrene, fluorene and thiophene. $X^5$ and $X^6$ may be bonded to each other and $X^7$ and $X^8$ may be bonded to each other. $Y^1$ to $Y^4$ and a to d are the same as those in general formula [1].

However, when E represents an unsubstituted group:

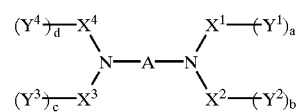

[1]

at least two of $X^5$ to $X^8$ contain a substituted or unsubstituted group:

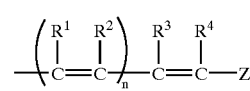

[2]

As described above, since the compound represented by general formula [9] in the present invention has a diamine structure, the ionization energy is 5.6 eV or smaller and holes can be easily injected. The mobility of holes is $10^{-4}$ m$^2$/V·s or greater. Therefore, the compound has the excellent properties as the hole injecting material and the hole transporting material. Due to the substituted or unsubstituted anthracene nucleus at the center, electrons are easily injected.

When the anthracene nucleus represented by E is unsubstituted, the glass transition temperature is as low as 100° C. or lower. The glass transition temperature can be elevated by bonding at least two substituents and preferably 2 to 4 substituents to the nucleus as described above. The specific biphenyl structure described above enhances solubility of the compound represented by general formula [9] and purification can be facilitated. When phenyl group is bonded at a position other than the above position, i.e., at the para-position, the content of impurities increases since purification becomes difficult and the properties of the obtained organic EL device deteriorate. By the substitution of aryl groups as described above, formation of pairs of the molecules by association is suppressed and the quantum efficiency of fluorescence emission increases. Thus, the efficiency of light emission of the organic EL device is improved.

In the compound represented by general formula [10] in the present invention, $Ar^1$ and $Ar^3$ each independently represents a divalent group selected from the group consisting of substituted and unsubstituted phenylene groups, substituted and unsubstituted 1,3-naphthalene groups, substituted and unsubstituted 1,8-naphthalene groups, substituted and unsubstituted fluorene groups and substituted and unsubstituted biphenyl groups, $Ar^2$ represents a divalent group selected from the group consisting of substituted and unsubstituted anthracene nuclei, substituted and unsubstituted pyrene nuclei, substituted and unsubstituted phenanthrene nuclei, substituted and unsubstituted chrysene nuclei, substituted and unsubstituted pentacene nuclei, substituted and unsubstituted naphthacene nuclei and substituted and unsubstituted fluorene nuclei. Examples of the divalent group include:

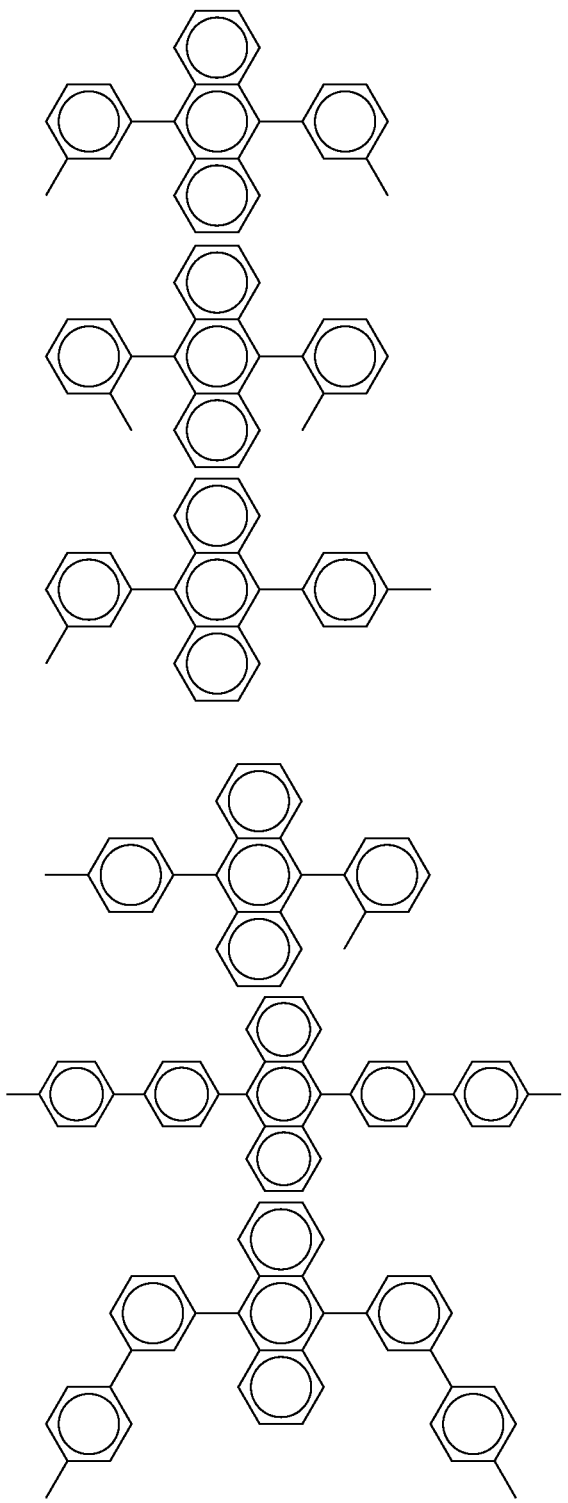

-continued

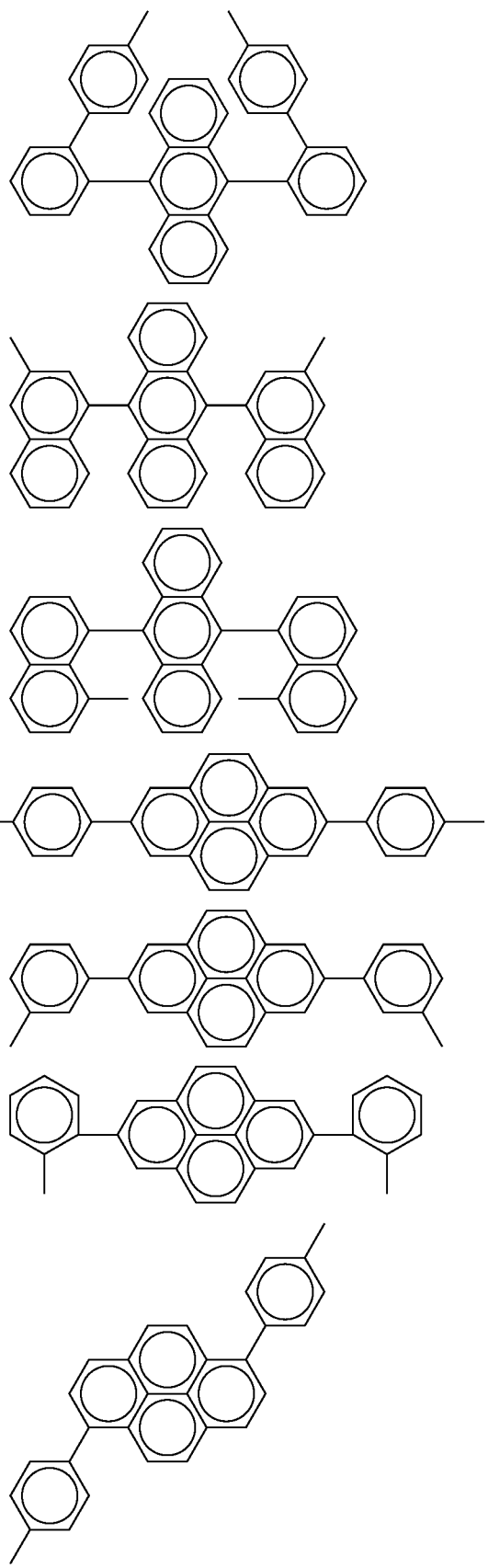

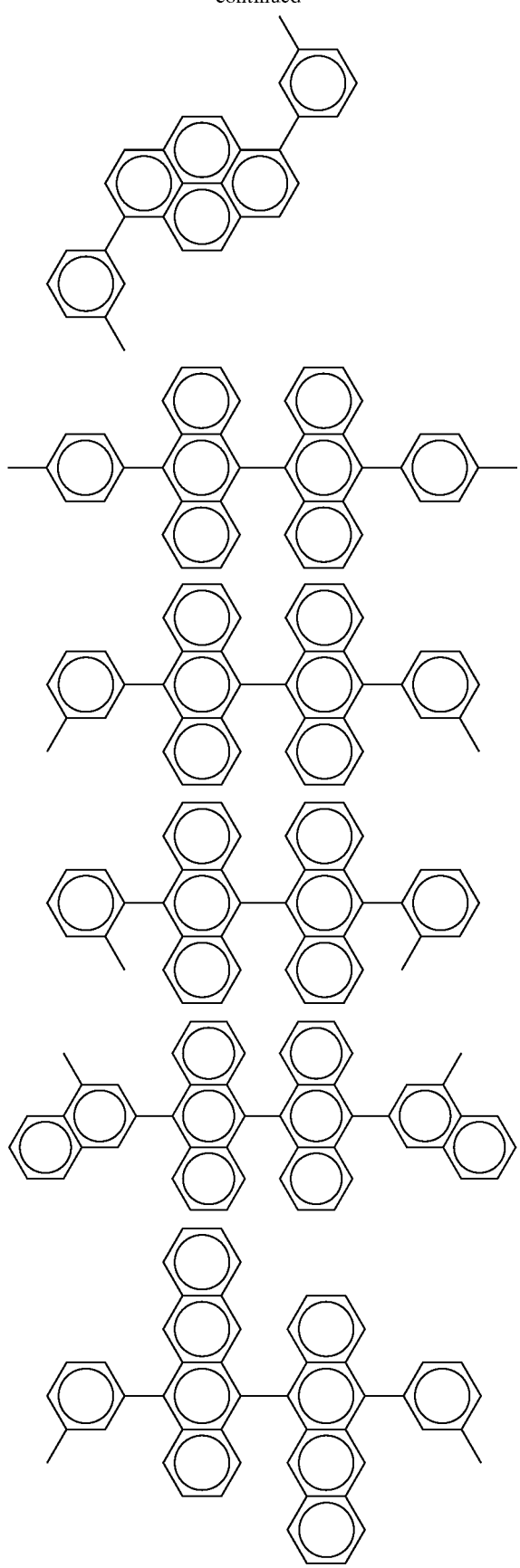

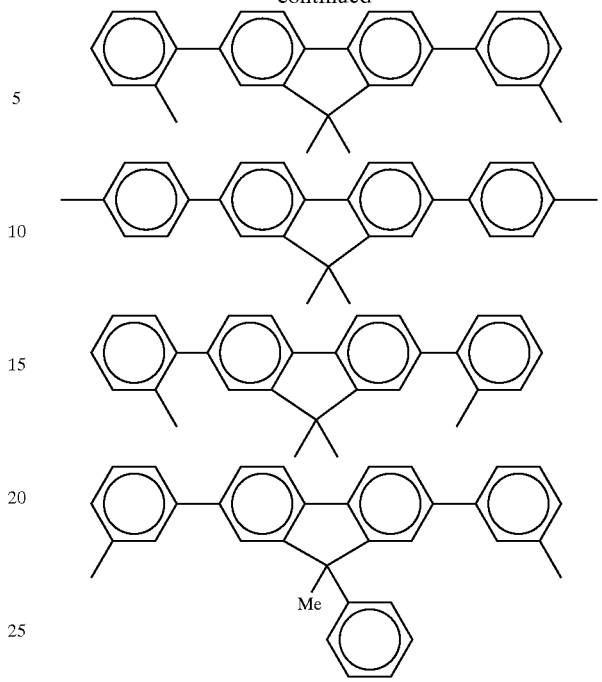

$X^5$ to $X^8$ and $Y^1$ to $Y^4$ each independently represent the same groups as those described in general formula [9]. a to d each represent an integer of 0 to 2, $a+b+c+d \leq 2$, e represents 0 or 1 and f represents 1 or 2, wherein, when $Ar^2$ represents an anthracene nucleus, the case in which $a=b=c=d$ and $Ar^1$ and $Ar^3$ both represent p-phenylene group is excluded.

As described above, since the compound represented by general formula [10] in the present invention has a diamine structure, the ionization energy is 5.6 eV or smaller and holes can be easily injected. The mobility of holes is $10^{-4}$ $m^2/V \cdot s$ or greater. Therefore, the compound has the excellent properties as the hole injecting material and the hole transporting material, in particular as the light emitting material. Due to the polyphenyl structure of the compound having the condensed ring at the center, electrons can be easily injected.

Since the compound has both of the polyphenyl structure and the diamine structure, a stable amorphous thin film can be formed and exhibits excellent heat resistance due to the glass transition temperature of 100° C. or higher. When the compound contains two or more structures represented by general formula [2], the condition of $a+b+c+d \leq 2$ is required because the compound decomposes under heating in vapor deposition for formation of the thin film. When $Ar^2$ represents an anthracene nucleus, decomposition under heating and oxidation in vapor deposition can be prevented by the above specific structures of $Ar^1$ and $Ar^3$.

In the compounds represented by general formulae [11] and [11'] in the material for the organic EL devices and the novel compound used in the organic EL device of the present invention, F represents a substituted or unsubstituted arylene group having 6 to 21 carbon atoms. Examples of the group represented by F include divalent groups formed from biphenyl, terphenyl, naphthalene, anthracene, phenanthrene, pyrene, fluorene, thiophene and fluoranthene.

In general formulae [11] and [11'], a to d each represent an integer of 0 to 2, wherein $a+b+c+d>0$.

As described above, since the compounds represented by general formulae [11] and [11'] in the present invention have a diamine structure at the center and a styrylamine structure at end portions, the ionization energy is 5.6 eV or smaller. Therefore, the property of injecting holes into the light emitting layer is improved by adding the compound into the light emitting layer. Moreover, the balance between electrons and holes in the light emitting layer is improved by catching holes and the efficiency of light emission and the life are improved. The efficiency of light emission and the life are improved in comparison with the case in which the light emitting layer is composed of the above compound represented by general formula [11] or [11'] alone as the sole material for the organic EL material The compound having the structure in which $X^1$ and $X^2$ are bonded to each other and $X^3$ and $X^4$ are bonded to each other through a single bond or through a carbon ring bond provides an elevated glass transition temperature and improved heat resistance.

In the group represented by general formulae [12] to [14] in the present invention, $R^{5'}$ to $R^{34'}$ each independently represent hydrogen atom, a substituted or unsubstituted alkyl group having 1 to 20 carbon atoms, a substituted or unsubstituted aryl group having 6 to 20 carbon atoms or cyano group and adjacent groups among the groups represented by $R^{5'}$ to $R^{24'}$ may be bonded to each other to form a saturated or unsaturated carbon ring. Examples of the group represented by $R^{5'}$ to $R^{34'}$ include substituted and unsubstituted alkyl groups such as methyl group, ethyl group, propyl group, butyl group, sec-butyl group, tert-butyl group, pentyl group, hexyl group, heptyl group, octyl group, stearyl group, 2-phenylisoproyl group, trichloromethyl group, trifluoromethyl group, benzyl group, α-phenoxybenzyl group, α,α-dimethylbenzyl group, α,α-methylphenylbenzyl group, α,α-ditrifluoromethylbenzyl group, triphenylmethyl group and α-benzyloxybenzyl group; and substituted and unsubstituted aryl groups such as phenyl group, 2-methylphenyl group, 3-methylphenyl group, 4-methylphenyl group, 4-ethylphenyl group, biphenyl group, 4-methylbiphenyl group, 4-ethylbiphenyl group, 4-cyclohexylbiphenyl group, terphenyl group, 3,5-dichlorophenyl group, naphthyl group, 5-methylnaphthyl group, anthryl group and pyrenyl group.

In the following, Compounds (1) to (28) as the typical examples of the compound represented by general formula [1], Compounds (29) to (56) as the typical examples of the compounds represented by general formulae [3] to [6], Compounds (57) to (74) as the typical examples of the compound represented by general formula [7], Compounds (75) to (86) as the typical examples of the compound represented by general formula [8], Compounds (87) to (104) as the typical examples of the compound represented by general formula [9], Compounds (105) to (126) as the typical examples of the compound represented by general formula [10] and Compounds (127) to (141) as the typical examples of the compounds represented by general formulae [11] and [11'] are shown. However, the present invention is not limited to these typical examples.

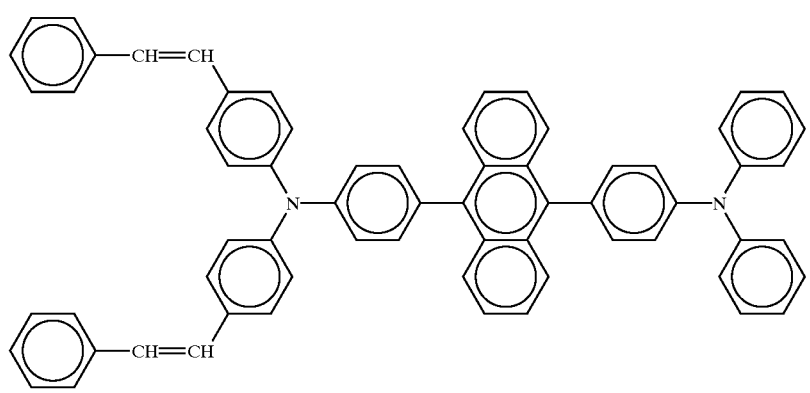

(1)

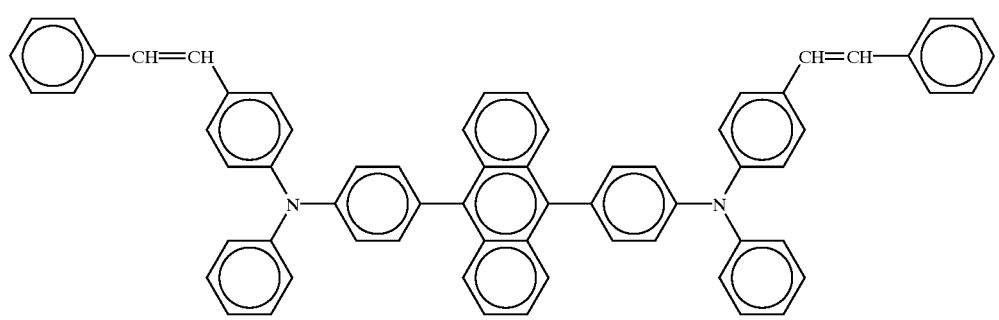

(2)

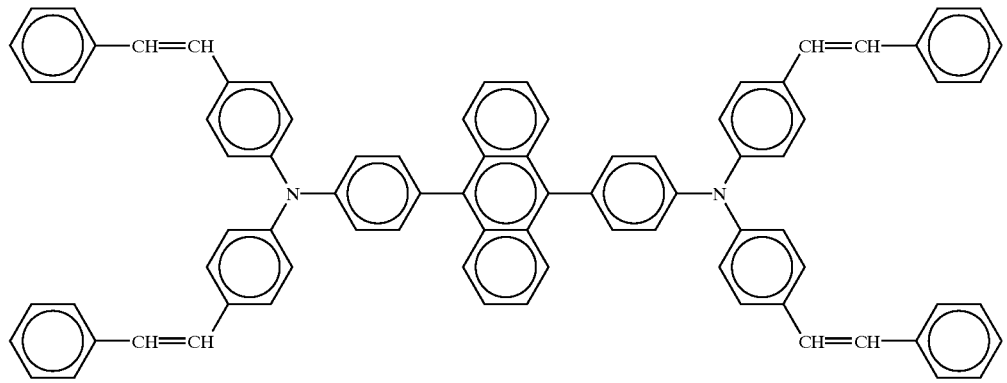
(3)
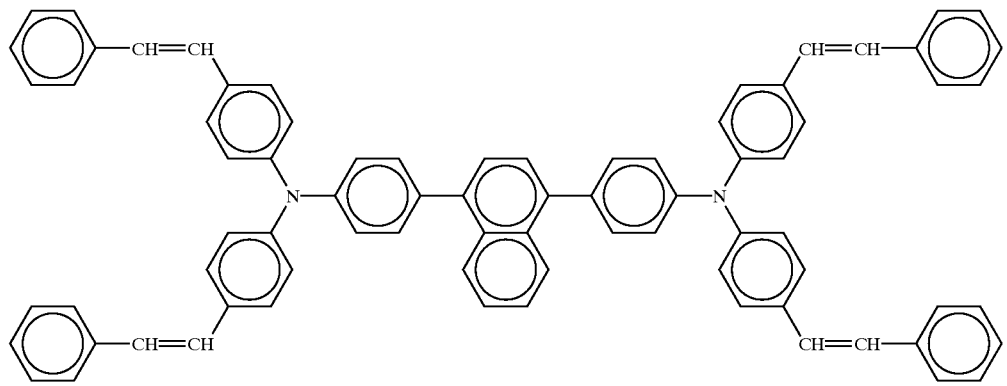
(4)
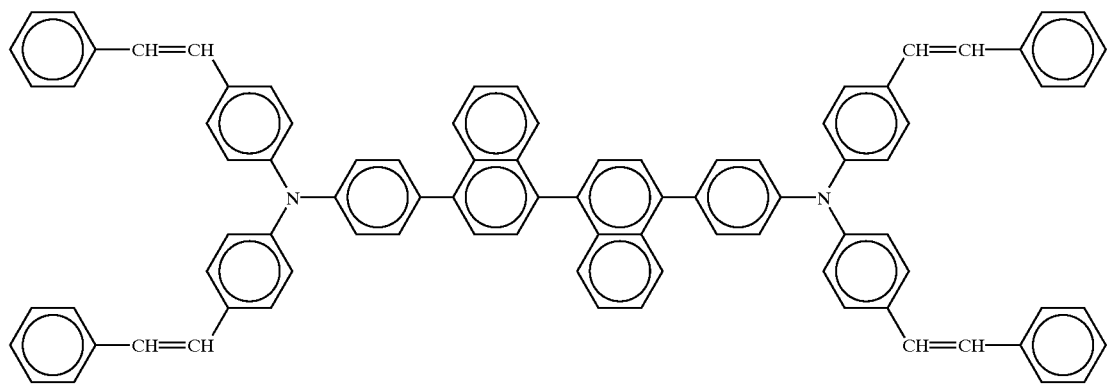
(5)
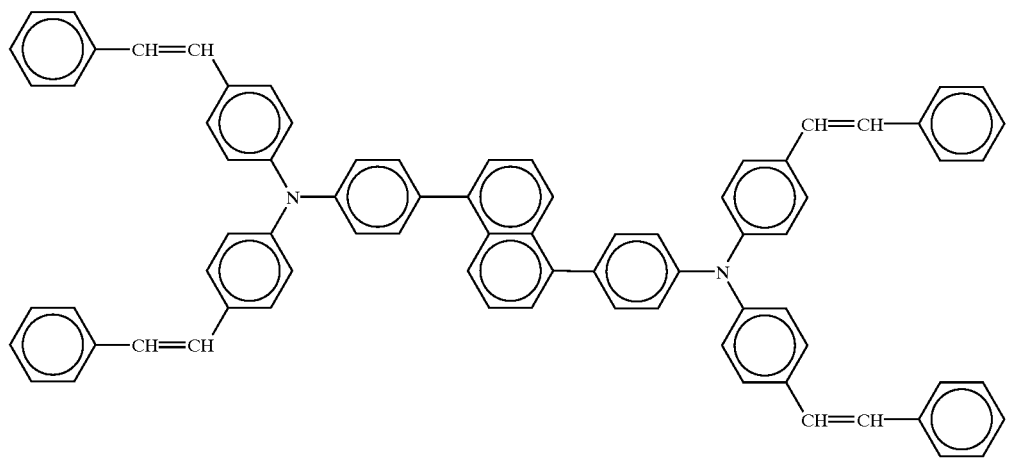
(6)

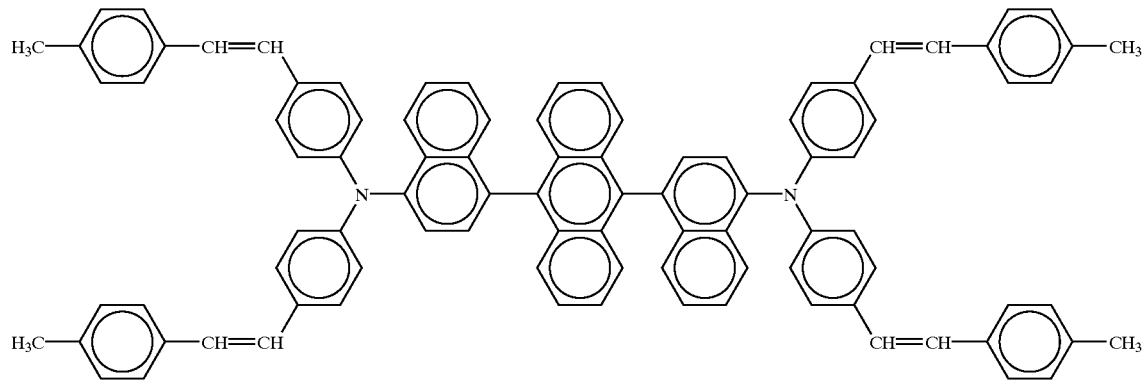
(7)
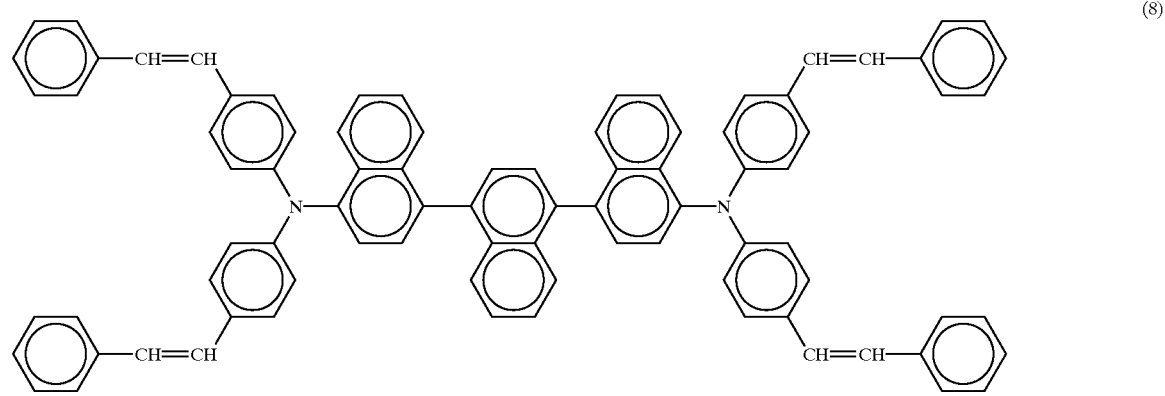
(8)
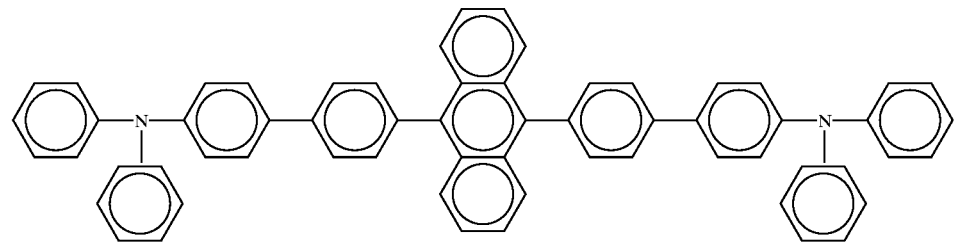
(9)
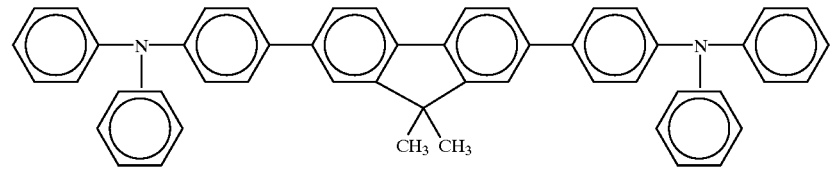
(10)
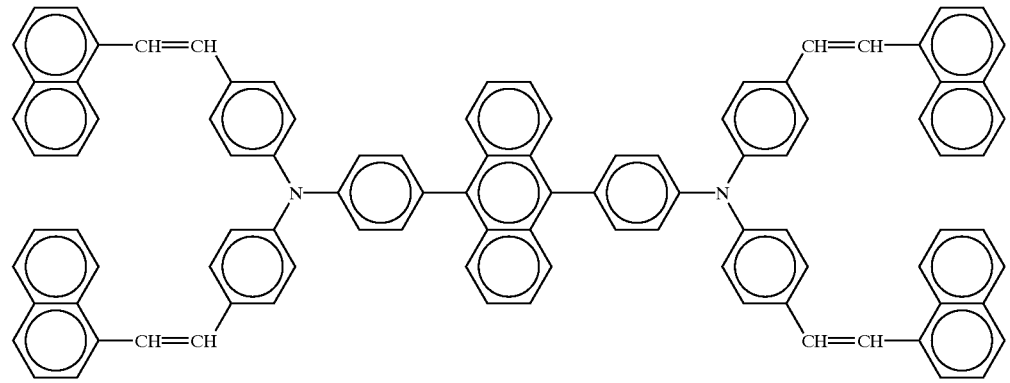
(11)

(12)
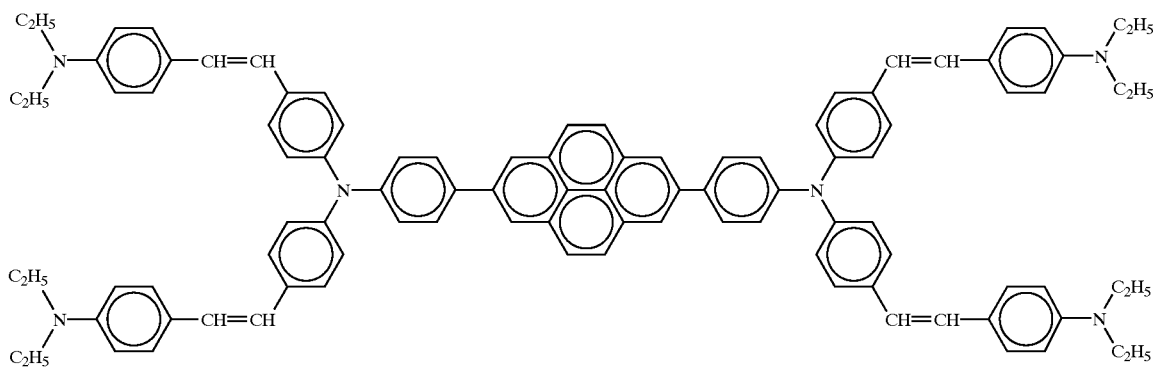
(13)
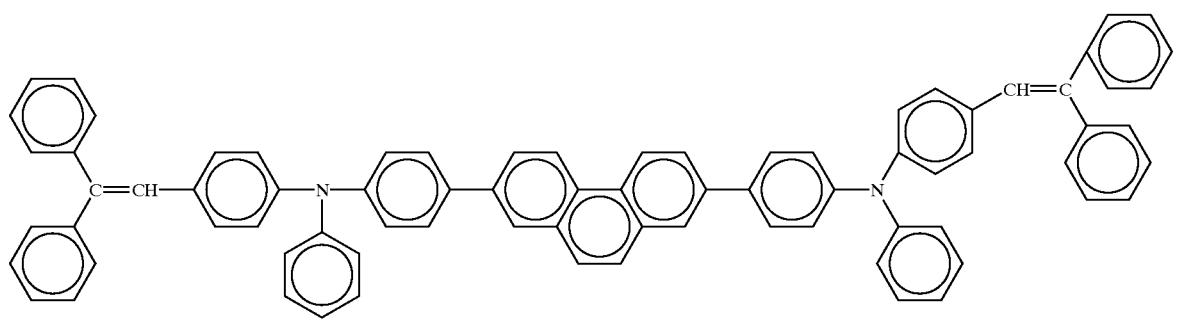
(14)
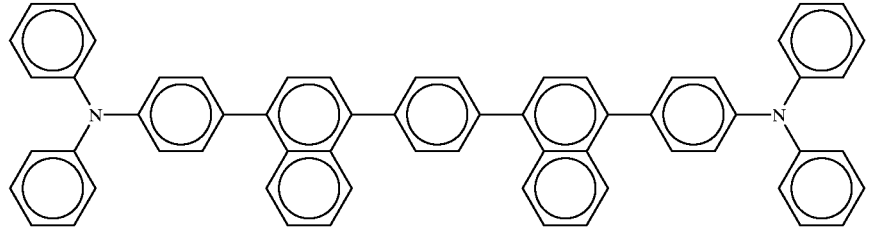
(15)
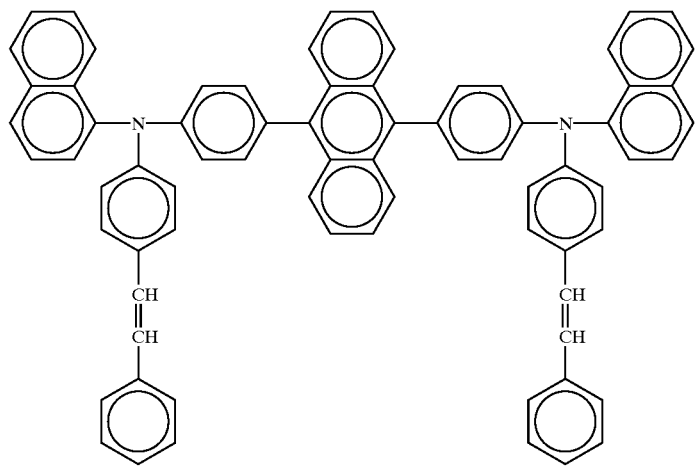

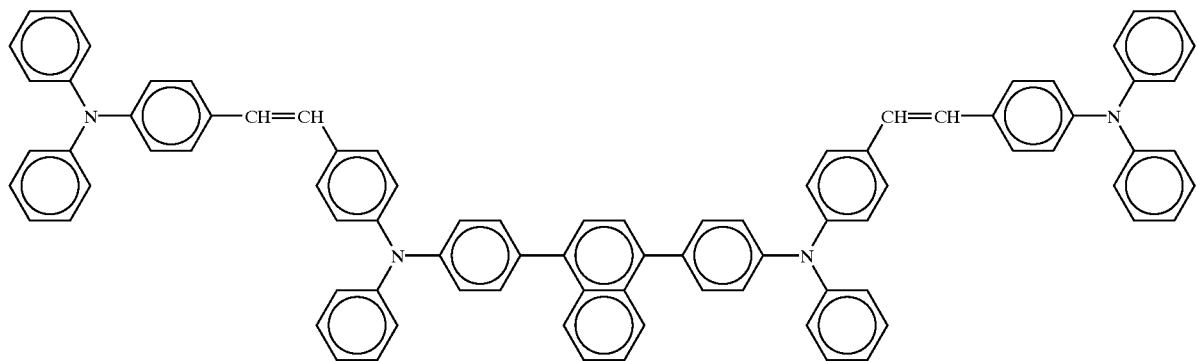
(16)
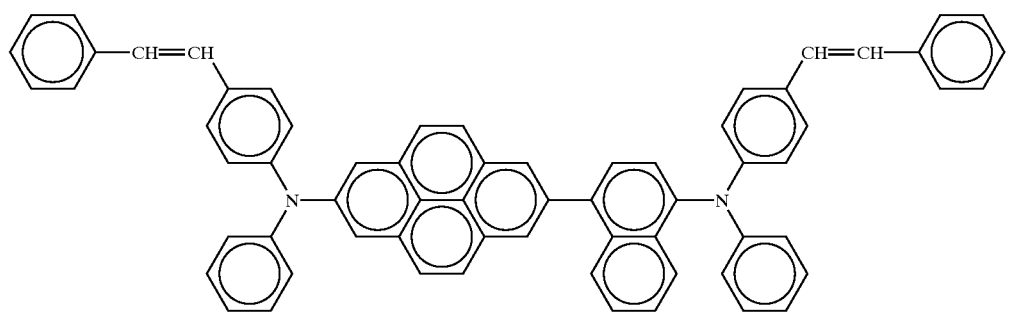
(17)
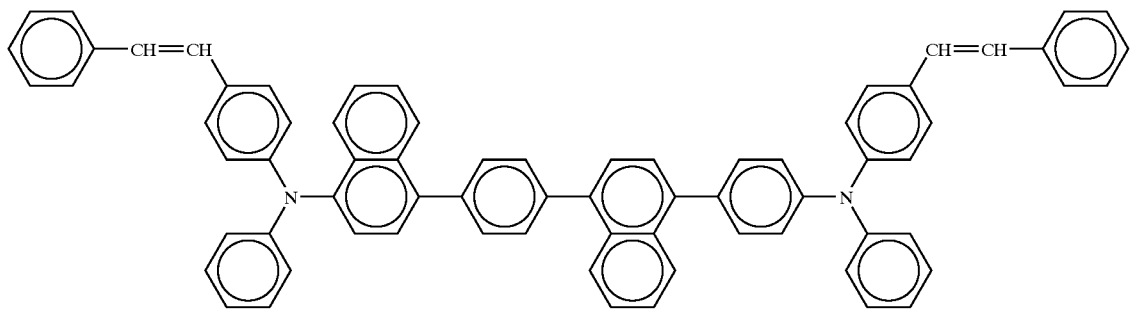
(18)
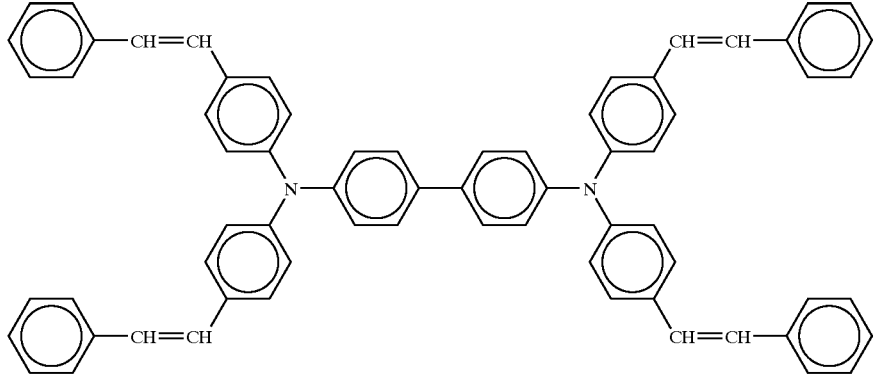
(19)

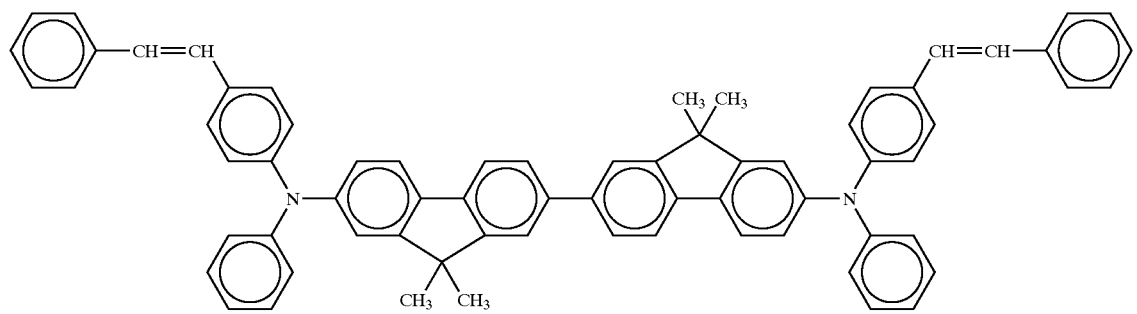
(20)
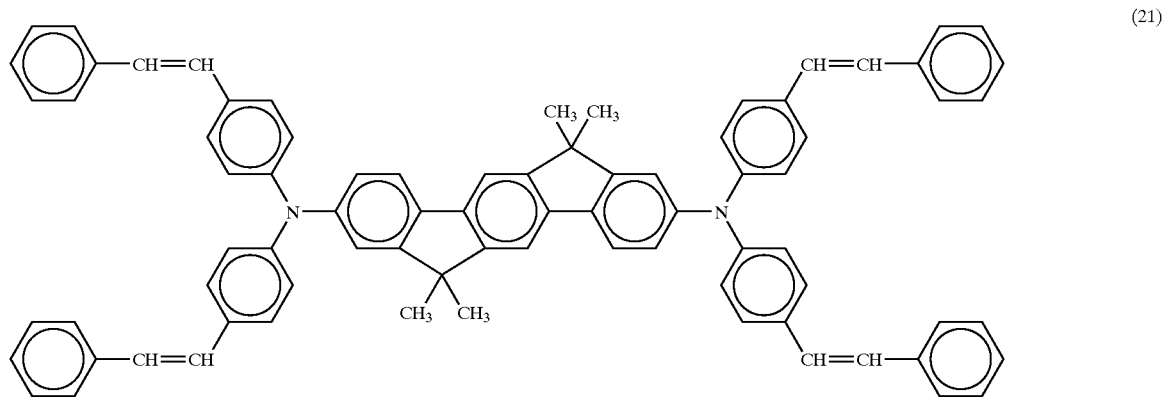
(21)
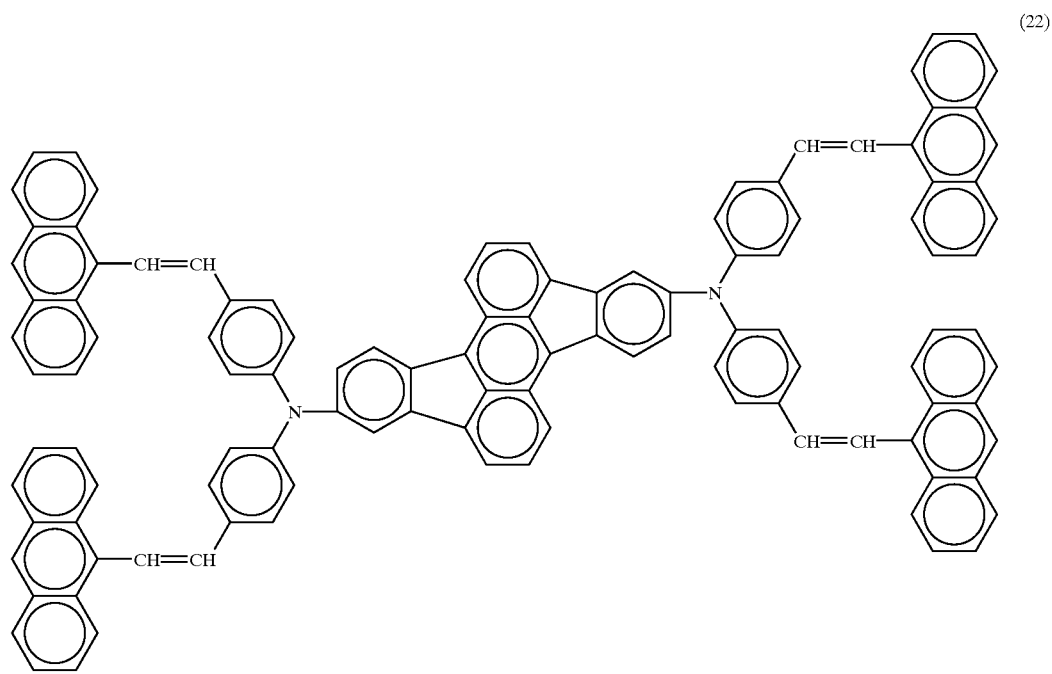
(22)

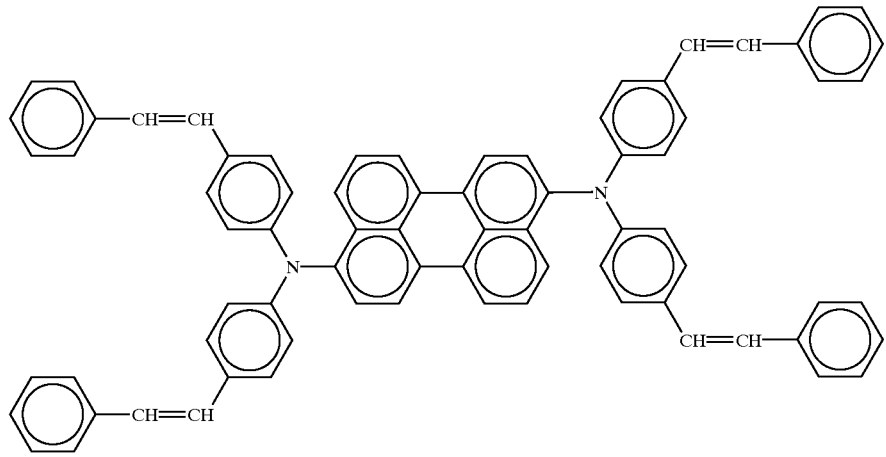
(23)
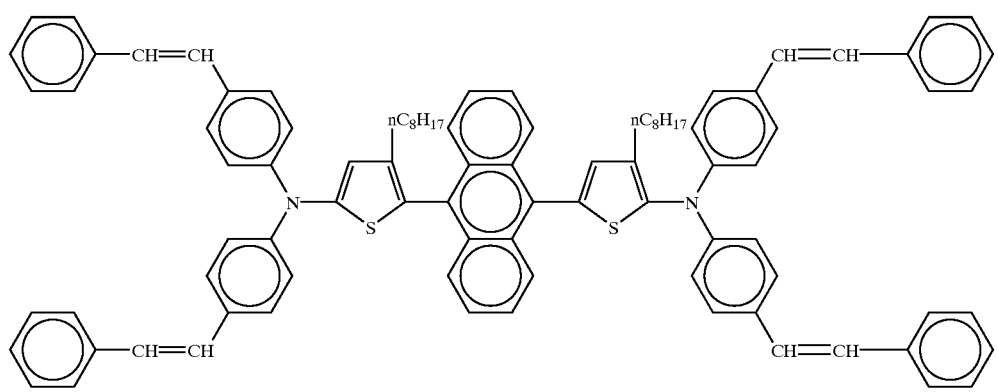
(24)
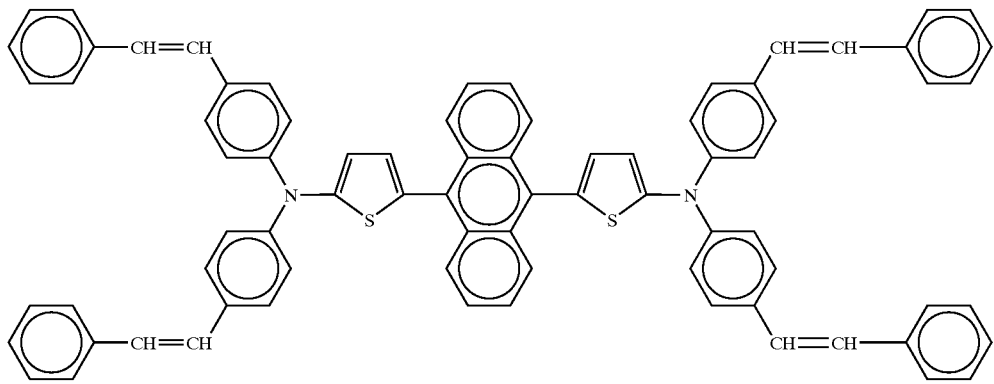
(25)
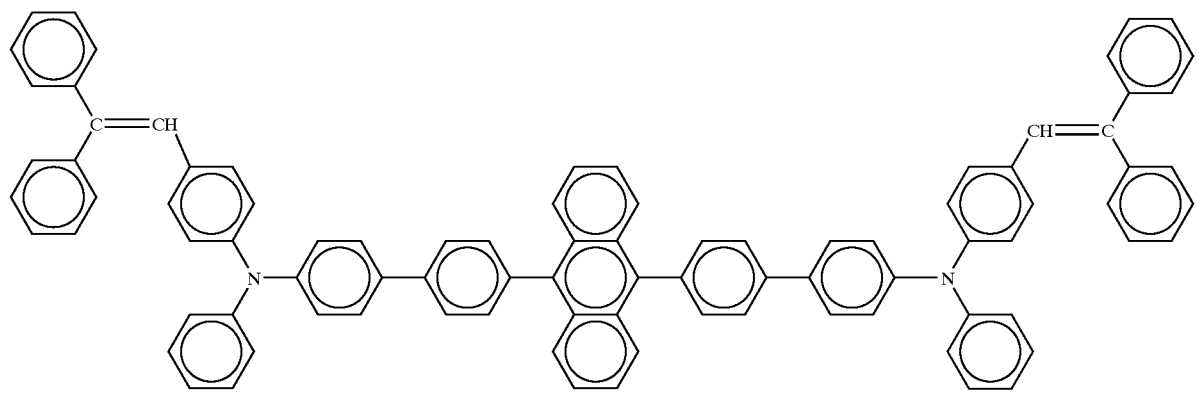
(26)

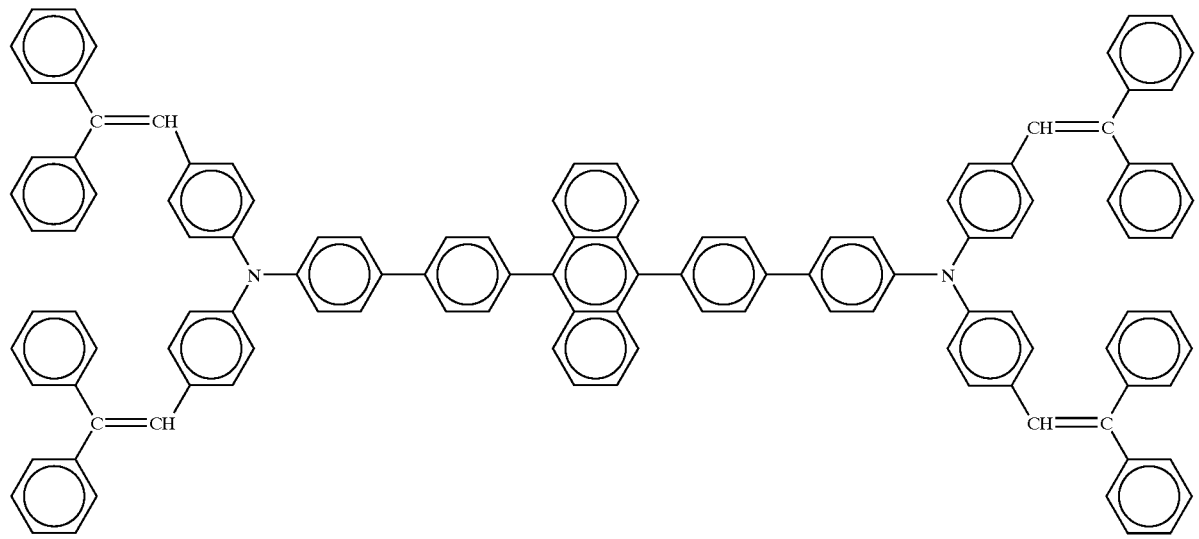
(27)
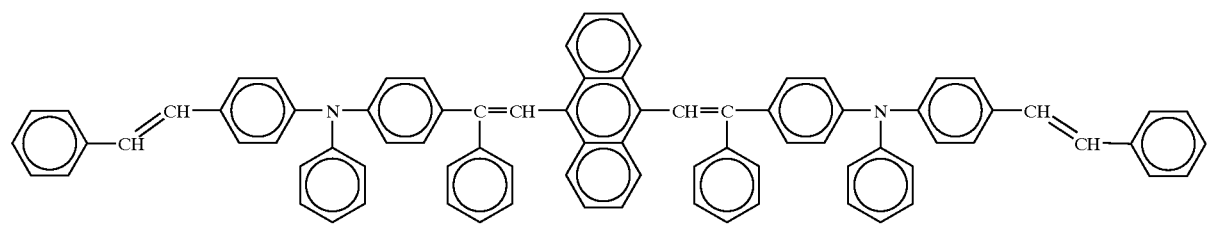
(28)
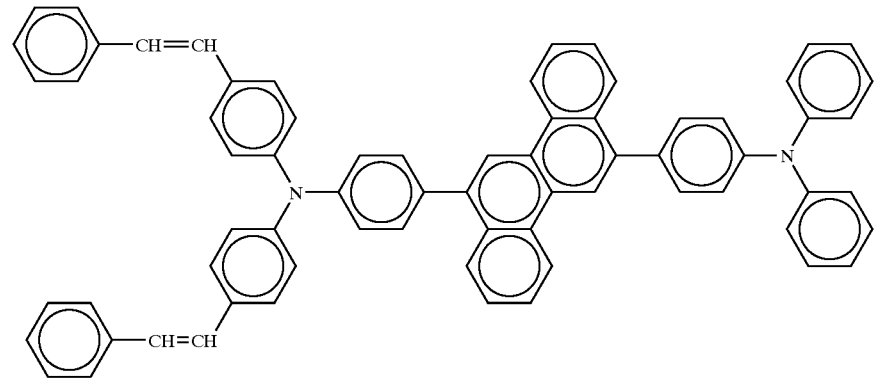
(29)
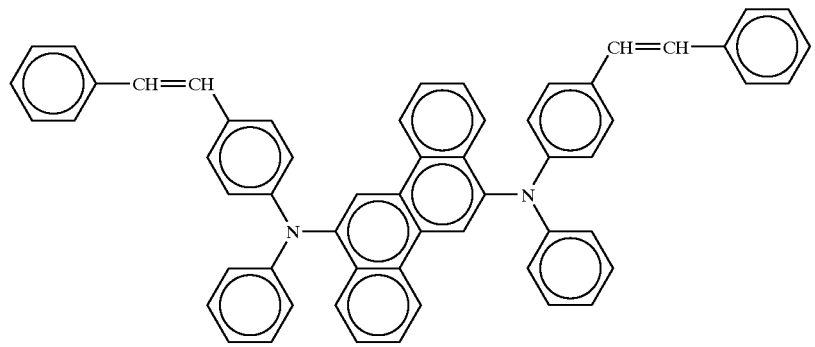
(30)

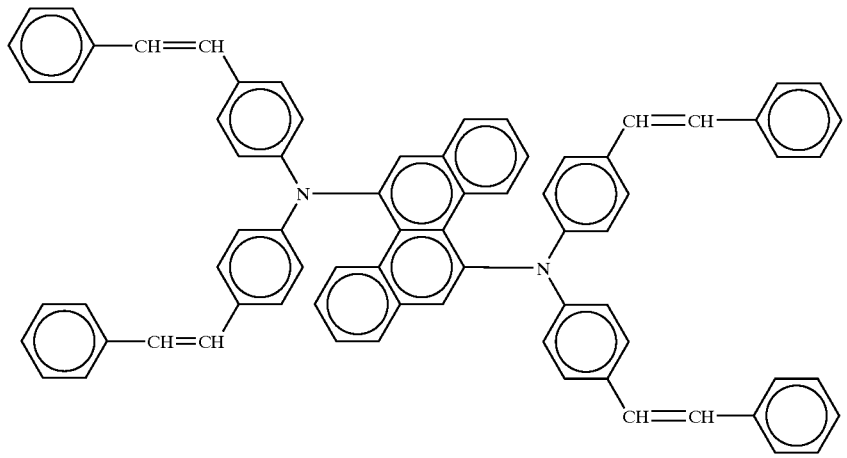
(31)
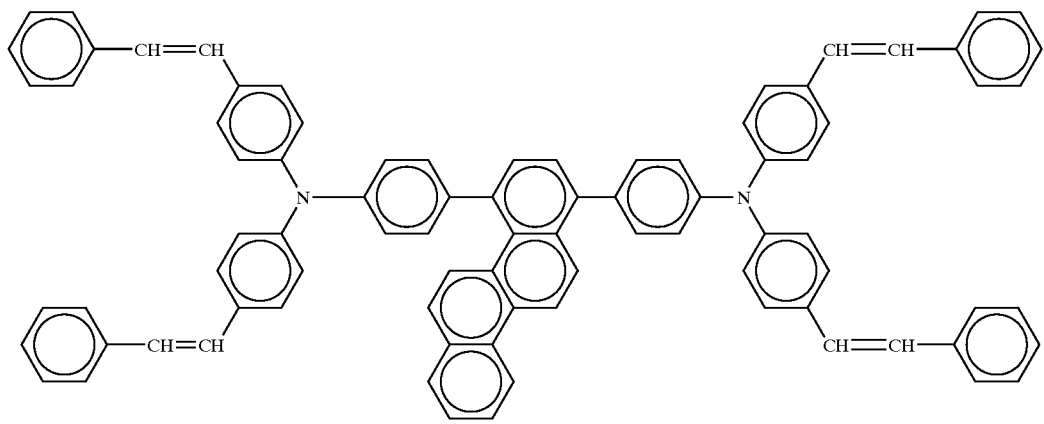
(32)
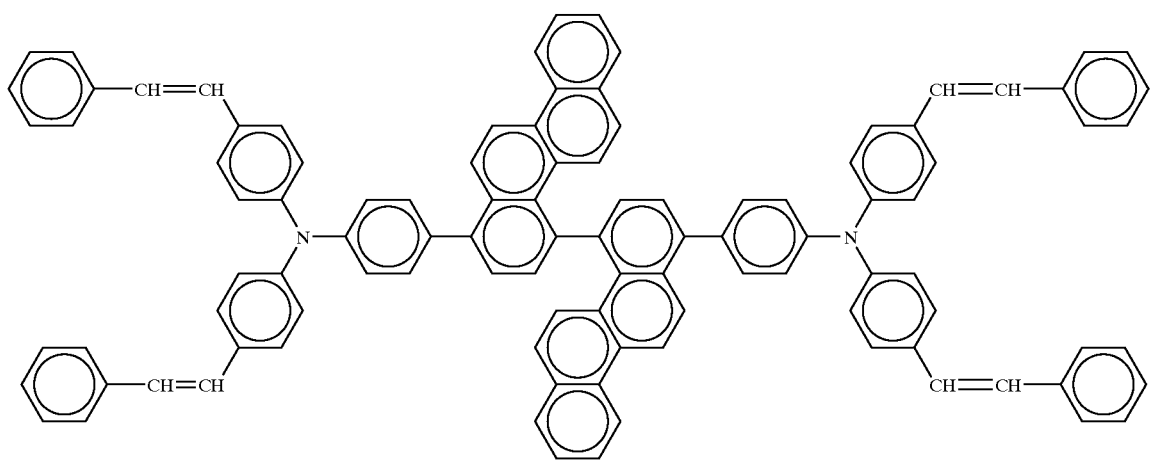
(33)

-continued
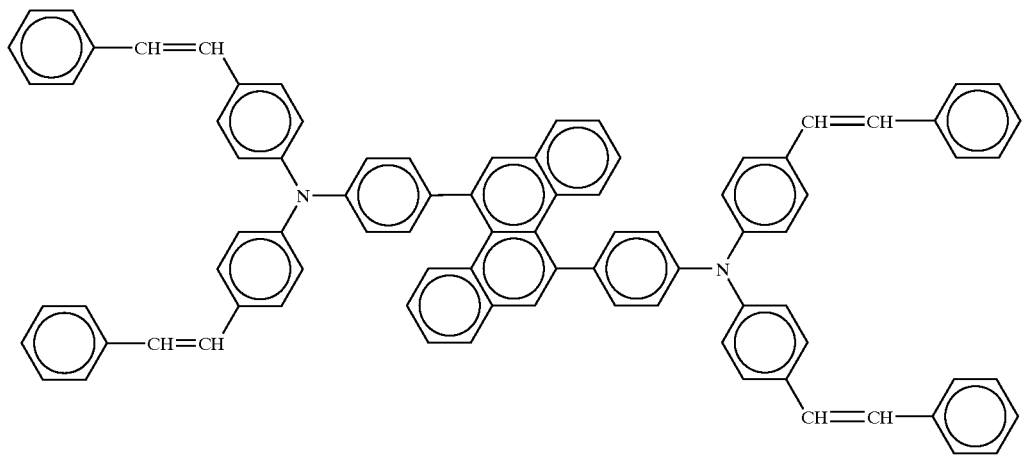
(34)
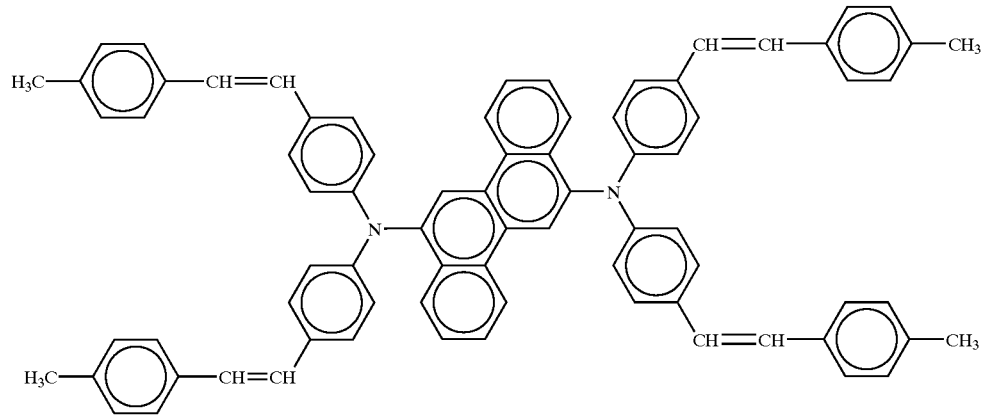
(35)
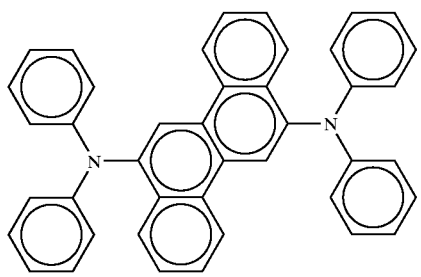
(36)
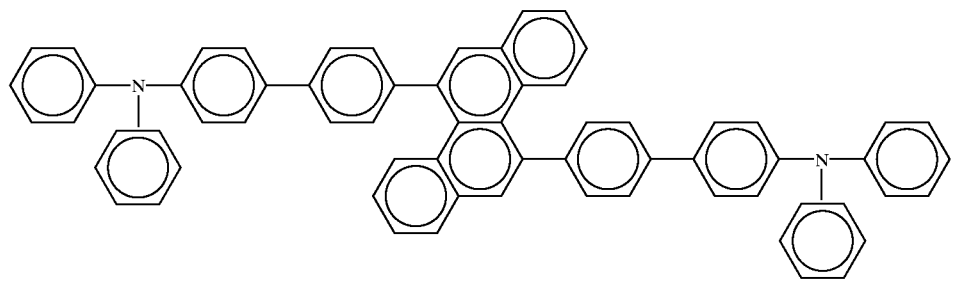
(37)

(38)
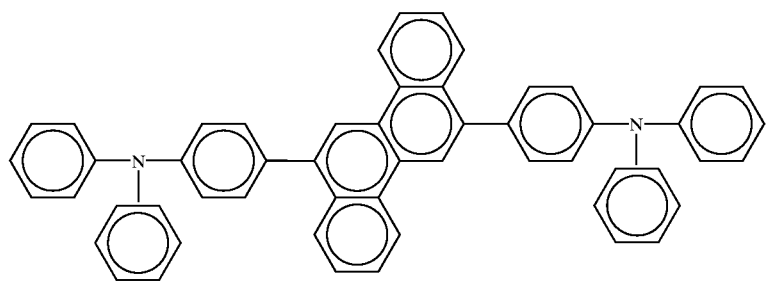
(39)
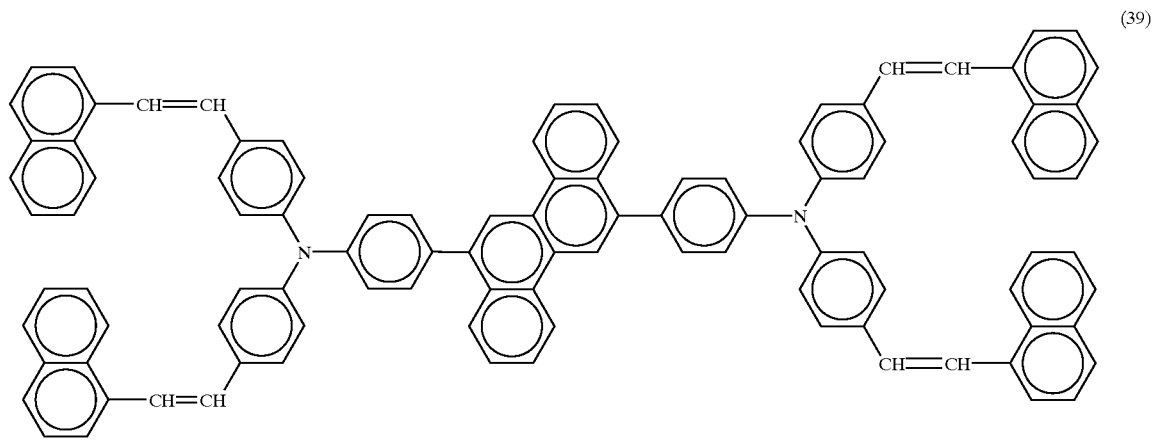
(40)
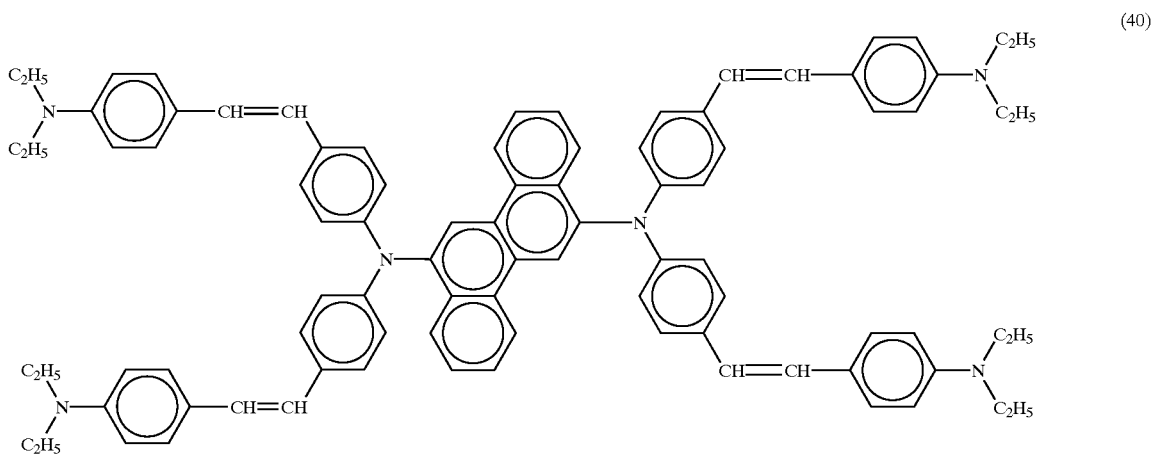
(41)
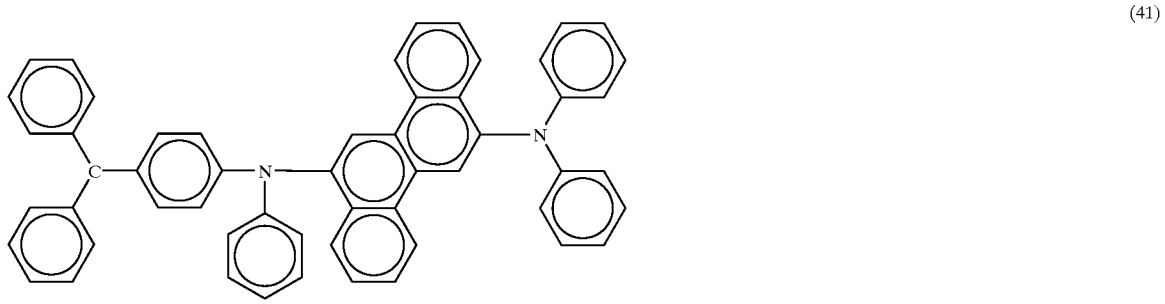

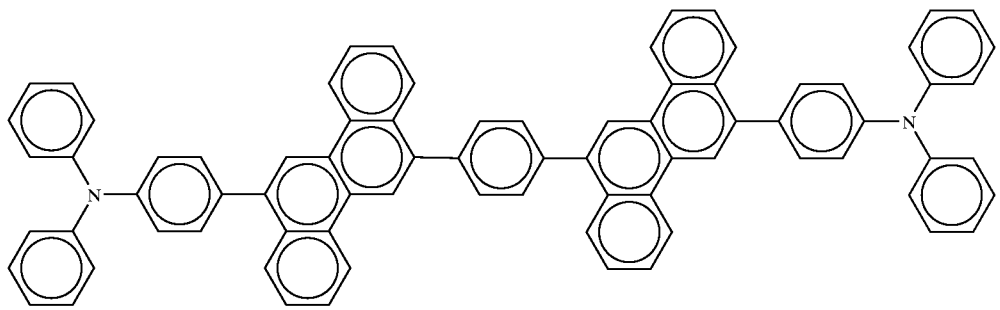
(42)
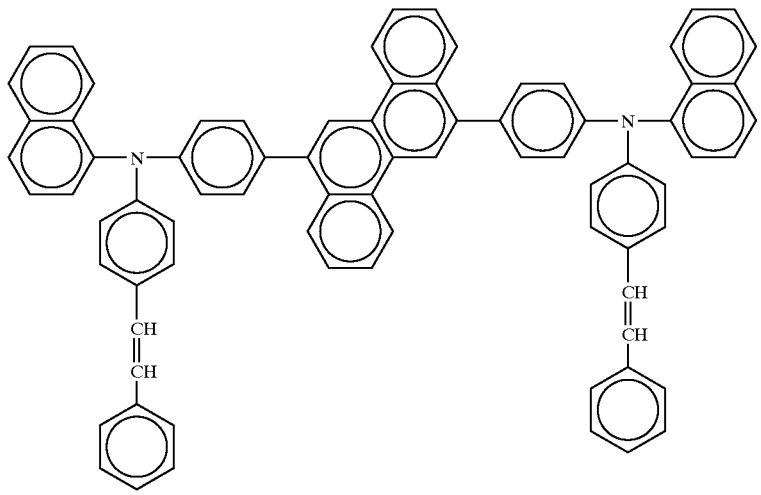
(43)
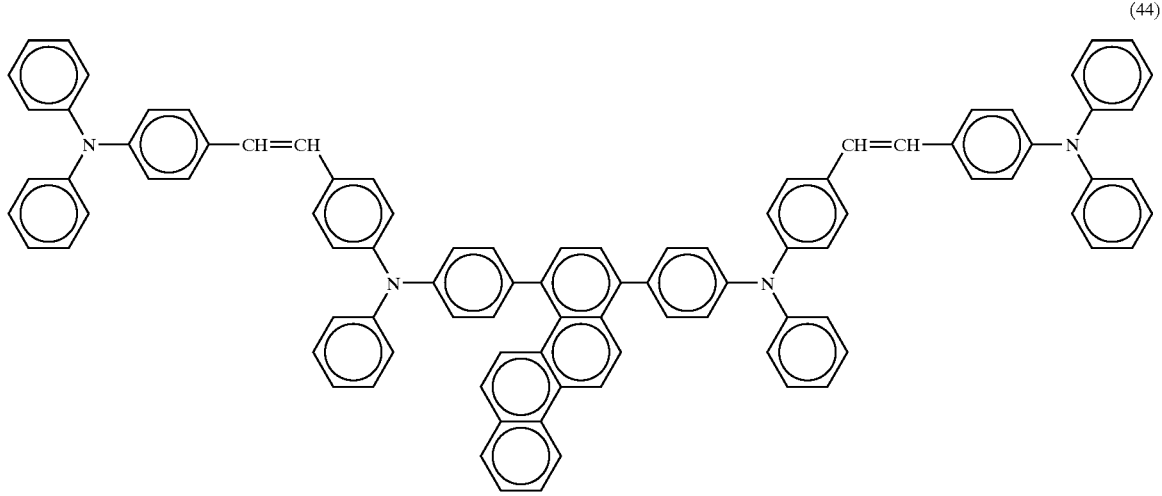
(44)

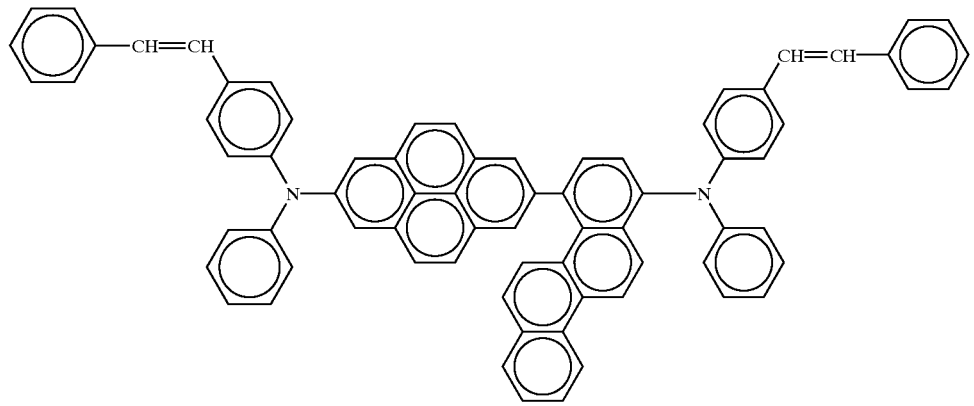
(45)
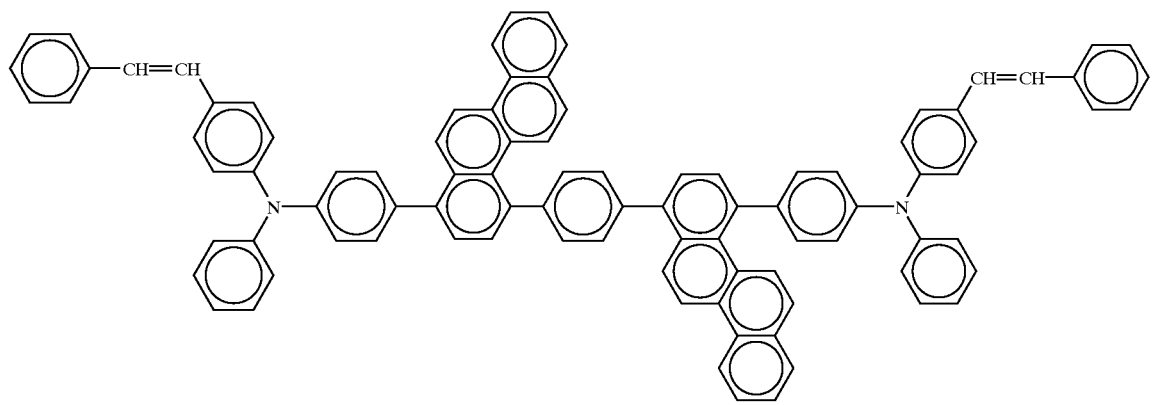
(46)
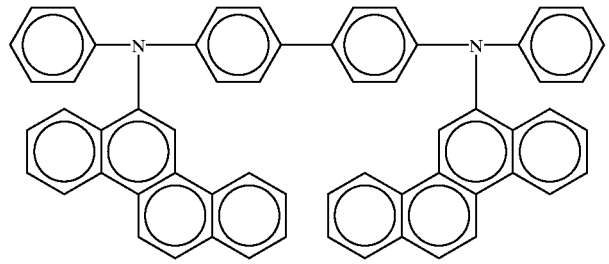
(47)
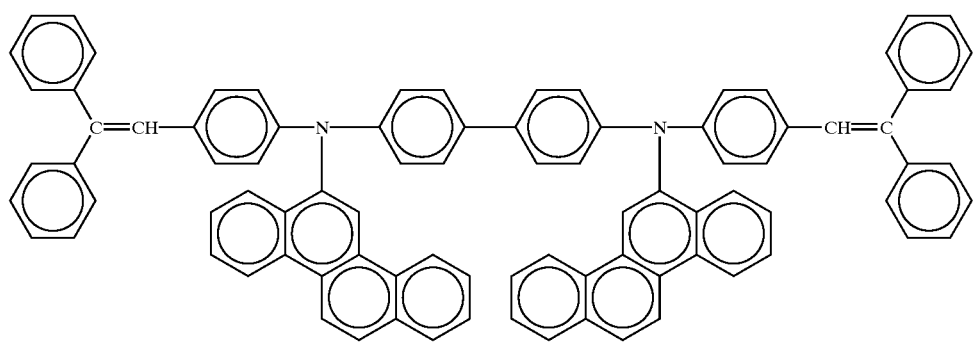
(48)

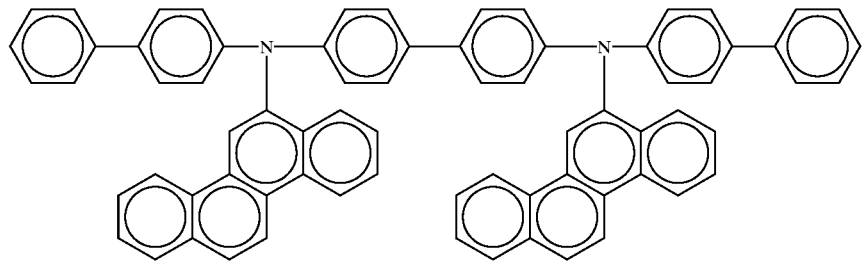
(49)
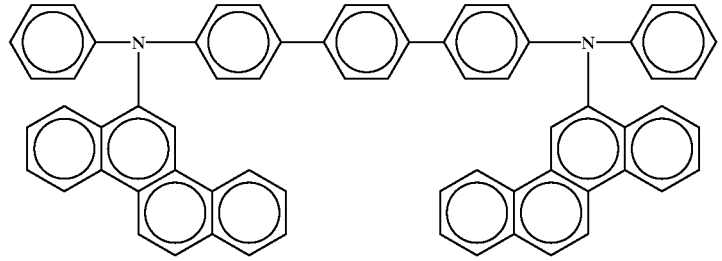
(50)
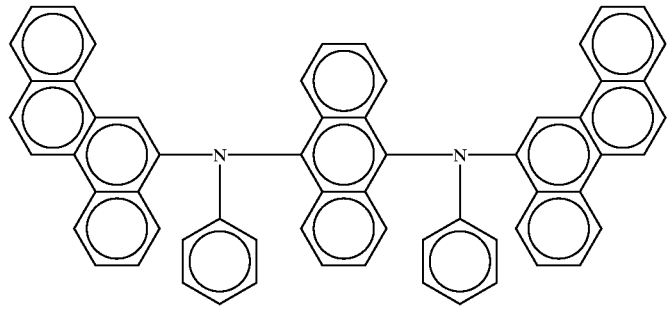
(51)
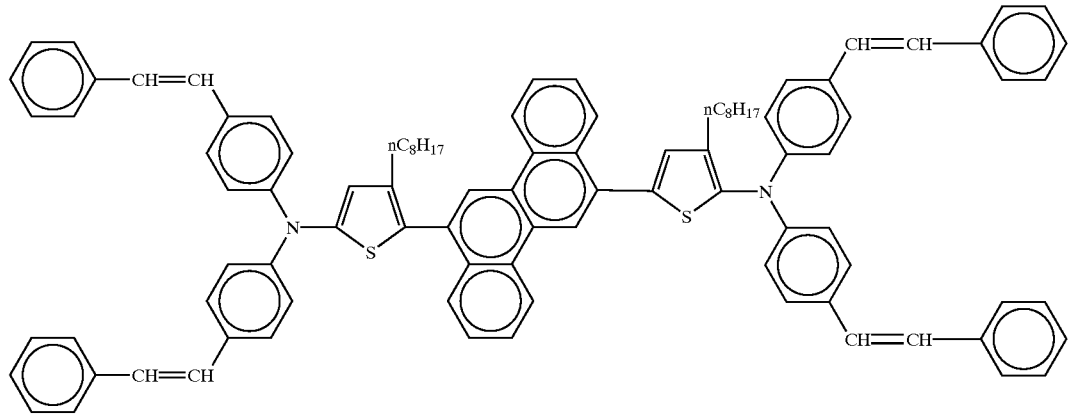
(52)
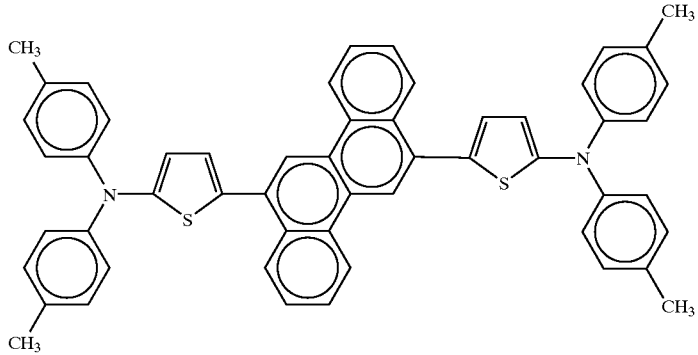
(53)

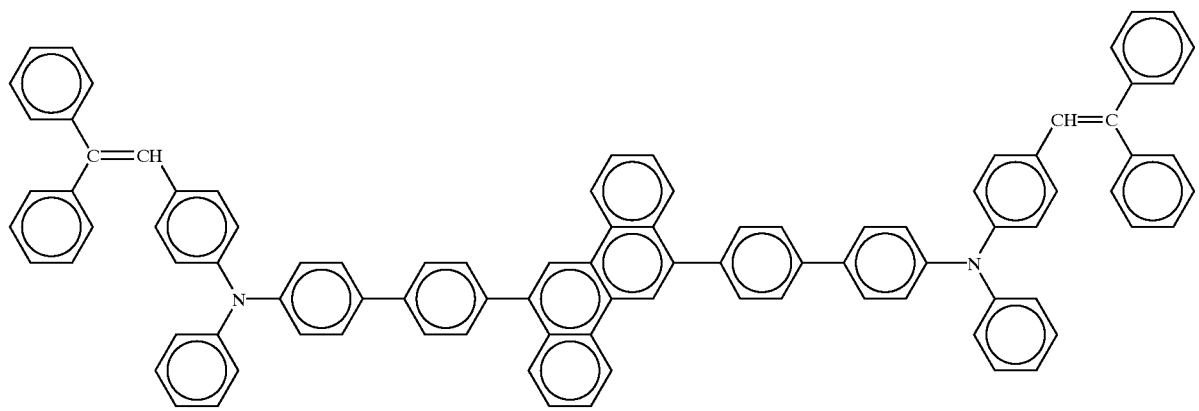
(54)
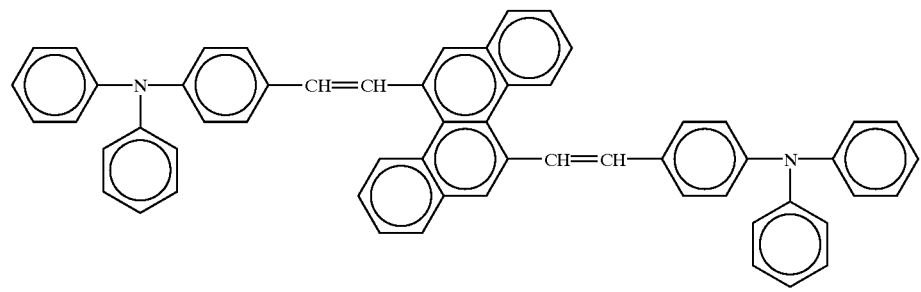
(55)
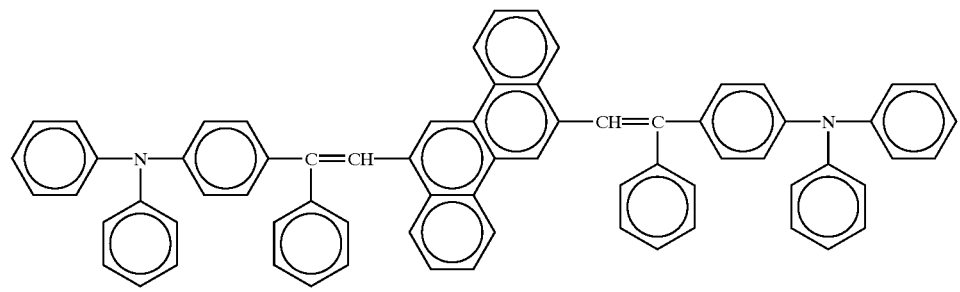
(56)
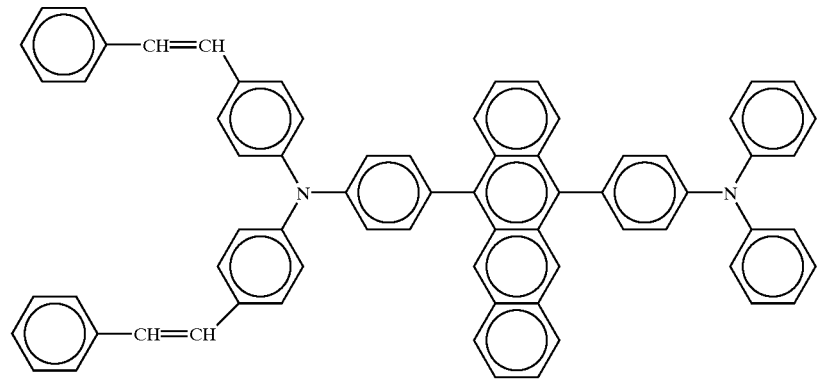
(57)

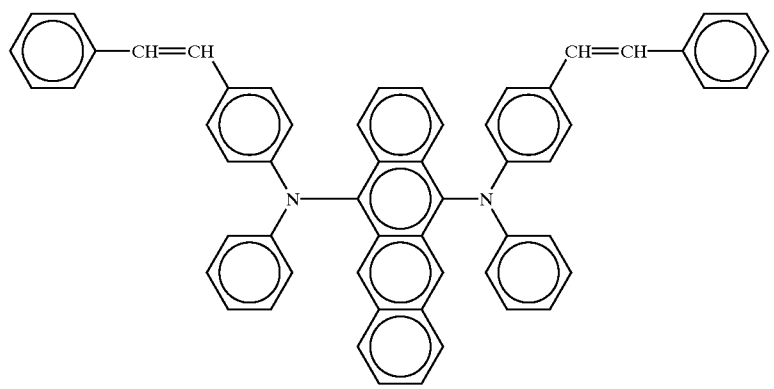
(58)
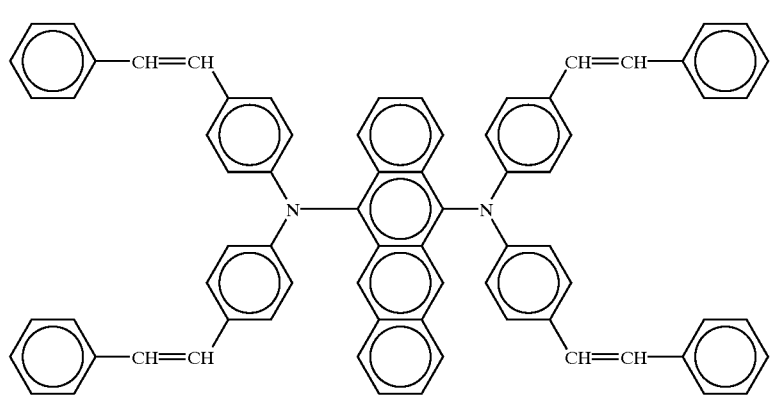
(59)
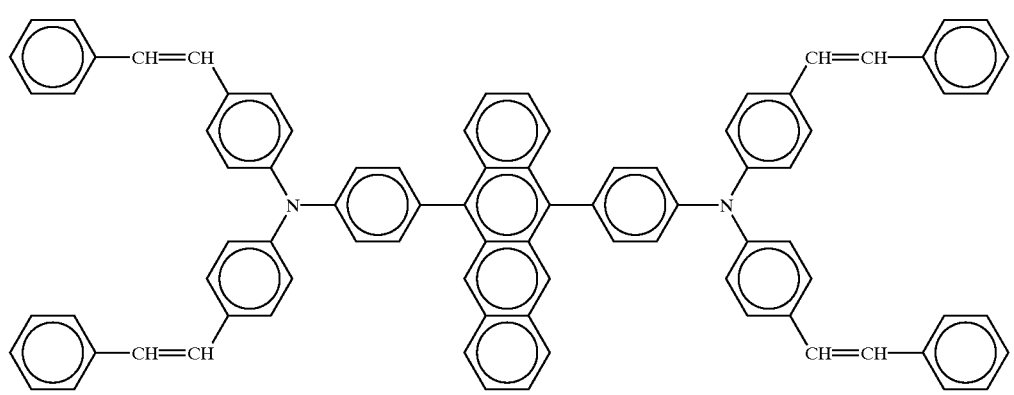
(60)
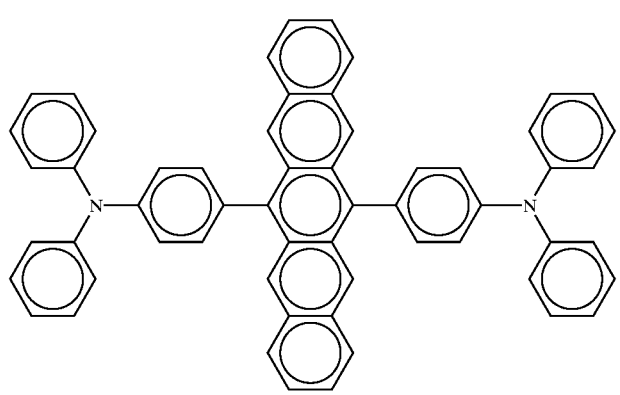
(61)

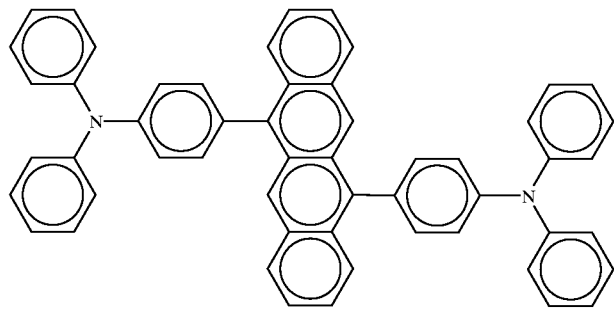
(62)
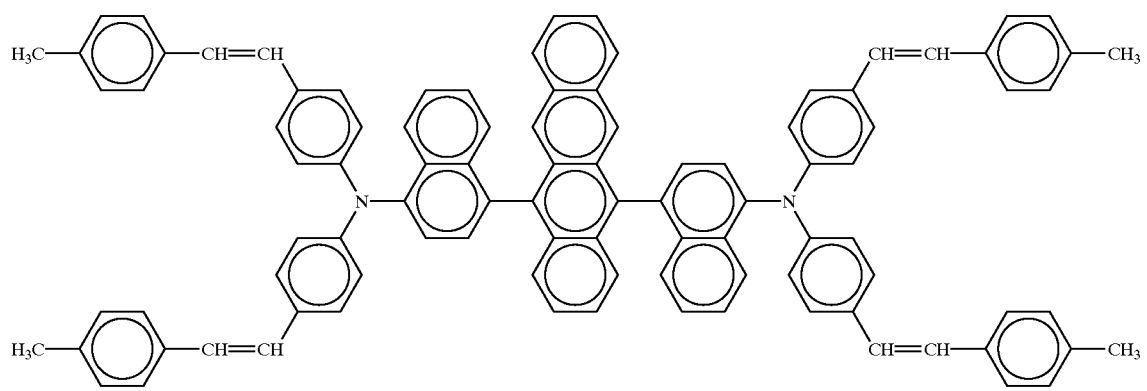
(63)
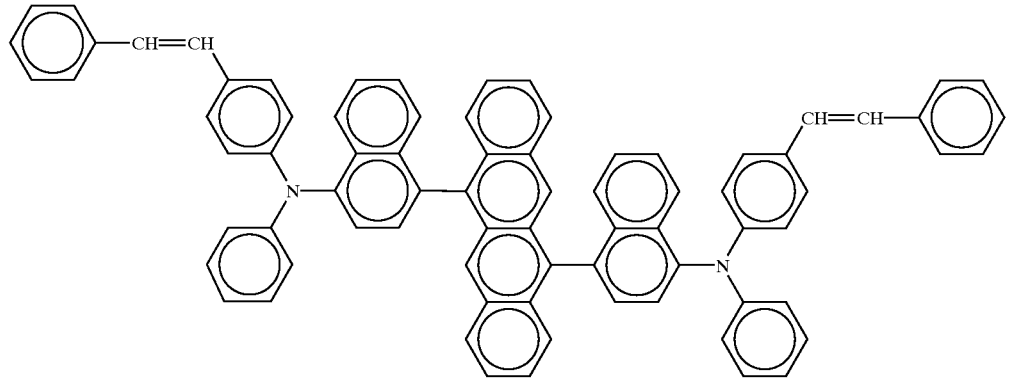
(64)
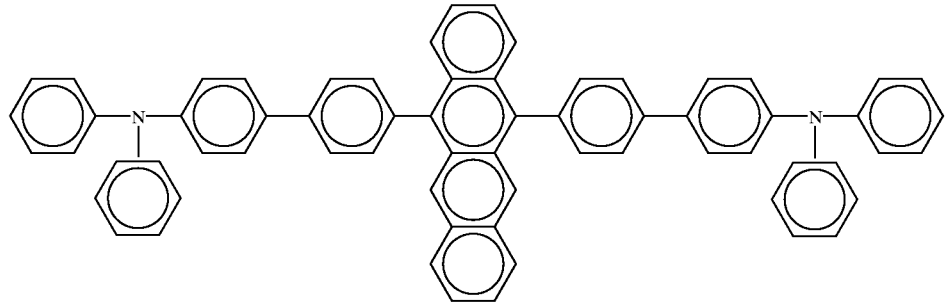
(65)

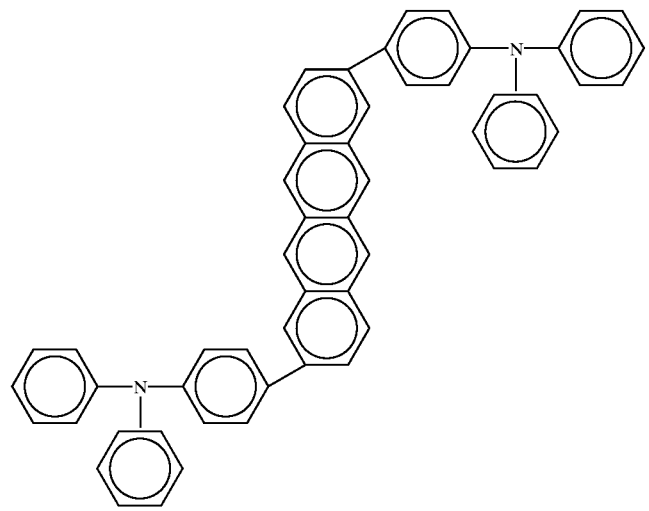
(66)
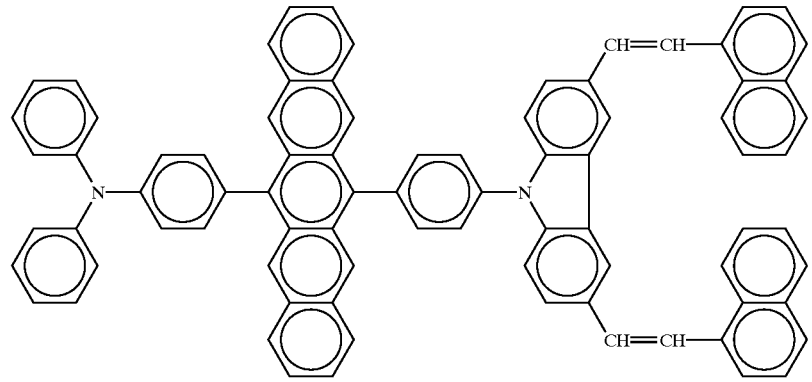
(67)
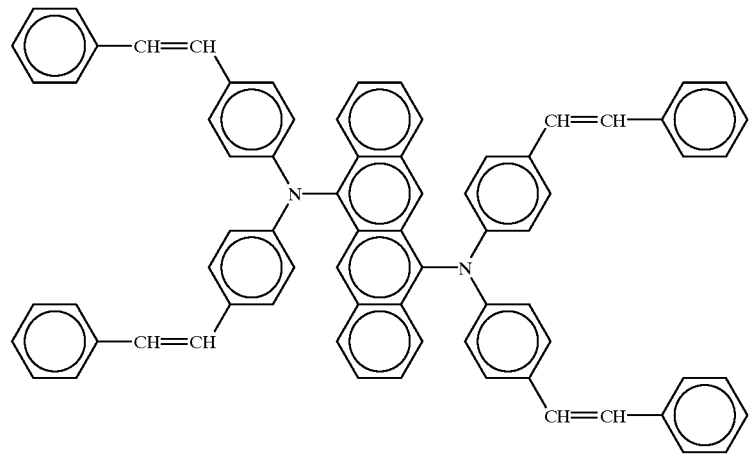
(68)
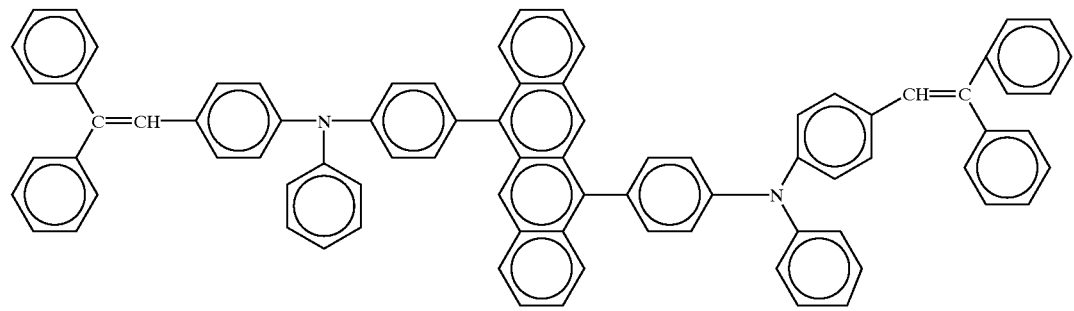
(69)

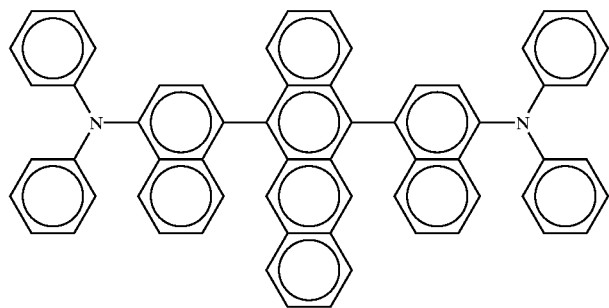
(70)
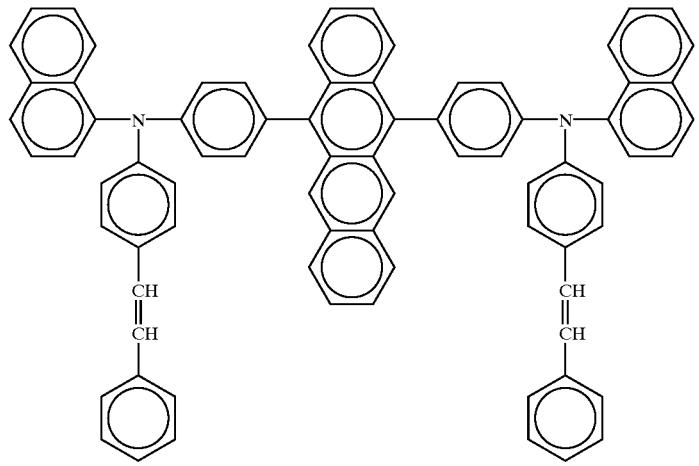
(71)
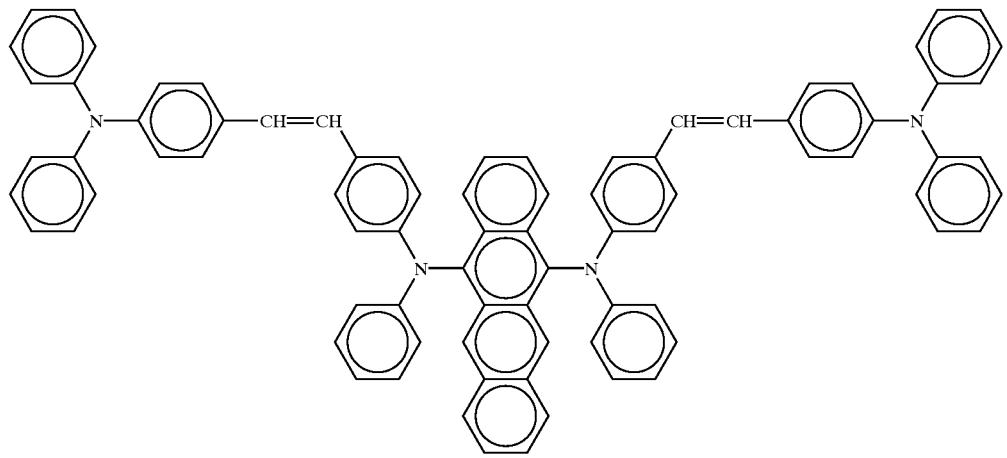
(72)
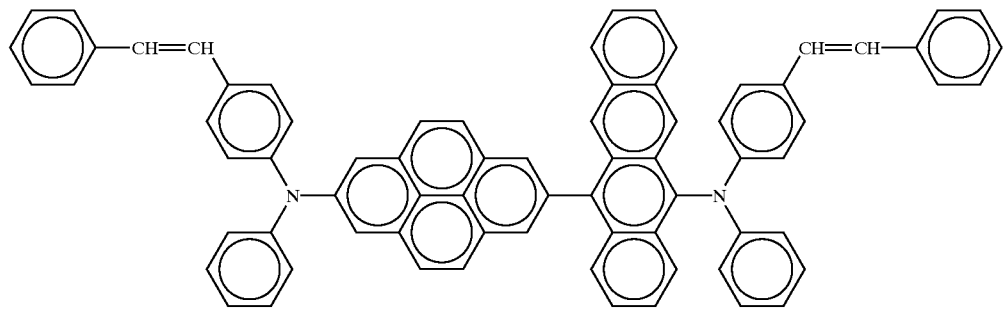
(73)

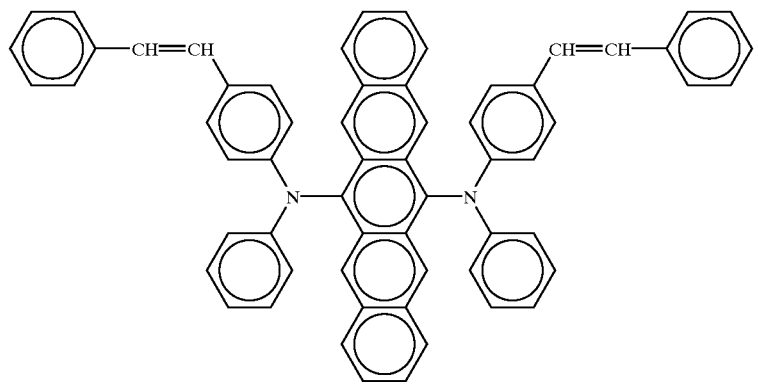
(74)
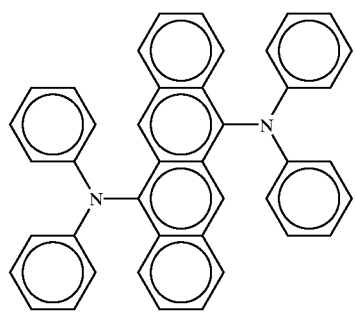
(75)
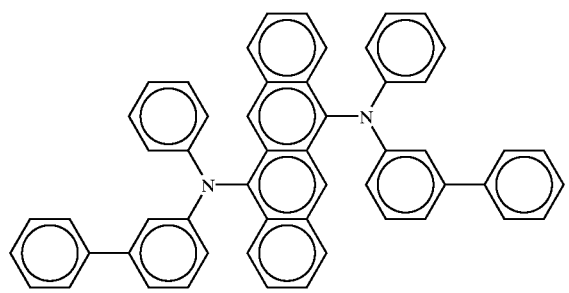
(76)
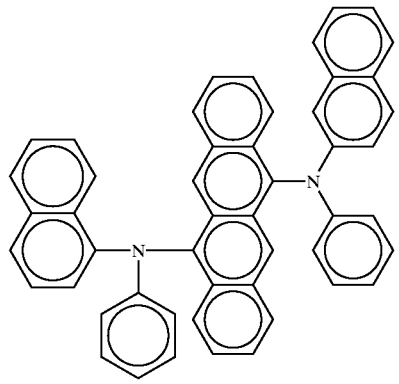
(77)
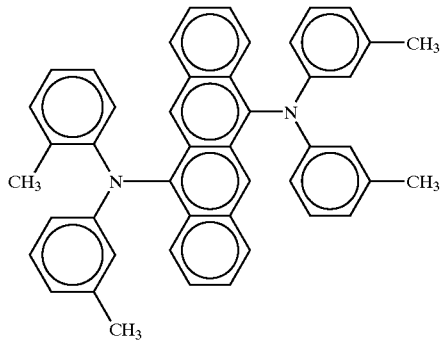
(78)
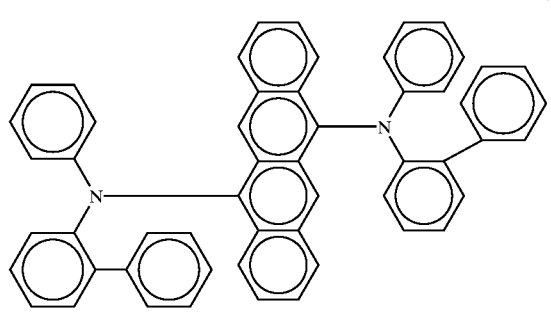
(79)
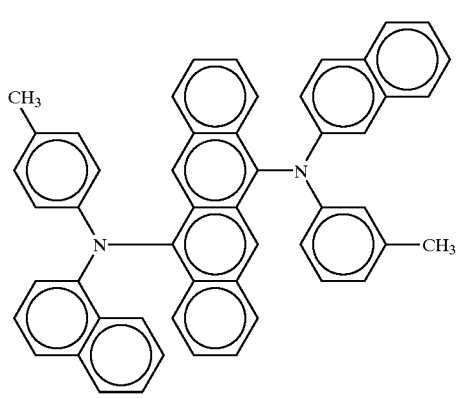
(80)

-continued
(81)
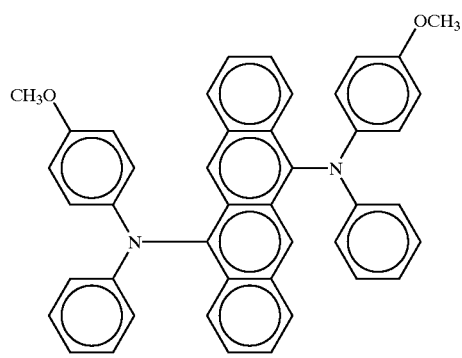
(82)
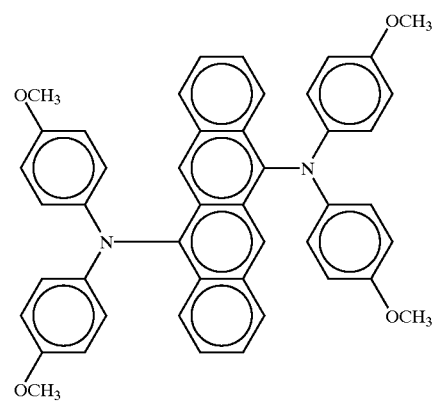
(83)
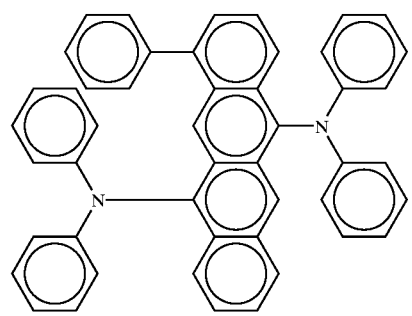
(84)
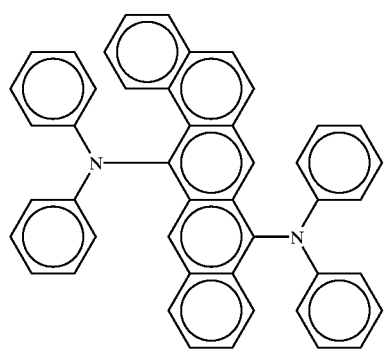
(85)
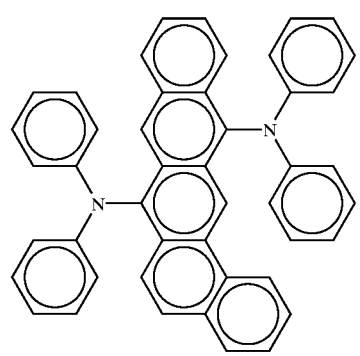
(86)
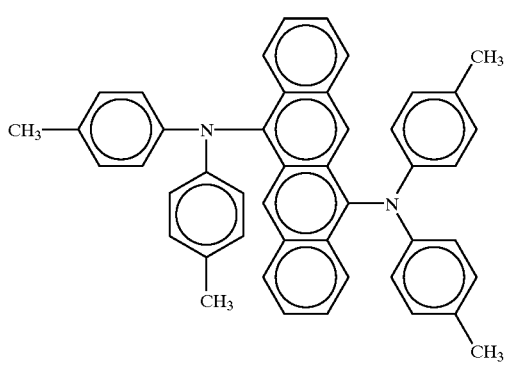

(87)
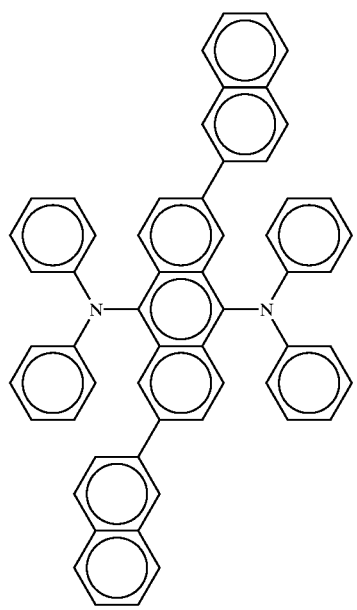
(88)
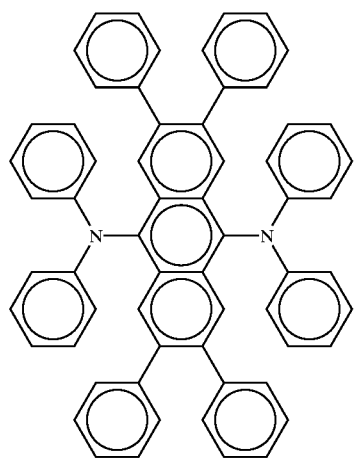
(89)
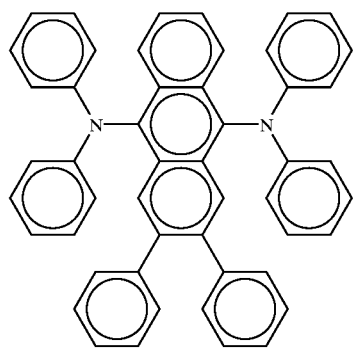
(90)
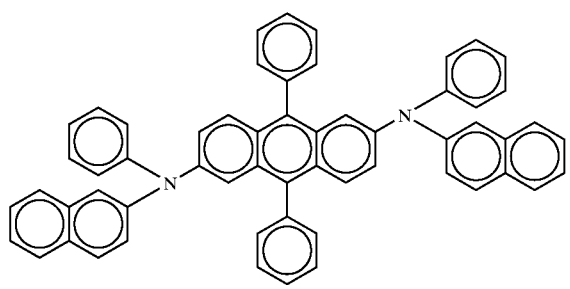
(91)
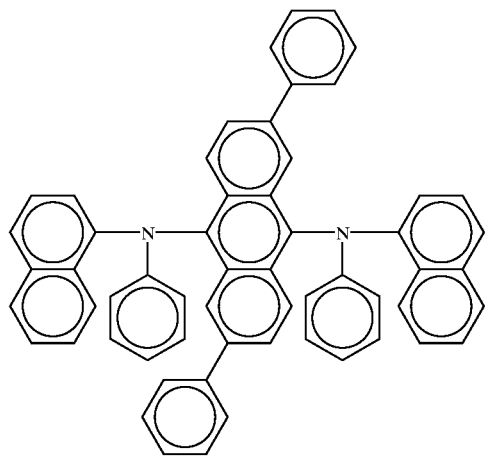
(92)
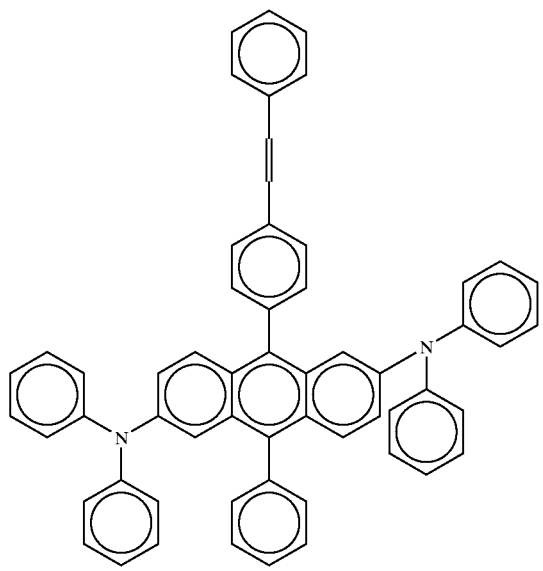

-continued
(93)
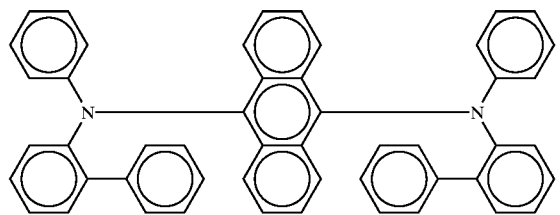
(94)
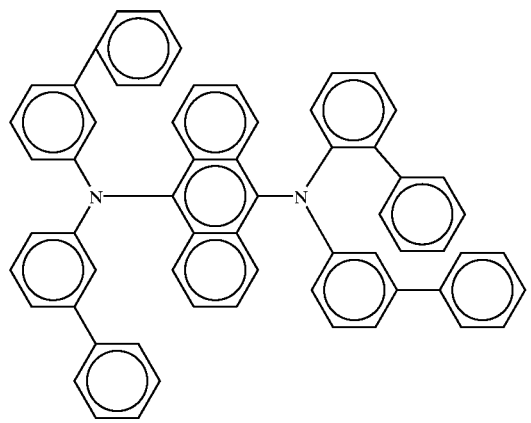
(95)
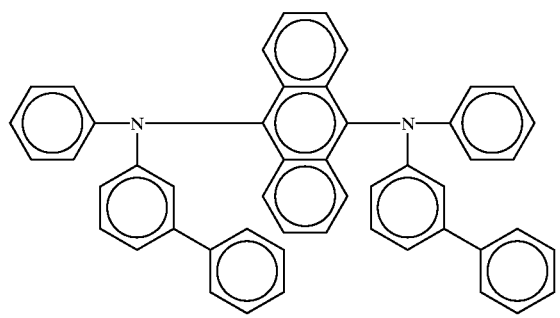
(96)
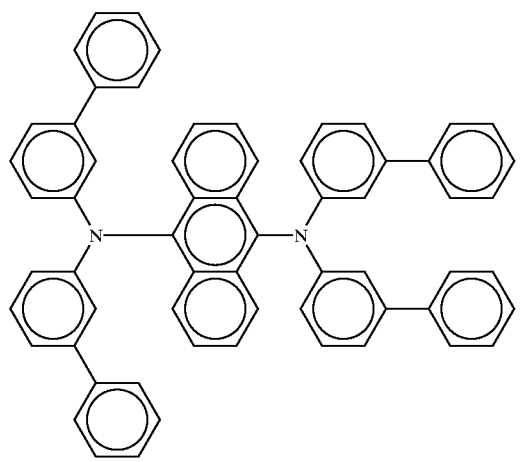
(97)
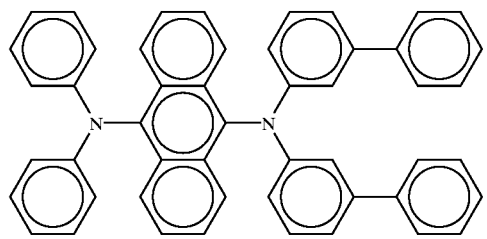
(98)
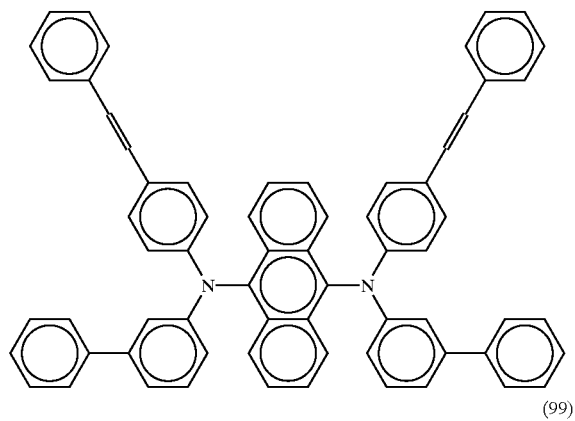
(99)
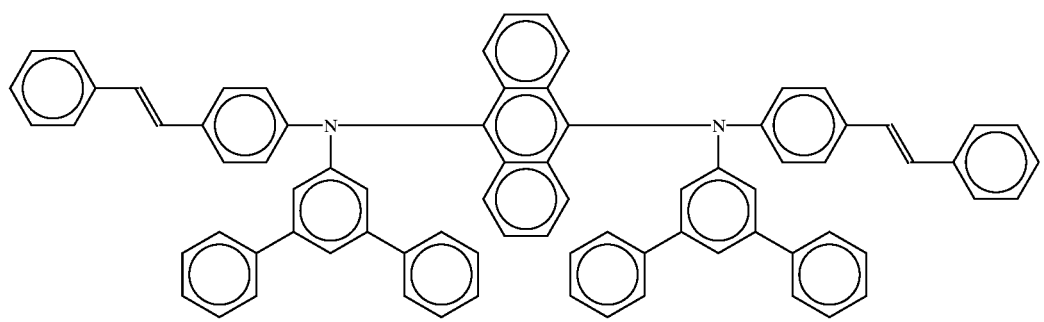

-continued
(100)
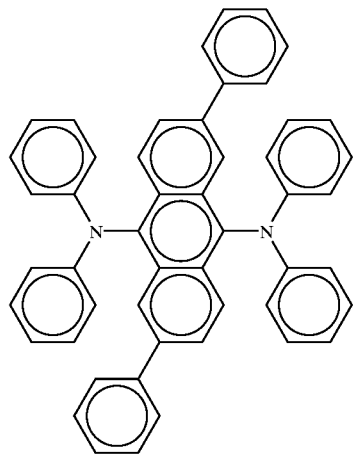
(101)
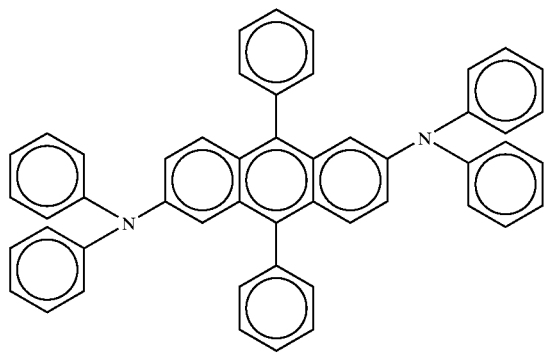
(102)
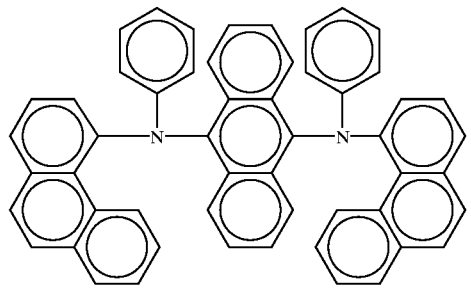
(103)
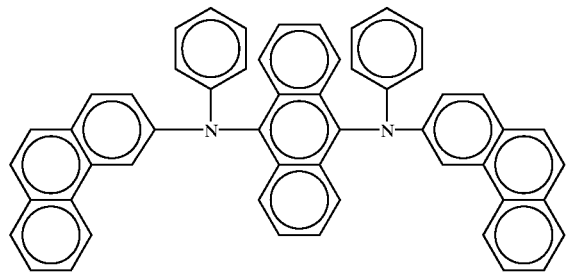
(104)
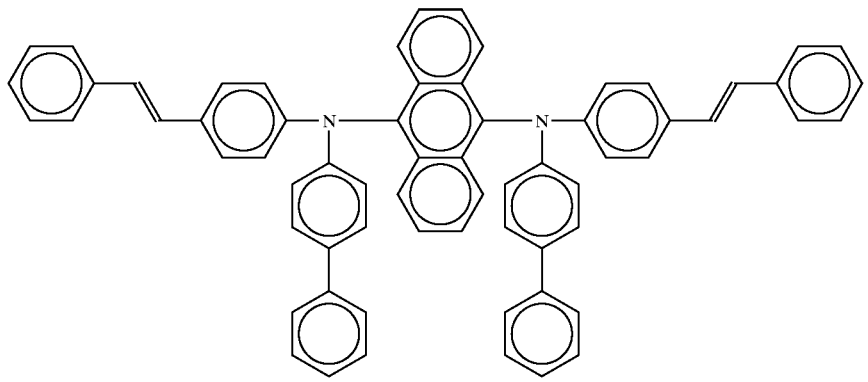
(105)
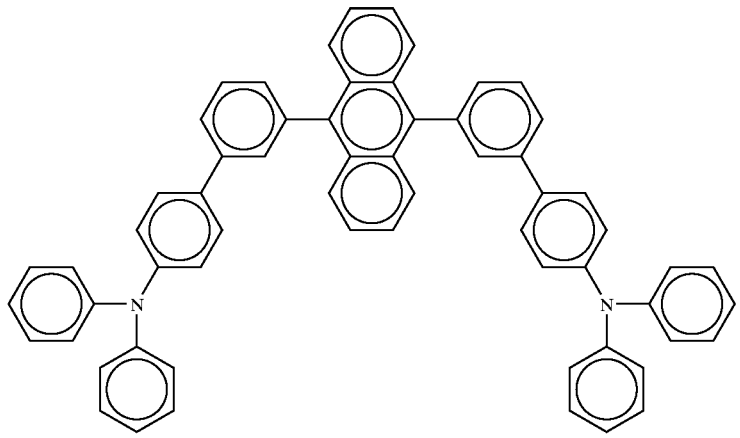

(106)
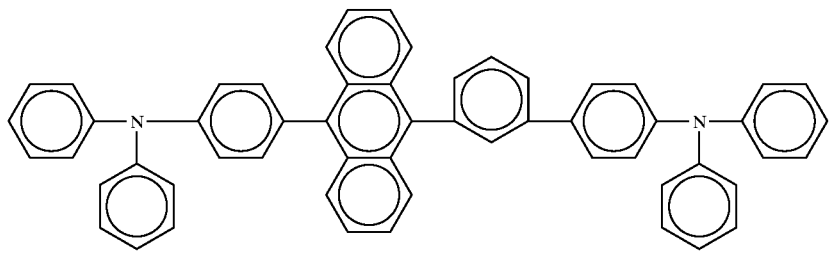
(107)
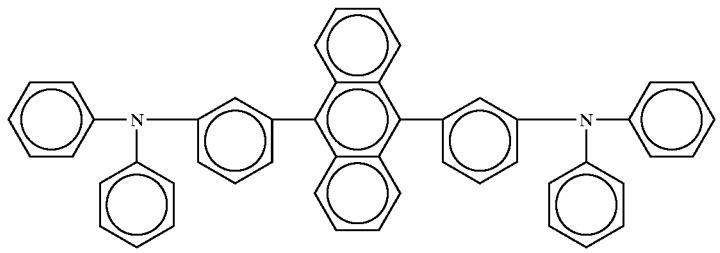
(108)
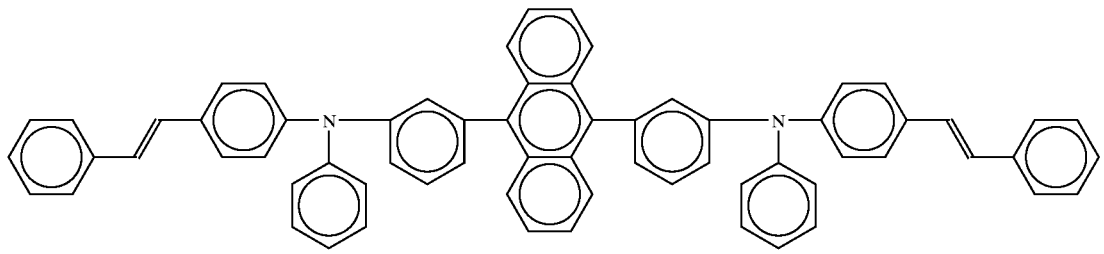
(109)
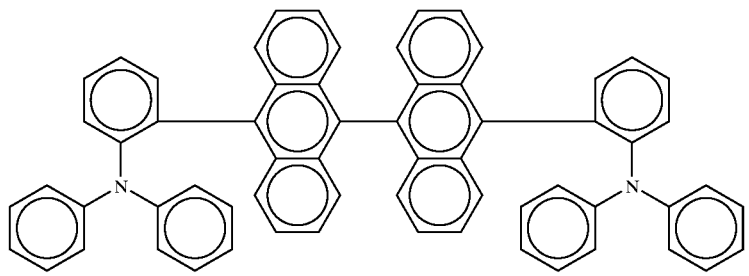
(110)
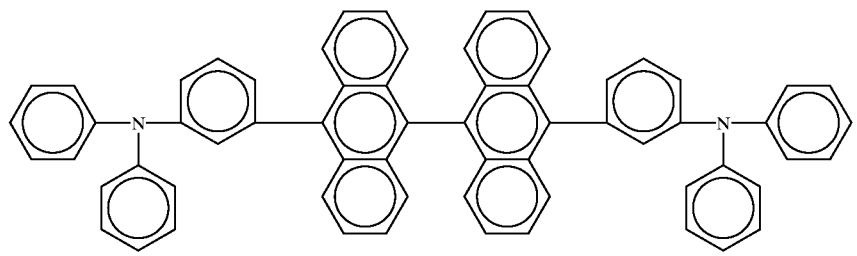
(111)
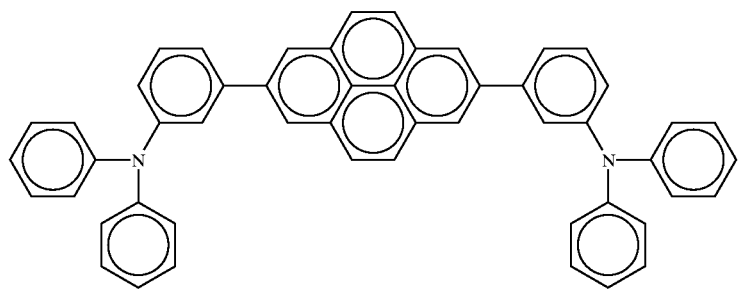

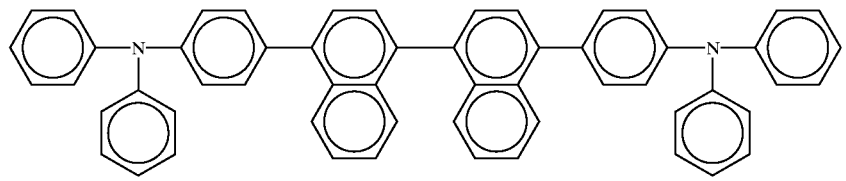
(112)
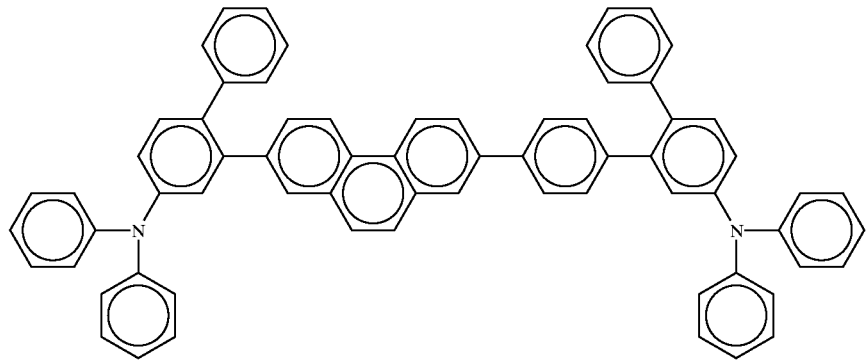
(113)
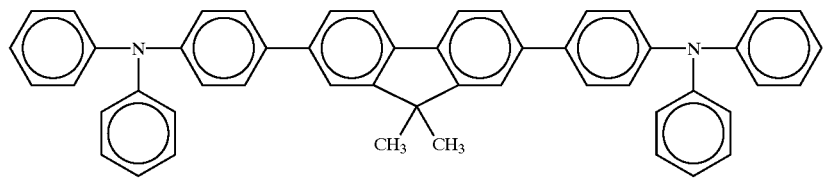
(114)
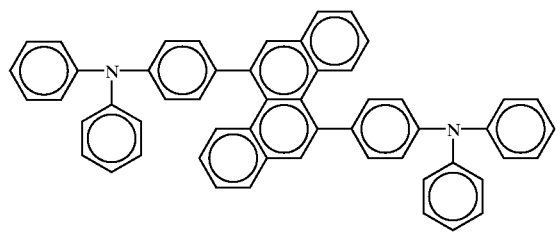
(115)
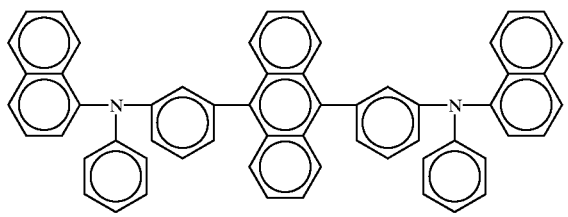
(116)
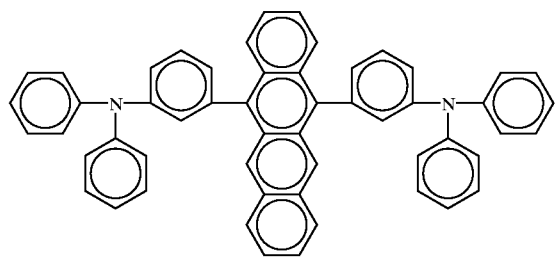
(117)
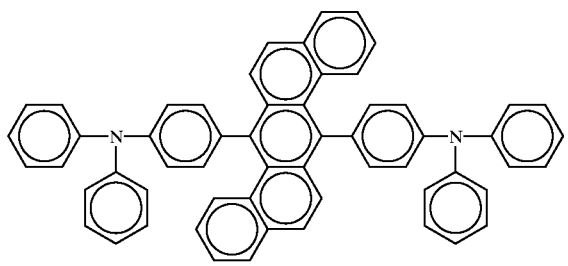
(118)
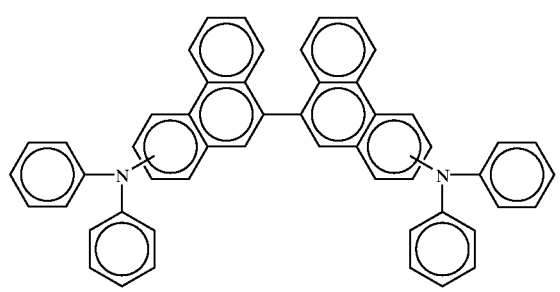
(119)
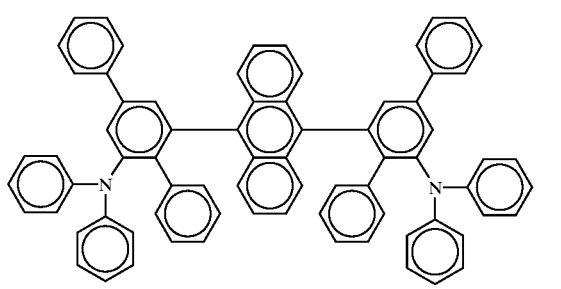
(120)

-continued
(121)
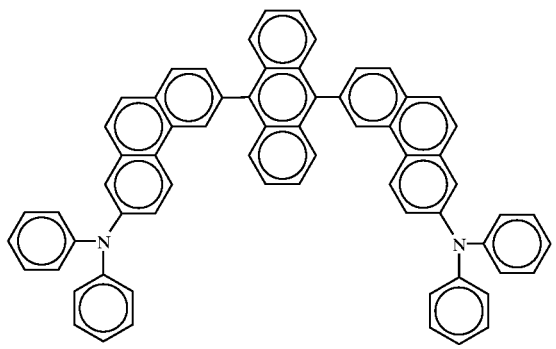
(122)
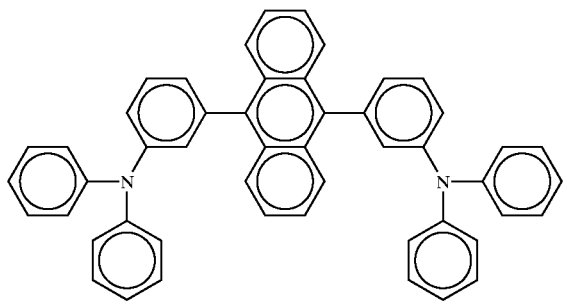
(123)
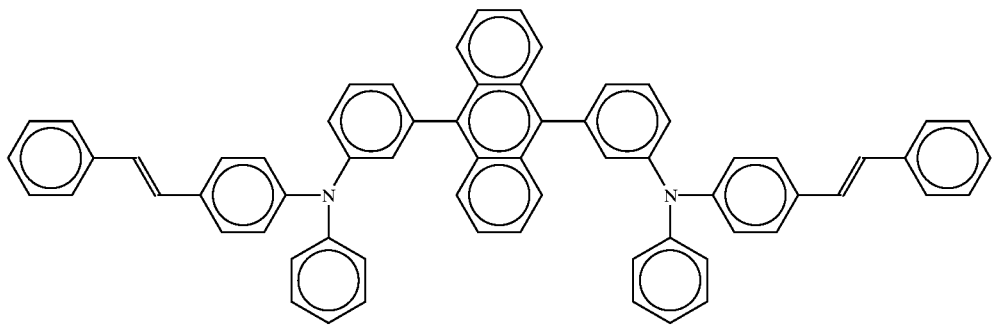
(124)
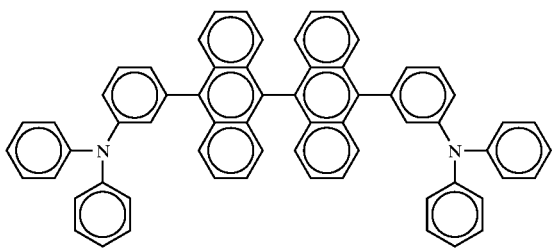
(125)
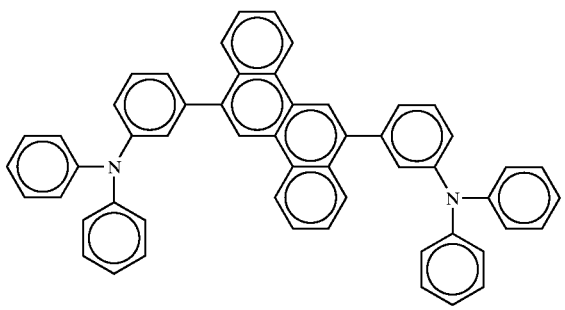
(126)
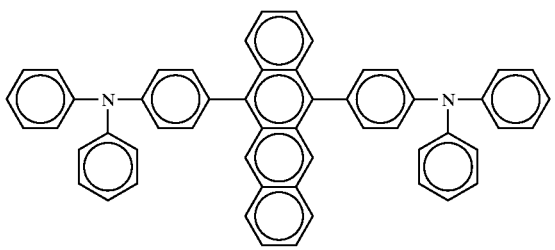

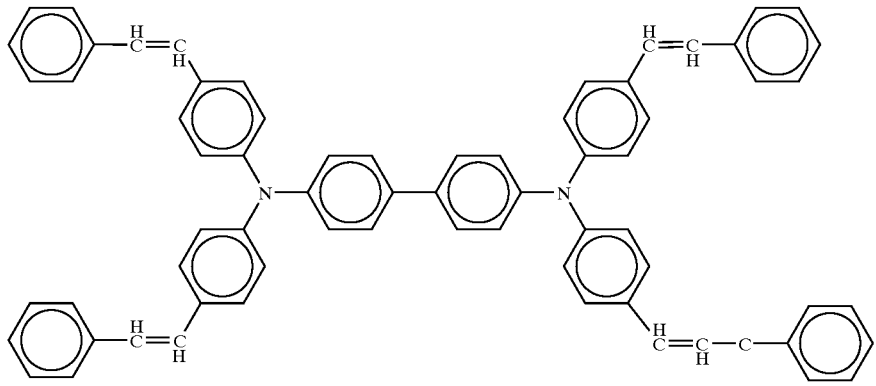
(127)
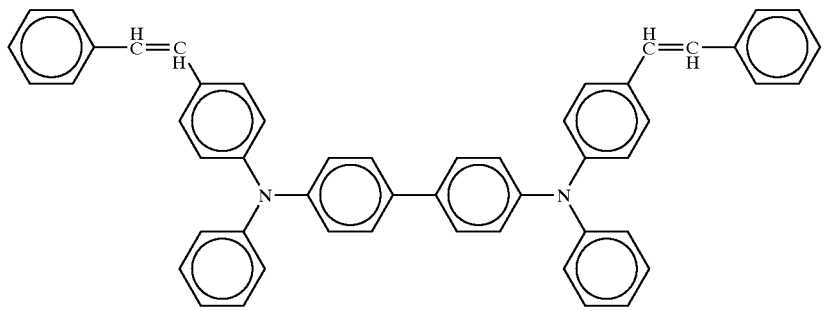
(128)
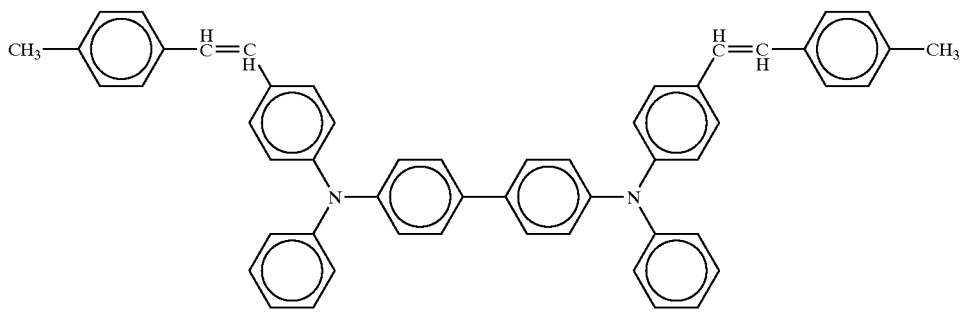
(129)
compound b
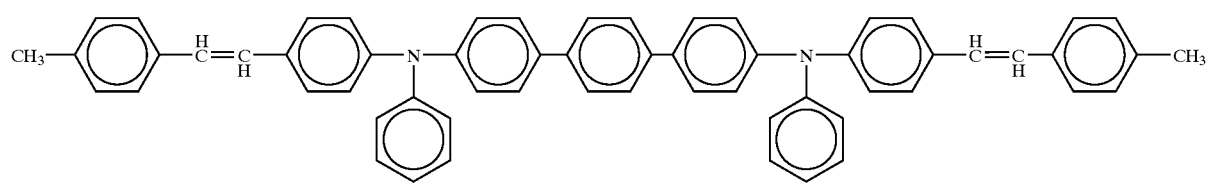
(130)
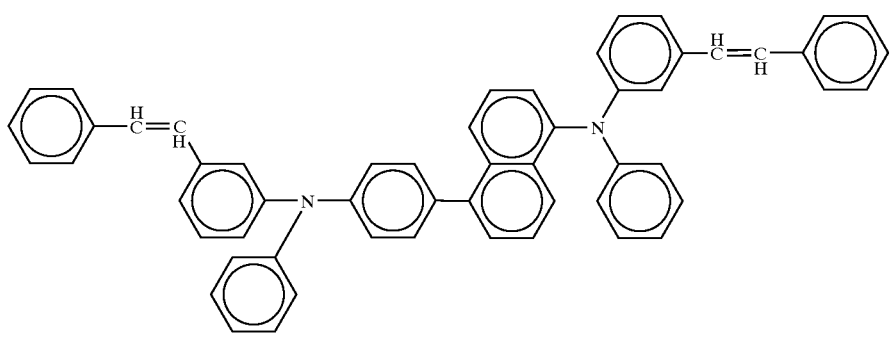
(131)

-continued
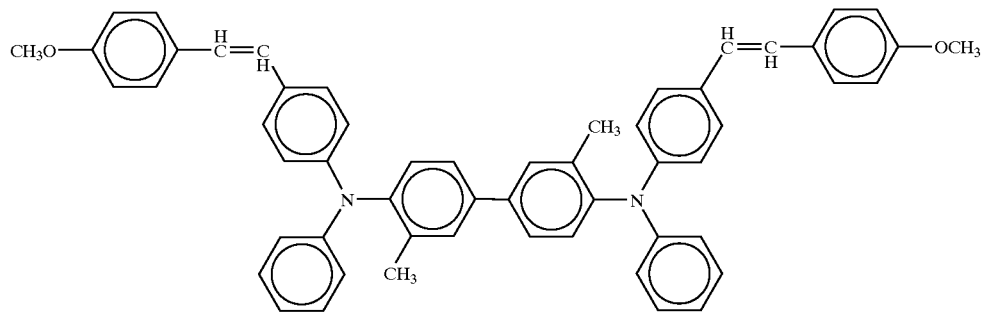
(132)
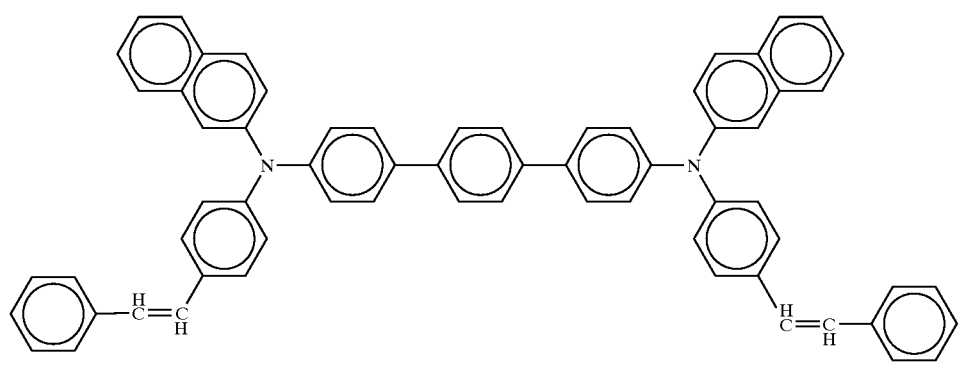
(133)
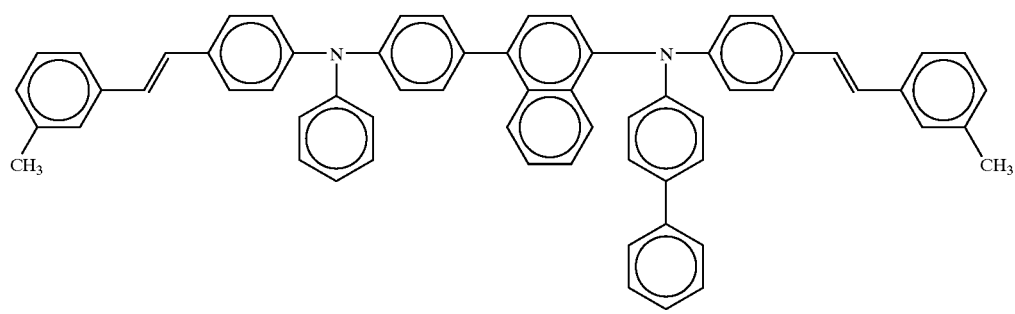
(134)
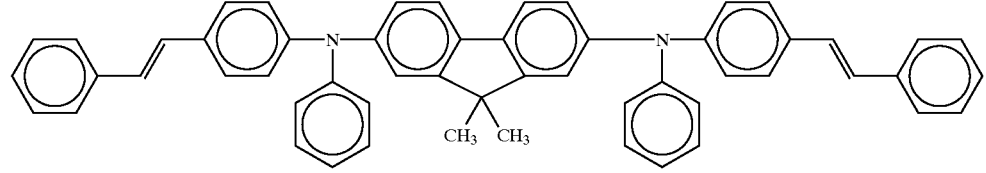
(135)
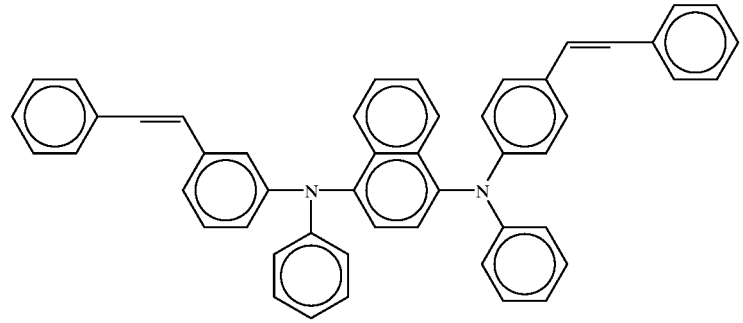
(136)
compound c (137)

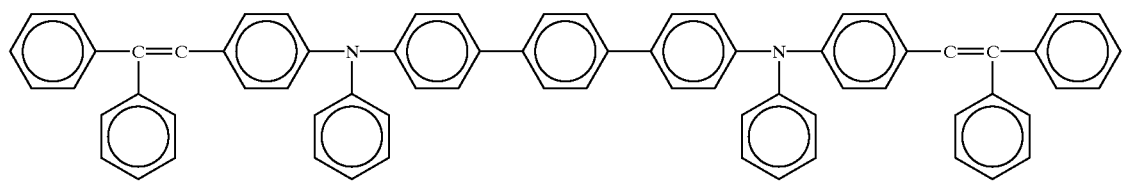

(138)

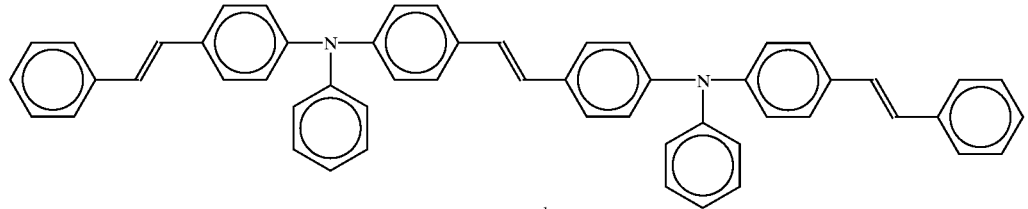

compound a (139)

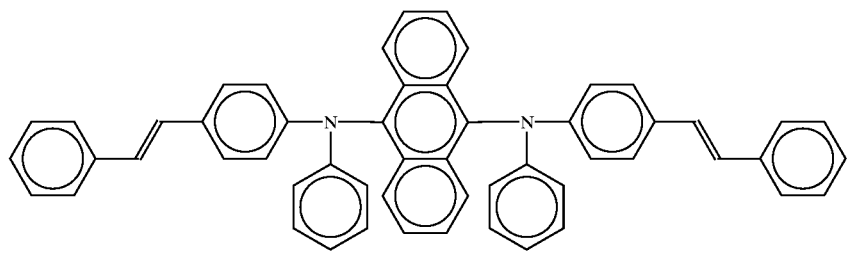

compound d (140)

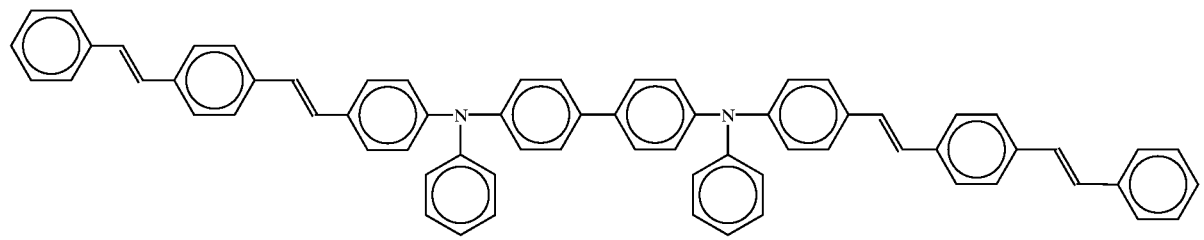

compound e (141)

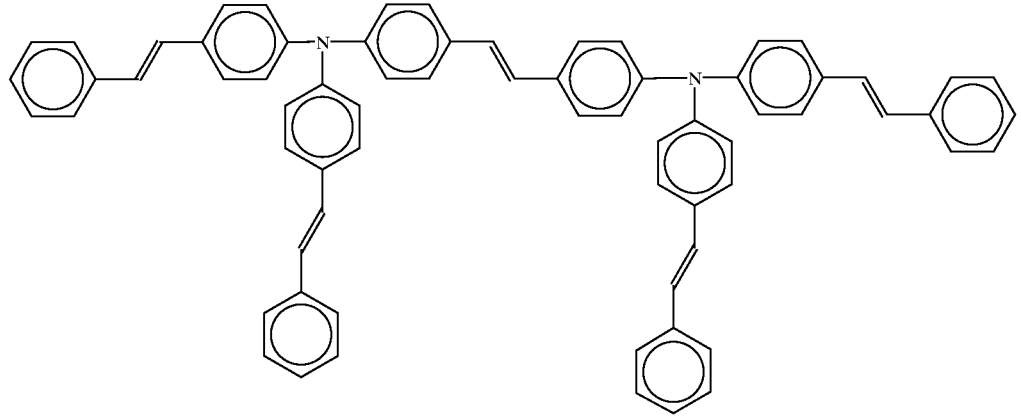

compound f

The compounds represented by general formulae [1], [3] to [10] of the present invention exhibit strong fluorescence in the solid state, have the excellent light emitting property in the electric field and show a quantum efficiency of fluorescence emission of 0.3 or greater since the polyphenyl structure represented by A or B and the amine structure are connected to each other at the center of the compounds. The compounds represented by general formulae [7] and [8] exhibit strong fluorescence in the solid state or the dispersed state in the fluorescence region of yellow color, orange color or red color and have an excellent light emitting property in the electric field since the structure containing the tetracene nucleus or the pentacene nucleus and the amine structure are connected to each other.

The compounds represented by general formulae [1], [3] to [10] of the present invention can be used effectively as the light emitting material and may be used also as the hole transporting material, the electron transporting material and the doping material since the compounds have all of the hole injecting property from metal electrodes or organic thin film layers, the hole transporting property, the electron injecting property from metal electrodes or organic thin film layers and the electron transporting property. In particular, when the compounds represented by general formula [7] and [8] are used as the doping material, highly efficient emission of red light can be achieved since the compounds works as the center of recombination of electrons and holes.

The compound represented by general formula [8] exhibits a particularly excellent property since the arylamine and tetracene are bonded at the specific positions.

The organic EL device of the present invention is a device in which one or a plurality of organic thin films are disposed between an anode and a cathode. When the device has a single layer, a light emitting layer is disposed between an anode and a cathode. The light emitting layer contains a light emitting material and may also contain a hole injecting material or a electron injecting material to transport holes injected at the anode or electrons injected at the cathode to the light emitting material. However, it is possible that the light emitting layer is formed with the light emitting material of the present invention alone because the light emitting material of the present invention has a very high quantum efficiency of fluorescence emission, excellent ability to transfer holes and excellent ability to transfer electrons and a uniform thin film can be formed. The organic EL device of the present invention having a multi-layer structure has a laminate structure such as: (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode). Since the compounds represented by general formulae [1], [3] to [11], [11'] and [17] have the excellent light emitting property and, moreover, the excellent hole injecting property, hole transporting property, electron injecting property and electron transporting property, the compounds can be used for the light emitting layer as the light emitting material.

In the light emitting layer, where necessary, conventional light emitting materials, doping materials, hole injecting materials and electron injecting materials may be used in addition to the compounds represented by general formulae [1], [3] to [11], [11'] and [17] of the present invention. Deterioration in luminance and life caused by quenching can be prevented by the multi-layer structure of the organic EL. Where necessary, a light emitting materials, a doping materials, a hole injecting materials and an electron injecting materials may be used in combination. By using a doping material, luminance and the efficiency of light emission can be improved and blue light and red light can be emitted. The hole injecting layer, the light emitting layer and the electron injecting layer may each have a multi-layer structure having two or more layers. When the hole injecting layer has a multi-layer structure, the layer into which holes are injected from the electrode is referred to as the hole injecting layer and the layer which receives holes from the hole injecting layer and transports holes from the hole injecting layer to the light emitting layer is referred to as the hole transporting layer. When the electron injecting layer has a multi-layer structure, the layer into which electrons are injected from the electrode is referred to as the electron injecting layer and the layer which receives electrons from the electron injecting layer and transports electrons from the electron injecting layer to the light emitting layer is referred to as the electron transporting layer. These layers are each selected and used in accordance with factors such as the energy level and heat resistance of the material and adhesion with the organic layers or the metal electrodes.

Examples of the material which can be used in the light emitting layer as the light emitting material or the doping material in combination with the compounds represented by general formulae [1], [3] to [11], [11'] and [17] include anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetraphenylbutadiene, coumarine, oxadiazole, aldazine, bisbenzoxazoline, bisstyryl, pyrazine, cyclopentadiene, metal complexes of quinoline, metal complexes of aminoquinoline, metal complexes of benzoquinoline, imines, diphenylethylene, vinylanthracene, diaminocarbazole, pyrane, thiopyrane, polymethine, merocyanine, oxinoid compounds chelated with imidazoles, quinacridone, rubrene, stilbene derivatives and fluorescent dyes. However, the examples of the above material are not limited to the above compounds.

In particular, metal complexes of quinoline and stilbene derivatives can be used in combination with the compounds represented by general formulae [7] and [8] as the light emitting material or the doping material in the light emitting layer.

It is essential that the content of the doping material in the light emitting layer is greater than the content of the compound represented by general formula [11] or [11']. It is preferable that the content is 80 to 99.9% by weight.

As the hole injecting material, a compound which has the ability to transfer holes, exhibits excellent effect of hole injection from the anode and excellent effect of hole injection to the light emitting layer or the light emitting material, prevents transfer of excited components formed in the light emitting layer into the electron injecting layer or the electron injecting material and has an excellent ability to form a thin film is preferable. Examples of such a compound include phthalocyanine derivatives, naphthalocyanine derivatives, porphyrin derivatives, oxaozole, oxadiazole, triazole, imidazole, imdazolone, imdazolethione, pyrazoline, pyrazolone, tetrahydroimidazole, oxazole, oxadiazole, hydrazone, acylhydrazone, polyarylalkanes, stilbene, butadiene, benzidine-type triphenylamine, styrylamine type triphenylamine, diamine type triphenylamine, derivatives of these compounds and macromolecular compounds such as polyvinylcarbazole, polysilane and conductive macromolecules. However, examples of such a compound are not limited to the compounds described above.

Among the hole injection materials which can be used in the organic EL device of the present invention, more effective hole injecting materials are aromatic tertiary amine derivatives and phthalocyanine derivatives.

Examples of the aromatic tertiary amine derivative include triphenylamine, tritolylamine, tolyldiphenylamine, N,N'-diphenyl-N,N'-(3-methylphenyl)-1,1'-biphenyl-4,4'-diamine, N,N,N,N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl) phenanthrene-9,10-diamine, N,N-bis(4-di-4-tolylaminophenyl)-4-phenylcyclohexane and oligomers and polymers having a skeleton structure of these aromatic tertiary amines. However, examples of the aromatic tertiary amine derivative are not limited to the above compounds.

Examples of the phthalocyanine (Pc) derivative include $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O-GaPc and corresponding derivatives of naphthalocyanine. However, examples of the derivatives of phthalocyanine and naphthalocyanine are not limited to the above compounds.

As the electron injecting material, a compound which has the ability to transport electrons, exhibits excellent effect of electron injection from the cathode and excellent effect of electron injecting to the light emitting layer or the light emitting material, prevents transfer of excited components formed in the light emitting layer into the hole injecting layer or the hole injecting material and has an excellent ability to form a thin film is preferable. Examples of such a compound include fluorenone, anthraquinodimethane, diphenoquinone, thiopyrane dioxide, oxazole, oxadiazole, triazole, imidazole, peryleneteteracarboxylic acid, fluorenylidenemethane, anthraquinodimethane, anthrone and derivatives of these compounds. However, examples of such a compound is not limited to the compounds described above. The electron injecting property can be improved by adding an electron accepting material to the hole injecting material or an electron donating material to the electron injecting material.

In the organic EL device of the present invention, more effective electron injecting materials are metal complex compounds and five-membered derivatives containing nitrogen.

Examples of the metal complex compound include 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinilinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum and bis(2-methyl-8-quinolinato)(2-naphtholato)gallium. However, examples of the metal complex compound are not limited to the above compounds.

Preferable examples of the five-membered derivative containing nitrogen include derivatives of oxazoles, thiazoles, thiadiazoles and triazoles. Specific examples include 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1, 3,4-thiadiazole, 2, 5-bis(1-naphthyl)-1,3,4-thiadiazole, 1,4-bis[2-(5-phenylthiadiazolyl)]benzene, 2-(4'tert-butylphenyl)-5-(4"-biphenyl)-1,3,4-triazole, 2,5-bis(1-naphthyl)-1,3,4-triazole and 1,4-bis[2-(5-phenyltriazolyl)]benzene. However, examples of the five-membered derivative containing nitrogen are not limited to the above compounds.

In the organic EL device of the present invention, at least one of light emitting materials, doping materials, hole injecting materials and electron injecting materials may be contained in the same layer of the light emitting layer in addition to the compounds represented by general formulae [1] and [3] to [8]. In order to improve stability of the organic EL device of the present invention with respect to the temperature, the humidity and the oxygen, a protecting layer may be formed on the entire surface of the device or the entire device may be protected with silicon oil or a resin.

As the conductive material used as the anode of the organic EL device, a material having a work function of 4 eV or greater is suitable. Examples of such a material include carbon, aluminum, vanadium, iron, cobalt, nickel, tungsten, silver, gold, platinum, palladium, alloys of these metals, metal oxides used for ITO substrates and NESA substrates such as tin oxide and indium oxide and organic conductive resins such as polythiophene and polypyrrol. As the conductive material used for the cathode, a material having a work function smaller than 4 eV is suitable. Examples of such a material include magnesium, calcium, tin, lead, titanium, yttrium, lithium, ruthenium, manganese, aluminum and alloys of these metals. However, examples of the materials used for the anode and the cathode are not limited to the above examples. Typical examples of the alloy include alloys of magnesium and silver, alloys of magnesium and indium and alloys of lithium and aluminum. However, examples of the alloy are not limited to these alloys. The composition of the alloy is determined by the temperature of the source of vapor deposition, the atmosphere and the degree of vacuum and a suitable composition is selected. The anode and the cathode may have a multi-layer structure having two or more layers, where necessary.

In the organic EL device, it is preferable that at least one face of the device is sufficiently transparent in the wave length region of emitted light to achieve efficient light emission. It is preferable that the substrate is also transparent. In the preparation of the transparent electrode, the above conductive material is used and vapor deposition or sputtering is conducted so that the prescribed transparency is surly obtained. It is preferable that the electrode disposed on the light emitting face has a light transmittance of 10% or greater. The substrate is not particularly limited as long as the substrate has mechanical strength and strength at high temperatures and is transparent. Glass substrates or transparent films of resins may be used. Example of the transparent films of resins include films of polyethylene, ethylene-vinyl acetate copolymers, ethylene-vinyl alcohol copolymers, polypropylene, polystyrene, polymethyl methacrylate, polyvinyl chloride, polyvinyl alcohol, polyvinyl butyral, nylon, polyether ether ketones, polsulfones, polyether sulfones, tetrafluoroethylene-perfluoroalkyl vinyl ether copolymers, polyvinyl fluoride, tetrafluoro-ethylene-ethylene copolymers, tetrafluoroethylene-hexafluoropropylene copolymers, polychlorotrifluoroethylene, polyvinylidene fluoride, polyesters, polycarbonates, polyurethanes, polyimides, polyether imides, polyimides and polypropylene.

Each layer of the organic EL device of the present invention can be produced suitably in accordance with a dry process of film formation such as vacuum vapor deposition, sputtering and plasma and ion plating or a wet process of film formation such as spin coating, dipping and flow coating. The thickness of the film is not particularly limited. However, it is necessary that the thickness be set at a suitable value. When the thickness is greater than the suitable value, a great voltage must be applied to obtain a prescribed output of light and the efficiency deteriorates. when the thickness is smaller than the suitable value, pin holes are formed and a sufficient luminance cannot be obtained even when the electric field is applied. In general, the suitable range of the thickness is 5 $\mu$m to 10 $\mu$m. A thickness in the range of 10 nm to 0.2 $\mu$m is preferable.

When the device is produced in accordance with a wet process, materials forming each layer are dissolved or dispersed in a suitable solvent such as ethanol, chloroform, tetrahydrofuran and dioxane and a film is formed from the solution or the suspension. The solvent is not particularly limited. In any organic thin layer, suitable resins and additives may be used to improve the property to form a film and to prevent formation of pin holes. Examples of the resin which can be used include insulating resins such as polystyrene, polycarbonates, polyarylates, polyesters, polyamides, polyurethanes, polysulfones, polymethyl methacrylate, polymethyl acrylate and cellulose, copolymers derived from these resins, photoconductive resins such as poly-N-vinylcarbazole and polysilane and conductive resins such as polythiophene and polypyrrol. Examples of the additive include antioxidants, ultraviolet light absorbents and plasticizers.

As described above, by using the compounds of the present invention for the light emitting layer of the organic EL device, practically sufficient luminance can be obtained under application of a low voltage. Therefore, the organic EL device exhibiting a high efficiency of light emission and having a long life due to suppressed degradation and excellent heat resistance can be obtained.

The organic EL device of the present invention can be used for a planar light emitting member such as a flat panel display of wall televisions, a back light for copiers, printers and liquid crystal displays, a light source of instruments, display panels and a marker light.

The materials of the present invention can be used not only for the organic EL devices but also in the field of electronic photosensitive materials, opto-electric conversion devices, solar batteries and image sensors.

Examples of the primary amine represented by general formula [15] which is used in the process for producing a material for organic EL devices of the present invention include primary alkylamines such as methylamine, ethylamine, n-propylamine, isopropylamine, n-butylamine, isobutylamine, sec-butylamine, tert-butylamine, n-amylamine, isoamylamine, tert-amylamine, cyclohexylamine, n-hexylamine, heptylamine, 2-aminoheptane, 3-aminoheptane, octylamine, nonylamine, decylamine, undecylamine, dodecylamine, tridecylamine, 1-tetradecylamine, pentadecylamine, 1-hexadecylamine and octadecylamine; primary alkyldiamines such as ethylenediamine, 1,2-diaminopropane, 1,3-diaminopropane and 1,4-diaminobutane; arylamines such as aniline, o-fluoroaniline, m-fluoroaniline, p-fluoroaniline, o-toluidine, m-toluidine, p-toluidine, o-anisidine, m-anisidine, p-anisidine, 1-naphthylamine, 2-naphthylamine, 1-aminoanthracene, 2-aminoanthracene, 2-aminobiphenyl, 4-aminobiphenyl, 9-aminophenanthrene, 2-trifluoromethyltoluidine, 3-trifluoromethyltoluidine and 4-trifluoromethyltoluidine; aryldiamines such as o-phenylenediamine, m-phenylenediamine, p-phenylenediamine, fluorenediamine and 1,8-naphthalenediamine; and the following compounds:

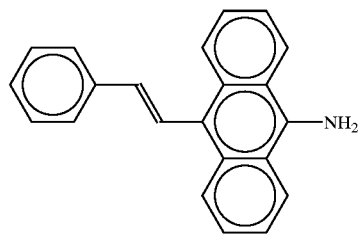

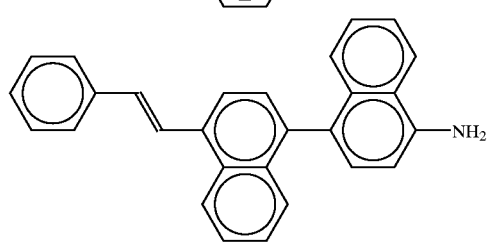

-continued

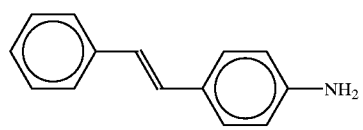

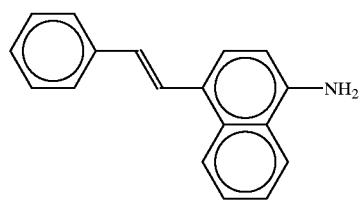

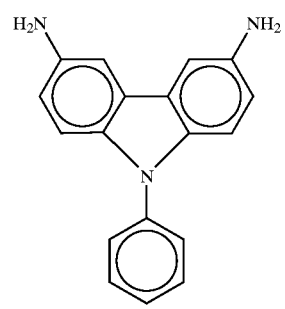

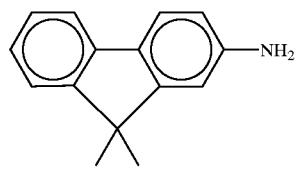

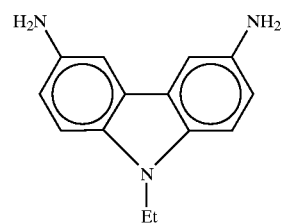

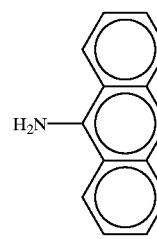

Examples of the secondary amine represented by general formula [15] include the following compounds:

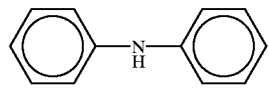
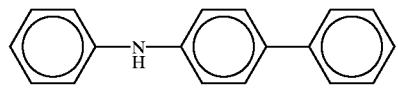
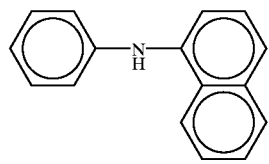
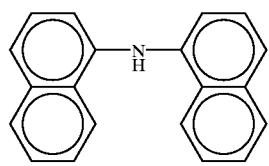
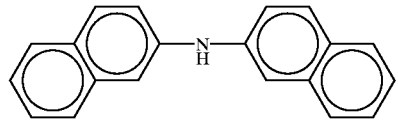
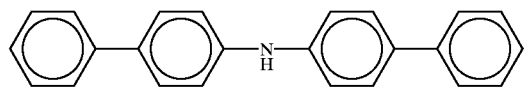
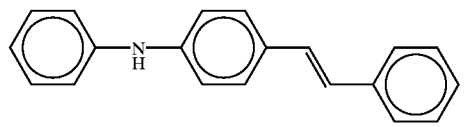
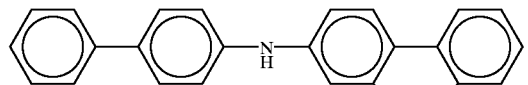
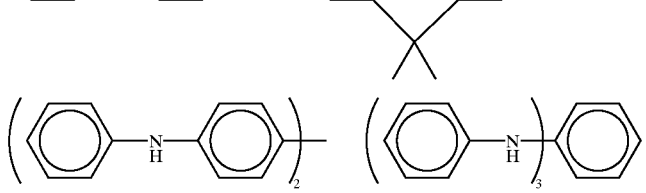
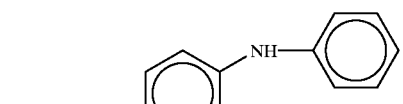
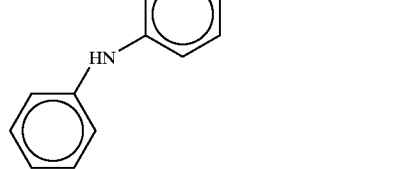

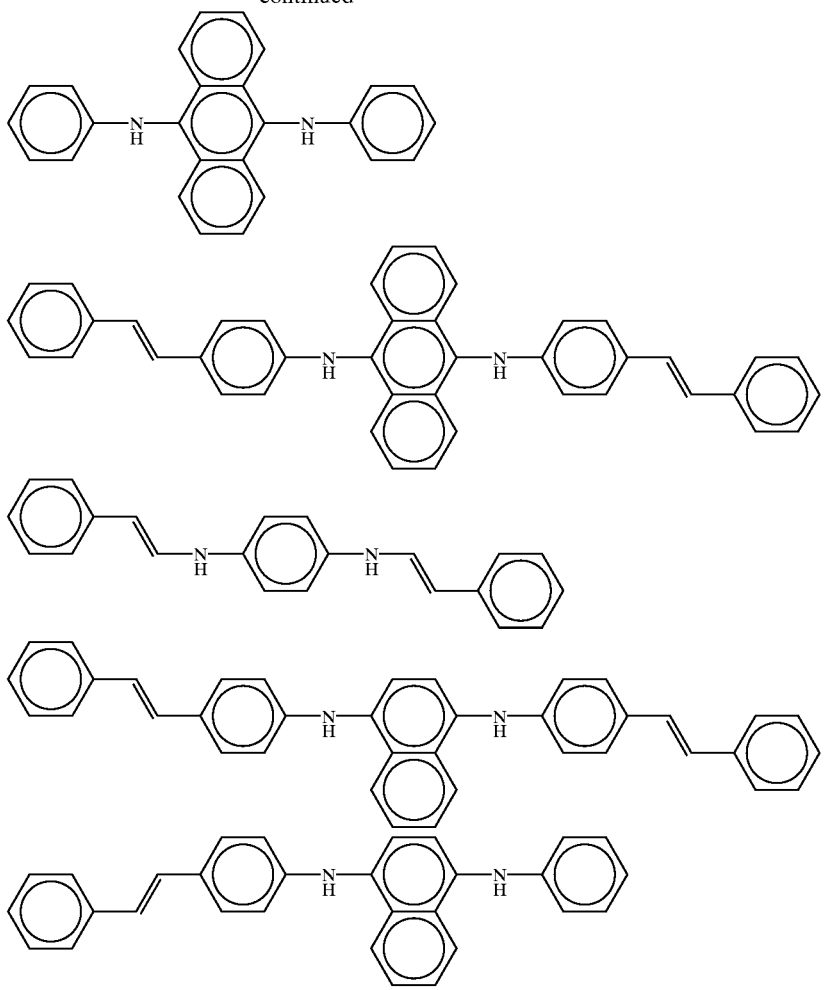

The aryl halide represented by general formula [16] is not particularly limited. The group represented by Ar is, in general, an alkyl group having 1 to 18 carbon atoms or a substituted or unsubstituted aryl group having 6 to 22 carbon atoms. The aromatic ring may have substituents. In the present invention, the aryl group include hydrocarbon groups having condensed rings.

Examples of the aryl halide include aryl bromides such as bromobenzene, o-bromoanisole, m-bromoanisole, p-bromoanisole, o-bromotoluene, m-bromotoluene, p-bromotoluene, o-bromophenol, m-bromophenol, p-bromophenol, 2-bromobenzotrifluoride, 3-bromobenzotrifluoride, 4-b romobenzenetrifluoride, 1-bromo-2,4-dimethoxybenzene, 1-bromo-2,5-dimethoxybenzene, 2-bromophenetyl alcohol, 3-bromophenetyl alcohol, 4-bromophenetyl alcohol, 5-bromo-1,2,4-trimethylbenzene, 2-bromo-m-xylene, 2-bromo-p-xylene, 3-bromo-o-xylene, 4-bromo-o-xylene, 4-bromo-m-xylene, 5-bromo-m-xylene, 1-bromo-3-(trifluoromethoxy)benzene, 1-bromo-4-(trifluoromethoxy)benzene, 2-bromobiphenyl, 3-bromobiphenyl, 4-bromobiphenyl, 4-bromo-1,2-(methylenedioxy)benzene, 1-bromonaphthalene, 2-bromonaphthalene, 1-bromo-2-methylnaphthalene and 1-bromo-4-methylnaphthalene; aryl chlorides such as chlorobenzene, o-chloroanisole, m-chloroanisole, p-chloroanisole, o-chlorotoluene, m-chlorotoluene, p-chlorotoluene, o-chlorophenol, m-chlorophenol, p-chlorophenol, 2-chlorobenzotrifluoride, 3-chlorobenzotrifluoride, 4-chlorobenzenetrifluoride, 1-chloro-2,4-dimethoxybenzene, 1-chloro-2,5-dimethoxybenzene, 2-chlorophenetyl alcohol, 3-chlorophenetyl alcohol, 4-chlorophenetyl alcohol, 5-chloro-1,2,4-trimethylbenzene, 2-chloro-m-xylene, 2-chloro-p-xylene, 3-chloro-o-xylene, 4-chloro-o-xylene, 4-chloro-m-xylene, 5-chloro-m-xylene, 1-chloro-3-(trifluoromethoxy)benzene, 1-chloro-4-(trifluoromethoxy) benzene, 2-chlorobiphenyl, 3-chlorobiphenyl, 4-chlorobiphenyl, 1-chloronaphthalene, 2-chloronaphthalene, 1-chloro-2-methylnaphthalene and 1-chloro-4-methylnaphthalene; aryl iodides such as iodobenzene, o-iodoanisole, m-iodoanisole, p-iodoanisole, o-iodotoluene, m-iodotoluene, p-iodotoluene, o-iodophenol, m-iodophenol, p-iodophenol, 2-iodobenzotrifluoride, 3-iodobenzotrifluoride, 4-iodobenzenetrifluoride, 1-iodo-2,4-dimethoxybenzene, 1-iodo-2,5-dimethoxybenzene, 2-iodophenetyl alcohol, 3-iodophenetyl alcohol, 4-iodophenetyl alcohol, 5-iodo-1,2,4-trimethylbenzene, 2-iodo-m-xylene, 2-iodo-p-xylene, 3-iodo-o-xylene, 4-iodo-o-xylene, 4-iodo-m-xylene, 5-iodo-m-xylene, 1-iodo-3-(trifluoromethoxy)benzene, 1-iodo-4-(trifluoromethoxy) benzene, 2-iodobiphenyl, 3-iodobiphenyl, 4-iodobiphenyl, 1-iodonaphthalene, 2-iodonaphthalene, 1-iodo-2-methylnaphthalene and 1-iodo-4-methylnaphthalene; aryl fluorides such as fluorobenzene, o-fluoroanisole, m-fluoroanisole, p-fluoroanisole, o-fluorotoluene, m-fluorotoluene, p-fluorotoluene, o-fluorophenol, m-fluorophenol, p-fluorophenol, 2-fluorobenzotrifluoride, 3-fluorobenzotrifluoride, 4-fluorobenzenetrifluoride, 1-fluoro-2,4-dimethoxybenzene, 1-fluoro-2,5-dimethoxybenzene, 2-fluorophenetyl alcohol, 3-fluorophenetyl alcohol, 4-fluorophenetyl alcohol, 5-fluoro-1,2,4-trimethylbenzene, 2-fluoro-m-xylene, 2-fluoro-p-xylene, 3-fluoro-o-xylene, 4-fluoro-o-xylene, 4-fluoro-m-xylene, 5-fluoro-m-xylene, 1-fluoro-3-(trifluoromethoxy)benzene, 1-fluoro-4-(trifluoromethoxy)benzene, 2-fluorobiphenyl, 3-fluorobiphenyl, 4-fluorobiphenyl, 4-fluoro-1,2-(methylenedioxy)benzene, 1-fluoronaphthalene, 2-fluoronaphthalene, 1-fluoro-2-methylnaphthalene and 1-fluoro-4-methylnaphthalene; and the following compounds:

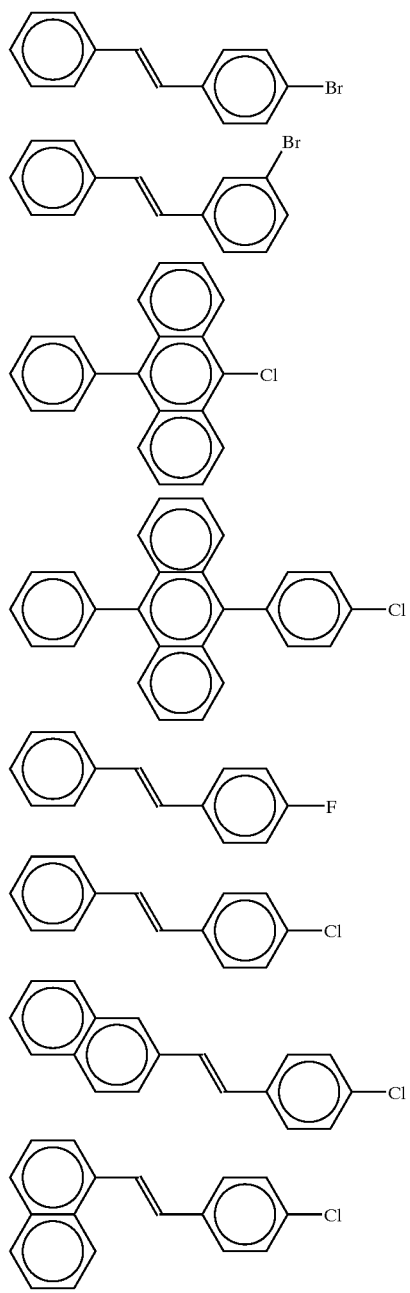

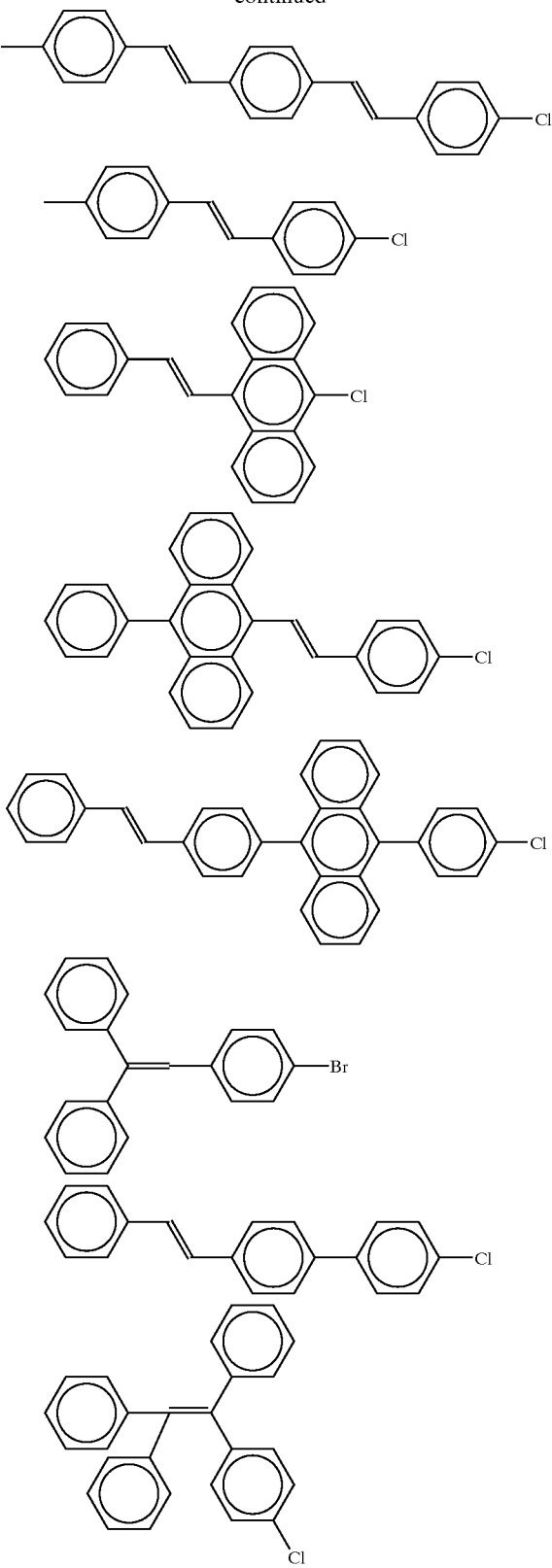

Aryl halides having 2 or more halogen atoms and preferably 2 or 3 halogen atoms can also be used as long as the object of the present invention is not adversely affected. Examples of the aryl halide having 2 or more halogen atoms include 1,2-dibromobenzene, 1,3-dibromobenzene, 1,4-dibromobenzene, 9,10-dibromoanthracene, 9,10-dichloroanthracene, 4,4'-dibromobiphenyl, 4,4'-dichlorobiphenyl, 4,4'-diiodobiphenyl, 1-bromo-2-fluorobenzene, 1-bromo-3-fluorobenzene, 1-bromo-4-fluorobenzene, 2-bromochlorobenzene, 3-bromochlorobenzene, 4-bromochlorobenzene, 2-bromo-5-chlorotoluene, 3-bromo-4-chlorobenzotrifluoride, 5-bromo-2-chlorobenzotrifluoride, 1-bromo-2,3-dichlorobenzene, 1-bromo-2,6-dichlorobenzene, 1-bromo-3,5-dichlorobenzene, 2-bromo-4-fluorotoluene, 2-bromo-5-fluorotoluene, 3-bromo-4-fluorotoluene, 4-bromo-2-fluorotoluene, 4-bromo-3-fluorotoluene, tris(4-bromophenyl)amine, 1,3,5-tribromobenzene and the following compounds:

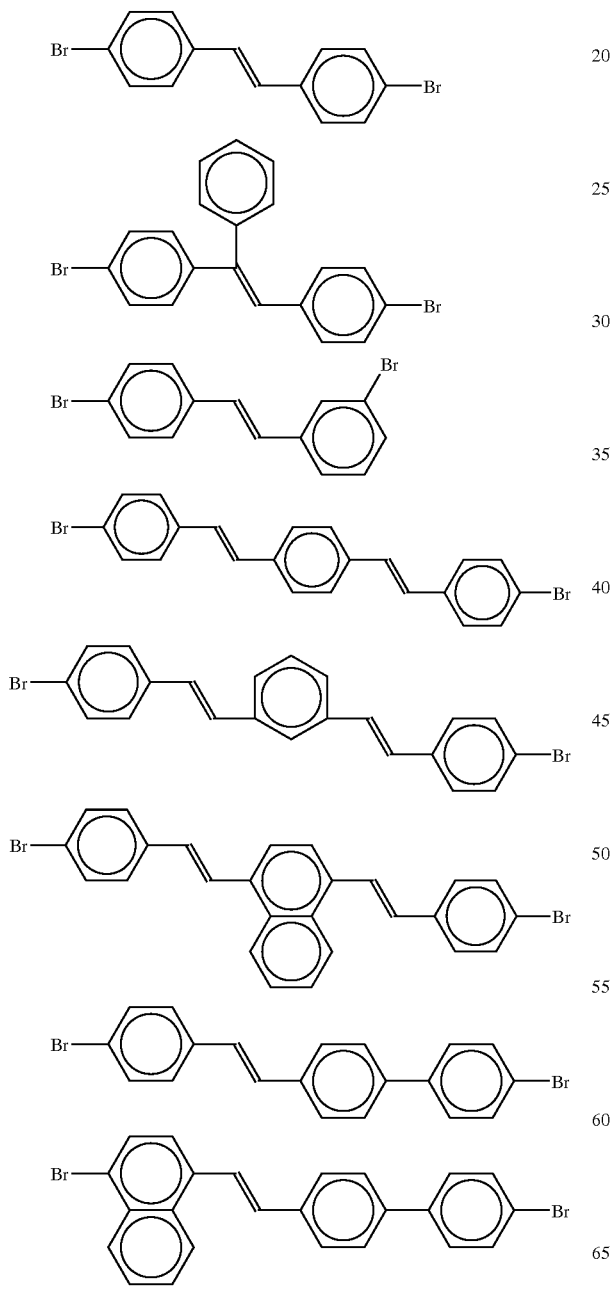

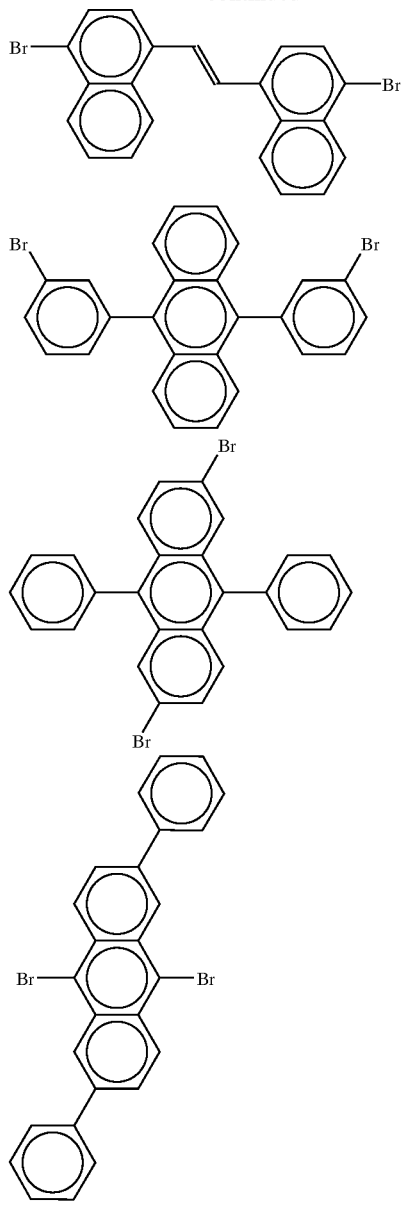

In the process for producing materials for organic EL devices of the present invention, the method of addition of the aryl halide is not particularly limited. For example, two different types of aryl halides may be mixed with a primary amine before starting the reaction and the reaction may be conducted using the obtained mixture. Alternatively, a primary amine may be reacted with one of two types of aryl halides. Then, the obtained secondary amine may be added to the other aryl halide and the reaction is conducted. The latter method in which different aryl halides are added successively is preferable because a tertiary amine can be produced more selectively.

The amount of the added aryl halide is not particularly limited. When the two types of aryl halides are added to the primary amine simultaneously, it is suitable that the amount of the aryl halide is in the range of 0.5 to 10 moles per 1 mole of the primary amine. From the standpoint of economy and easier treatments after the reaction such as separation of the unreacted aryl halide, it is preferable that the amount of the aryl halide is in the range of 0.7 to 5 moles per 1 mole of the primary amine. When the two types of aryl halides are added successively to the primary amine, the aryl halide which is added first is added to the reaction system in an amount in the range of 0.5 to 1.5 moles per 1 mole of the amino group in the primary amine. From the standpoint of improving the selectivity of the tertiary amine of the object compound, it is preferable that the above aryl halide is added to the reaction system in an amount of 0.9 to 1.1 mole per 1 mole of the amino group in the primary amine.

The aryl halide which is added after preparation of the secondary amine is added in an amount of 0.1 to 10 mole per 1 mole of the amino group in the primary amine used as the starting material. To prevent complicated operations in separation of the unreacted aryl halide and the unreacted secondary amine after the reaction, it is preferable that the aryl halide is added in an amount of 0.9 to 5 mole per 1 mole of the amino group in the primary amine used as the starting material.

The palladium compound used as the catalyst component in the present invention is not particularly limited as long as it is a compound of palladium. Examples of the palladium compound include compounds of tetravalent palladium such as sodium hexachloropalladate(IV) tetrahydrate and potassium hexachloropalladate(IV); compounds of divalent palladium such as palladium(II) chloride, palladium(II) bromide, palladium(II) acetate, palladium acetylacetonate (II), dichlorobis(benzonitrile)palladium(II), dichlorobis(acetonitrile)palladium(II), dichloro(bis(diphenylphosphino)ethane)palladium(II), dichlorobis(triphenylphosphine)palladium(II), dichlorotetraamminepalladium(II), dichloro(cycloocta-1,5-diene)palladium(II) and palladium trifluoroacetate(II); and compounds of zero-valent palladium such as tris(dibenzylideneacetone) dipalladium(0) ($Pd_2(dba)_3$), chloroform complex of tris(dibenzylideneacetone) dipalladium(0), tetrakis(triphenylphosphine)palladium(0) and bis(bis(diphenylphosphino)ethane-palladium(0). In the process of the present invention, the amount of the palladium compound is not particularly limited. The amount of the palladium compound is 0.00001 to 20.0% by mole as the amount of palladium per 1 mol of the primary amine. The tertiary amine can be synthesized with a high selectivity when the amount of the palladium compound is in the above range. Since the palladium compound is expensive, it is preferable that the amount of the palladium compound is 0.001 to 5.0 mole as the amount of palladium per 1 mole of the primary amine.

In the process of the present invention, the trialkylphosphine compound used as the catalyst component is not particularly limited. Examples of the trialkylphosphine compound include triethylphosphine, tricyclohexylphosphine, triisopropylphosphine, tri-n-butylphosphine, triisobutylphosphine, tri-sec-butylphosphine and tri-tert-butylphosphine. Among these compounds, tri-tert-butylphosphine is preferable because of the high reaction activity. The triarylphosphine compound is not particularly limited. Examples of the triarylphosphine include triphenylphosphine, benzyldiphenylphosphine, tri-o-toluylphosphine, tri-m-toluylphosphine and tri-p-toluylphosphine. Among these compounds, triphenylphosphine and tri-o-toluylphosphine are preferable. The diphosphine compound is not particularly limited. Examples of the diphosphine compound include bis(dimethylphosphino)methane, bis(dimethylphosphino)ethane, bis(dicyclohexylphosphino)methane, bis(dicyclohexylphosphino)ethane, bis(diphenylphosphino)ethane, 1,3-bis(diphenylphosphino)propane, 1,4-bis(diphenylphosphino)butane, bis(diphenylphosphino)ferrocene, (R)-2,2'-bis(diphenylphosphino)-1,1'-binaphthyl((R)-BINAP), (S)-2,2'-bis(diphenylphosphino)-1,1'-binaphthyl-((S)-BINAP), 2,2'-bis(diphenylphosphino)-1,1'-bisnaphthyl((±)-BINAP), 2S, 3S-bis(diphenylphosphino)butane((S,S)-CHIRAPHOS), 2R,3R-bis(diphenylphosphino)butane((R,R)-CHIRAPHOS), 2,3-bis(diphenyl-phosphino)butane(±)-CHIRAPHOS), (R)-2,2'-bis(di-p-toluylphosphino)-1,1-binaphthyl((R)-Tol-BINAP), (S)-2,2'-bis(di-p-toluylphosphino)-1,1'-binaphthyl((S)-Tol-BINAP), 2,2'-bis(di-p-toluylphosphino)-1,1'-bisnaphthyl((±)-Tol-BINAP), 4R,5R-bis(diphenylphosphinomethyl)-2,2-dimethyl-1,3-dioxorane((R,R)-DIOP), 4S,5S-bis(diphenylphosphino-methyl)-2,2-dimethyl-1,3-dioxorane(S,S)-DIOP), 4,5-bis(diphenyl-phosphinomethyl)-2,2-dimethyl-1,3-dixorane((±)-DIOP), N,N'-dimethyl-(S)-1-[(R)-1',2-bis(diphenylphosphino)ferrocenyl]ethylamine((S),(R)-BPPFA), N,N'-dimethyl-(R)-1-[(S)-1',2-bis(diphenylphosphino)ferrocenyl]-ethylamine((R),(S)-BPPFA) and N,N'-dimethyl-1-[1',2-bis(diphenylphosphino)ferrocenyl]ethylamine((±)-BPPFA). Among these compounds, bis(diphenylphosphino)ethane, 1,3-bis(diphenylphosphino)propane, bis(diphenylphosphino)ferrocene and BINAPs are preferable. BINAPs may be either optically active compounds or racemic compounds.

The amounts of the trialkylphosphine compound, the triphenylphosphine compound and the diphosphine compound are 0.01 to 10,000 mole per 1 mole of the palladium compound. As long as the amounts are in this range, the selectivity of the arylamine does not change. However, it is preferable that the amount is 0.1 to 10 mole per 1 mol of the palladium compound since the phosphine compounds are expensive.

In the process of the present invention, the palladium compound and the phosphine compound are the essential components of the catalyst. The combination of these components is added to the reaction system as the catalyst. As the method of addition of the components, the two components may be added to the reaction system separately or in the form of a complex which is prepared in advance.

The base which can be used in the present reaction is not particularly limited and can be selected from inorganic bases such as sodium carbonate and potassium carbonate and alkali metal alkoxides and organic bases such as tertiary amines. Preferable examples of the base include alkali metal alkoxides such as sodium mothoxide, sodium ethoxide, potassium methoxide, potassium ethoxide, lithium tert-butoxide, sodium tert-butoxide, potassium tert-butoxide and cesium carbonate ($Cs_2CO_3$). The base may be added into the reaction field without any treatment. Alternatively, the base may be prepared from an alkali metal, a hydrogenated alkali metal or a alkali metal hydroxide and an alcohol at the place of reaction and used in the reaction field.

The amount of the base is not particularly limited. It is preferable that the amount is 0.5 mole or more per 1 mole of the halogen atom in the two different types of aryl halides which are added to the reaction system. When the amount of the base is less than 0.5 mol, the activity of the reaction decreases and the yield of the arylamine decreases. Therefore, such an amount is not preferable. When the base is added in a great excess amount, the yield of the arylamine does not change and, on the other hand, treatments after the reaction become complicated. Therefore, it is more preferable that the amount is 1.0 mole or more and less than 5 mole per 1 mole of the halogen atom.

The reaction in the process of the present invention is conducted, in general, in the presence of an inert solvent.

The solvent is not particularly limited as long as the solvent does not adversely affect the reaction much. Examples of the solvent include aromatic hydrocarbon solvents such as benzene, toluene and xylene, ether solvents such as diethyl ether, tetrahydrofuran and dioxane, acetonitrile, dimethylformamide, dimethylsulfoxide and hexamethylphosphotriamide. Aromatic hydrocarbon solvents such as benzene, toluene and xylene are preferable.

It is preferable that the process of the present invention is conducted under the ordinary pressure in an atmosphere of an inert gas such as nitrogen and argon. The process can be conducted also under an added pressure.

In the process of the present invention, the temperature of the reaction can be selected in the range of 20 to 300° C. and preferably in the range of 50 to 200° C. The time of the reaction can be selected in the range of several minutes to 72 hours.

The process of the present invention in which the arylamine compound is obtained in the presence of the catalyst comprising the phosphine compound and the palladium compound and the base is specifically described in Synthesis Examples 12, 13, 14, 17 and 20.

The present invention will be described more specifically with reference to examples in the following. However, the present invention is not limited to the examples.

Synthesis Example 1 (Compound (2))

Synthesis of Intermediate Compound A

In a 200 ml round bottom flask, 0.38 g (2.04 mmole) of 4-bromobenzaldehyde and 0.98 g (4.29 mmole) of ethyl benzylphosphonate were dissolved in 40 ml of dimethylsulfoxide. To this was added 0.5 g (4.49 mmole) of potassium t-butoxide in small portions at the room temperature and the resulting mixture was stirred for 18 hours. The reaction mixture was poured into 500 ml of water, solid was filtered to give yellow solid (0.5 g).

In a 100 ml round bottom flask, the crystals obtained above, 2.0 g (12.0 mmole) of potassium iodide and 1.14 g (6.0 mmole) of copper iodide were dissolved in 10 ml of hexamethylphosphoramide and the resulting mixture was stirred under heating at 150° C. for 6 hours. After the reaction was completed, 10 ml of a 1 N aqueous hydrochloric acid was added to the reaction mixture and the organic layer was extracted with toluene. After the extract was concentrated, the reaction product was purified by recrystallizing from a mixture of diethyl ether and methanol and 0.28 g (the yield: 45%) of the following Intermediate Compound A was obtained:

(Intermediate Compound A)

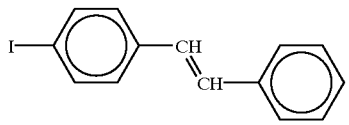

Synthesis of Intermediate Compound B

In a 50 ml round bottom flask, 3 g (17.4 mmole) of p-bromoaniline was suspended in 10 ml of a 6 N aqueous hydrochloric acid and cooled. To the cooled suspension, a solution prepared by dissolving 1.25 g (18.1 mmole) of sodium sulfite in 5.3 ml of water was slowly added dropwise at an inner temperature of 4° C. The resulting mixture was stirred at the same temperature for 1 hour and an aqueous solution of a diazonium compound was obtained.

Separately, in a 100 ml round bottom flask, 0.3 g (1.7 mmole) of anthracene was dissolved in 5 ml of acetone. To this was added a solution prepared by dissolving 0.46 g of copper(II) chloride dihydrate in 5.7 ml of water and the mixture was cooled to 4° C. To the cooled mixture, the aqueous solution of a diazonium compound obtained above was added at the same temperature and the resulting mixture was stirred for over night at the room temperature. After the reaction was completed, precipitated crystals were filtered, washed with methanol and dried and 0.2 g (the yield: 24%) of the following Intermediate Compound B was obtained:

(Intermediate Compound B)

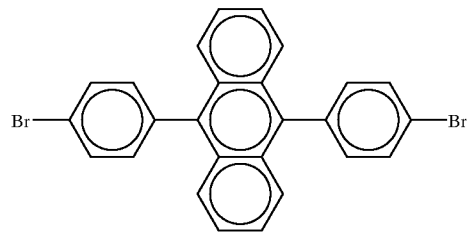

Synthesis of Compound (2)

In a 100 ml round bottom flask, 0.018 g (0.2 mmole) of aniline was dissolved in 5 ml of methylene chloride. To this was added 0.05 g (0.5 mmole) of acetic anhydride and the resulting mixture was stirred at the room temperature for 1 hour. Then, the reaction solvent was removed by distillation and an oily compound was obtained. To the oily compound, 0.56 g (1.8 mmole) of Intermediate Compound A, 5 g of potassium carbonate, 0.3 g of copper powder and 20 ml of nitrobenzene were added and the resulting mixture was stirred at 210° C. for 2 days. Then, the solvent was removed by distillation and 10 ml of diethylene glycol and a solution prepared by dissolving 3 g of potassium hydroxide into 10 ml of water were added. The resulting mixture was stirred at 110° C. for one night. After the reaction was completed, a mixture of ethyl acetate and water was added to the reaction mixture and the organic layer was separated. After the solvent was removed by distillation, crude crystals were obtained.

Subsequently, into a 100 ml round bottom flask, the crude crystal obtained above, 0.05 g (0.1 mmole) of Intermediate Compound B, 5 g of potassium carbonate, 0.3 g of copper powder and 20 ml of nitrobenzene were placed and the mixture was stirred under heating at 220° C. for 2 days. After the reaction was completed, precipitated crystals were separated by filtration, washed with methanol, dried and purified in accordance with the column chromatography (silica gel, hexane/toluene=1/1) and 0.017 g of yellow powder was obtained. The powder was identified to be Compound (2) by the measurements in accordance with NMR, IR and FD-MS (the field desorption mass spectrometry) (the yield: 20%).

Synthesis Example 2 (Compound (9))

Synthesis of Intermediate Compound C

In a 200 ml round bottom flask, 51.2 g (0.3 mole) of diphenylamine, 71.4 g (0.3 mole) of 1,4-dibromobenzene, 34.6 g (0.36 mole) of potassium t-butoxide, 4.2 g (5.9 mmole) of PdCl$_2$(PPh$_3$)$_2$ and 1.2 liter of xylene were mixed together and the obtained mixture was stirred at 130° C. for one night.

After the reaction was completed, the organic layer was concentrated and about 100 g of brown crystals were obtained. The crystals were purified in accordance with the column chromatography (silica gel, hexane/toluene=10/1)

and 28 g (the yield: 29%) of the following Intermediate Compound C was obtained:

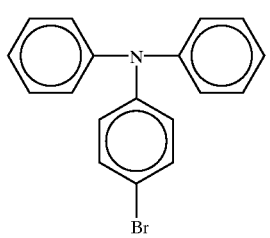

(Intermediate Compound C)

Synthesis of Compound (9)

In a 100 ml round bottom flask, 0.48 g (1 mmole) of Intermediate Compound B was dissolved in 10 ml of diethyl ether and the mixture was cooled to −78° C. To the cooled mixture, 2 ml (1.5 M, 3 mmole) of n-butyllithium was added and the resulting mixture was stirred for 1 hour. Then, a solution prepared by dissolving 0.3 g (3 mmole) of trimethyl borate in 5 ml of diethyl ether was added dropwise to the mixture. After the addition was completed, the resulting mixture was stirred at −78° C. for 1 hour. Then, 10 ml of a 1 N aqueous hydrochloric acid was added at the room temperature. After the organic layer was separated, the solvent was removed by distillation and crude crystals were obtained.

In a 100 ml round bottom flask, the crude crystals obtained above, 0.97 g (3 mmole) of Intermediate Compound C, 12 mg of Pd(PPh$_3$)$_4$ and 0.32 g (1.5 mmole) of potassium phosphate were dissolved in 10 ml of dimethylformamide and the resulting mixture was stirred at 100° C. for 4 hours. After the organic layer was separated, the solvent was removed by distillation and crude crystals were obtained. The crude crystals were purified by the column chromatography (silica gel, benzene/ethyl acetate=50/1) to give 0.13 g of yellow powder. The powder was identified to be Compound (9) by the measurements in accordance with NMR, IR and FD-MS (the yield: 14%).

Synthesis Example 3 (Compound (18))

Synthesis of Intermediate Compound D

A Grignard reagent was prepared by adding magnesium and diethyl ether to 0.48 g (2.0 mmol) of 1,4-dibromobenzene. Separately, in a 100 ml round bottom flask, 5.7 g (20.0 mmole) of 1,4-dibromonaphthalene and 10 mg of NiCl$_2$(dppp) were dissolved in 20 ml of diethyl ether and the resulting mixture was cooled in an ice bath. To the cooled mixture, the Grignard reagent prepared above was added and the obtained mixture was stirred under refluxing for 6 hours. After the reaction was completed, 10 ml of a 1 N aqueous hydrochloric acid was added. After the organic layer was separated, the solvent was removed by distillation and 0.30 (the yield: 30%) of the following Intermediate Compound D was obtained:

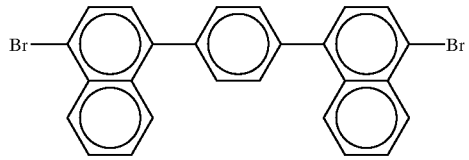

(Intermediate Compound D)

Synthesis of Compound (18)

In a 100 ml round bottom flask, 0.09 g (1.0 mmole) of aniline and 0.25 g (2.5 mmole) of acetic anhydride were dissolved into 5 ml of methylene chloride. The resulting mixture was stirred at the room temperature for 1 hour. Then, the solvent was removed by distillation and an oily compound was obtained. To this was added 0.4 g (4.5 mmole) of Intermediate Compound A, 5 g of potassium carbonate, 0.3 g of copper powder and 20 ml of nitrobenzene and the resulting mixture was stirred under heating at 210° C. for 2 days. Then, the solvent was removed by distillation and 10 ml of diethylene glycol and a solution prepared by dissolving 3 g of potassium hydroxide into 10 ml of water were added to the residue. The resulting mixture was stirred at 110° C. for one night. After the reaction was completed, a mixture of ethyl acetate and water was added to the reaction mixture. After the organic layer was separated, the solvent was removed and crude crystals were obtained.

Subsequently, into a 100 ml round bottom flask, the above crude crystals, 0.5 g (1.0 mmole) of Intermediate Compound D, 5 g of potassium carbonate and 0.3 g of copper powder were dissolved in 20 ml of nitrobenzene and the resulting mixture was stirred under heating at 220° C. for 2 days. After the reaction was completed, precipitated crystals were filtered, washed with methanol, dried and purified by the column chromatography (silica gel, hexane/toluene=1/1) to give 0.1 g of yellow powder. The powder was identified to be Compound (18) by the measurements in accordance with NMR, IR and FD-MS (the yield: 10%).

EXAMPLE 1

A cleaned glass plate having an ITO electrode was coated with a composition which contained Compound (2) obtained above as the light emitting material, 2,5-bis(1-naphthyl)-1,3,4-oxadiazole and a polycarbonate resin (manufactured by TEIJIN KASEI Co., Ltd.; PANLITE K-1300) in amounts such that the ratio by weight was 5:3:2 and was dissolved in tetrahydrofuran in accordance with the spin coating and a light emitting layer having a thickness of 100 nm was obtained. On the obtained light emitting layer, an electrode having a thickness of 150 nm was formed with an alloy prepared by mixing aluminum and lithium in amounts such that the content of lithium was 3% by weight and an organic EL device was obtained. The organic EL device exhibited a luminance of emitted light of 200 (cd/m$^2$), the maximum luminance of 14,000 (cd/m$^2$) and an efficiency of light emission of 2.1 (lm/W) under application of a direct current voltage of 5 V.

EXAMPLE 2

On a cleaned glass plate having an ITO electrode, Compound (9) obtained above was vacuum vapor deposited as the light emitting material and a light emitting layer having a thickness of 100 nm was formed. On the layer formed above, an electrode having a thickness of 100 nm was formed with an alloy prepared by mixing aluminum and lithium in amounts such that the content of lithium was 3% by weight and an organic EL device was obtained. The light emitting layer was formed by vapor deposition under a vacuum of $10^{-6}$ Torr while the temperature of the substrate was kept at the room temperature. The organic EL device exhibited a luminance of emitted light of about 110 (cd/m$^2$), the maximum luminance of 20,000 (cd/m$^2$) and an efficiency of light emission of 2.1 (lm/W) under application of a direct current voltage of 5 V.

EXAMPLE 3

On a cleaned glass plate having an ITO electrode, Compound (2) obtained above was vacuum vapor deposited as the light emitting material and a light emitting layer having a thickness of 50 nm was formed. Then, an electron injecting layer having a thickness of 10 nm was formed by vapor deposition of the following compound (Alq):

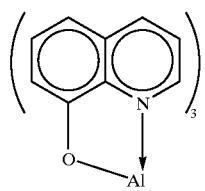

(Alq)

On the layer formed above, an electrode having a thickness of 100 nm was formed with an alloy prepared by mixing aluminum and lithium in amounts such that the content of lithium was 3% by weight and an organic EL device was obtained. The light emitting layer and the electron injecting layer were formed by vapor deposition under a vacuum of $10^{-6}$ Torr while the temperature of the substrate was kept at the room temperature. The organic EL device emitted bluish green light with a luminance of emitted light of about 600 (cd/m$^2$), the maximum luminance of 30,000 (cd/m$^2$) and an efficiency of light emission of 3.0 (lm/W) under application of a direct current voltage of 5 V. When the organic EL device was driven by a constant electric current at an initial luminance of emitted light of 600 (cd/m$^2$), the half life time was as long as 2,000 hours.

EXAMPLES 4 to 16

On a cleaned glass plate having an ITO electrode, the light emitting material shown in Table 1 was vapor deposited and a light emitting layer having a thickness of 80 nm was obtained. Then, the compound (Alq) described above was vacuum vapor deposited as the electron injecting material and an electron injecting layer having a thickness of 20 nm was formed. On the layer formed above, an electrode having a thickness of 150 nm was formed with an alloy prepared by mixing aluminum and lithium in amounts such that the content of lithium was 3% by weight. Organic EL devices were obtained in this manner. The above layers were formed by vapor deposition under a vacuum of $10^{-6}$ Torr while the temperature of the substrate was kept at the room temperature. The light emitting properties of the obtained devices are shown in Table 1. The organic EL devices in these Examples all showed excellent luminances such as the maximum luminance of 10,000 (cd/m$^2$) or greater.

TABLE 1

| Example No. | Type of light emitting material | Efficiency of light emission (lm/W) | Half life time (hour) |
|---|---|---|---|
| 4 | (3) | 2.8 | 3200 |
| 5 | (4) | 2.4 | 2600 |
| 6 | (5) | 3.0 | 3200 |
| 7 | (6) | 1.2 | 1200 |
| 8 | (9) | 2.8 | 2800 |
| 9 | (10) | 1.7 | 1700 |
| 10 | (13) | 1.0 | 1400 |
| 11 | (14) | 2.1 | 2700 |
| 12 | (15) | 2.9 | 4200 |
| 13 | (18) | 1.6 | 1300 |
| 14 | (20) | 2.6 | 1800 |
| 15 | (26) | 3.1 | 4000 |
| 16 | (27) | 1.4 | 2100 |

EXAMPLE 17

On a cleaned glass plate having an ITO electrode, the following compound (TPD74):

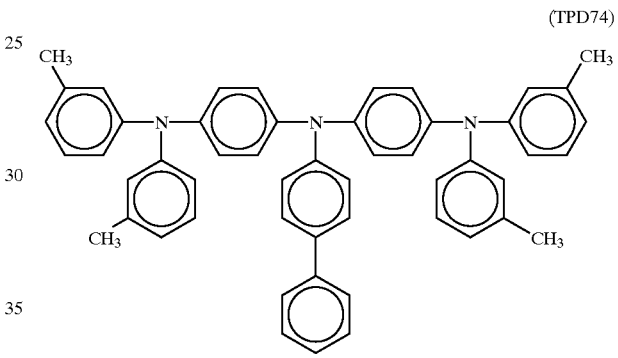

(TPD74)

was vacuum vapor deposited as the hole injecting material and a film having a thickness of 60 nm was formed. Then, the following compound (NPD):

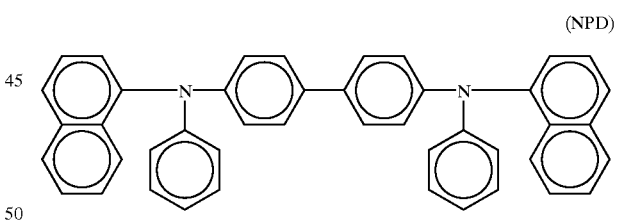

(NPD)

was vacuum vapor deposited on the film formed above as the hole transporting material and a film having a thickness of 20 nm was formed. Then, 4,4'-bis(2,2-diphenylvinyl) biphenyl (DPVBi) and Compound (3) obtained above were vapor deposited simultaneously and a layer having a content of Compound (3) of 5% by weight and the thickness of 40 nm was formed. Compound (3) works as the fluorescent dopant. Subsequently, the compound (Alq) was vapor deposited as the electron injecting material and a layer having a thickness of 20 nm was formed. Then, LiF was vapor deposited and a layer having a thickness of 0.5 nm was formed. An electrode was formed on the above layers by vapor deposition of aluminum and a layer having a thickness of 100 nm was formed. Thus, an organic EL was obtained. The above layers were formed by vapor deposition under a vacuum of $10^{-6}$ Torr while the temperature of the substrate was kept at the room temperature. The organic EL device exhibited a luminance of emitted light as high as about 750 (cd/m²) under application of a direct current voltage of 5 V. When the organic EL device was driven by a constant electric current at an initial luminance of emitted light of 400 (cd/m²), the half life time was as long as 3,000 hours.

Comparative Example 1

An organic EL device was prepared in accordance with the same procedures as those conducted in Example 1 except that the following Compound of Comparative Example 1:

(Compound of Comparative Example 2)

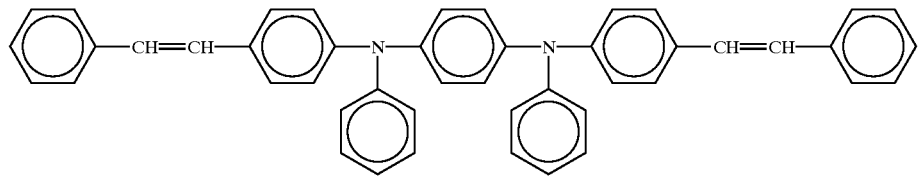

was used as the light emitting material. The obtained organic EL device exhibited a luminance of emitted light of 60 (cd/m²) and an efficiency of light emission of 0.34 (lm/W) under application of a direct current voltage of 5 V. Sufficient properties could not be obtained.

Comparative Example 2

An organic EL device was prepared in accordance with the same procedures as those conducted in Example 3 except that the following Compound of Comparative Example 2:

(Compound of Comparative Example 2)

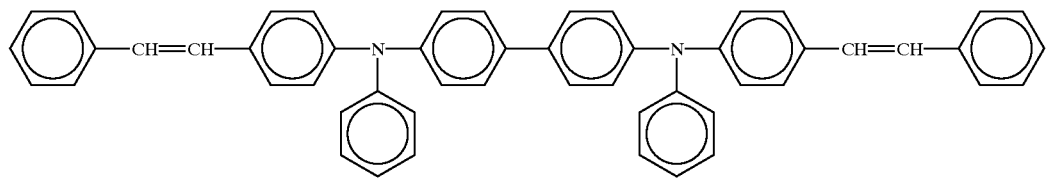

was used as the light emitting material. The obtained organic EL device exhibited a luminance of emitted light of 200 (cd/m²) and an efficiency of light emission of 1.2 (lm/W) under application of a direct current voltage of 5 V. However, when the organic EL device was driven by a constant electric current at an initial luminance of emitted light of 400 (cd/m²), the half life time was as short as 600 hours.

Test of Heat Resistance

The organic EL devices prepared in Examples 2 and 3 and Comparative Examples 1 and 2, which had been used for the measurement of luminance of emitted light, were placed in a chamber kept at the constant temperature of 100° C. After 500 hours, luminance of light emission was measured again. The values of luminance before and after the devices were kept in the chamber were compared and the retention of luminance was calculated.

The retentions of luminance of the organic EL devices prepared in Examples 2 and 3 and Comparative Examples 1 and 2 thus obtained were 85%, 90%, 25% and 30%, respectively. As shown by this result, the compounds used as the light emitting material in Comparative Examples 1 and 2 could not retain luminance because the compounds had glass transition temperatures lower than 100° C. In contrast, the compounds used as the light emitting material in Examples 2 and 3 exhibited excellent heat resistance and could retain luminance for a long time because the compounds had glass transition temperatures higher than 110° C.

Synthesis Example 4 (Compound (30))

Synthesis of Intermediate Compound E (6,12-diiodochrysene)

In a 300 ml round bottom flask, 5 g (22 mmole) of chrysene was dissolved in 100 ml of carbon tetrachloride. To this was added 16 g (64 mmole) of iodine dissolved in 100 ml of carbon tetrachloride dropwise at the room temperature. The resulting mixture was stirred under heating for 5 hours, precipitated crystals were separated by filtration and the crystals were washed with 100 ml of carbon tetrachloride. The crude crystals were recrystallized from 200 ml of toluene and Intermediate Compound E was obtained (the yield: 35%).

Synthesis of Compound (30)

In a 100 ml two-necked flask, 2 g (10 mmole) of 4-aminostilbene was dissolved in 20 ml of methylene chloride. To this was added 2.5 g (25 mmole) of acetic anhydride. The resulting mixture was stirred at the room temperature for 1 hour. Then, the reaction solvent was removed by distillation and an oily compound was obtained. In a 300 ml two-necked flask, 4.1 g (20 mmole) of iodobenzene, 3 g (30 mmole) of potassium carbonate, 0.06 g (1 mmole) of copper powder and 100 ml of nitrobenzene were added to the obtained oily compound and the obtained mixture was stirred under heating at 220° C. for 2 days. Then, the solvent was removed by distillation and 10 ml of diethylene glycol and a solution prepared by dissolving 30 g of potassium hydroxide into 100 ml of water were added to the residue. The reaction was allowed to proceed at 110° C. for one night. After the reaction was completed, a mixture of ethyl acetate and water was added to the reaction mixture. After the organic layer was separated, the solvent was removed by distillation and crude crystals were obtained.

Subsequently, in a 300 ml two-necked flask, the above crude crystals, 2.4 g (5 mmole) of Intermediate Compound E, 3 g (20 mmole) of potassium carbonate and 0.06 g (1 mmole) of copper powder were dissolved in 100 ml of nitrobenzene and the resulting mixture was stirred under heating at 230° C. for 2 days. After the reaction was completed, precipitated crystals were separated by filtration, washed with methanol, dried and purified in accordance with the column chromatography (silica gel, hexane/toluene=1/1) and 1.0 g of yellow powder was obtained. The powder was identified to be Compound (30) by the measurements in accordance with NMR, IR and FD-MS (the yield: 25%).

Synthesis Example 5 (Compound (36))

Synthesis of Compound (36)

In a 100 ml round bottom flask, 3.4 g (20 mmole) of diphenylamine, 4.8 g (10 mmole) of Intermediate Compound E, 3 g (30 mmole) of potassium carbonate and 0.06 g (1 mmole) of copper powder were dissolved in 100 ml of nitrobenzene and the resulting mixture was stirred under heating at 210° C. for 2 days. After the reaction was completed, precipitated crystals were separated by filtration, washed with methanol, dried and purified in accordance with the column chromatography (silica gel, hexane/toluene=1/1) and 2.8 g of yellow powder was obtained. The powder was identified to be Compound (36) by the measurements in accordance with NMR, IR and FD-MS (the yield: 50%).

Synthesis Example 6 (Compound (38))

Synthesis of Compound (38)

In a 100 ml four-necked flask, 1.0 g (41 mmole) of magnesium, 1 ml of tetrahydrofuran and a small piece of iodine were placed under an argon stream. To this mixture, 9.7 g (30 mmole) of 4-bromotriphenylamine dissolved in 100 ml of tetrahydrofuran was slowly added dropwise at the room temperature. After the addition was completed, the reaction mixture was stirred under heating at 60° C. for 1 hour and a Grignard reagent was prepared.

In a 300 ml four-necked flask, 4.8 g (10 mmole) of Intermediate Compound E, 0.28 g (0.4 mmole) of $PdCl_2$ $(PPh_3)_2$ and 1.0 ml (1 mmole) of a 1.0 M toluene solution of AlH(iso-Bu)$_2$ were dissolved in 50 ml of tetrahydrofuran under an argon stream. To this was added the Grignard reagent prepared above dropwise at the room temperature. The temperature was elevated and the reaction mixture was heated under refluxing for over night. After the reaction was completed, the reaction liquid was cooled with ice water. Precipitated crystals were separated by filtration and washed with acetone. The obtained crude crystals were recrystallized from 100 ml of acetone and 4.3 g of yellow powder was obtained. The powder was identified to be Compound (38) by the measurement in accordance with NMR, IR and FD-MS (the yield: 60%).

Synthesis Example 7 (Compound (47))

Synthesis of Compound (47)

In a 100 ml two-necked flask, 2.4 g (10 mmole) of 6-aminochrysene was dissolved into 20 ml of methylene chloride. To this was added 2.5 g (25 mmole) of acetic anhydride and the resulting mixture was stirred at the room temperature for 1 hour. Then, the reaction solvent was removed by distillation and an oily compound was obtained. In a 300 ml two-necked flask, 4.1 g (20 mmole) of iodobenzene, 3 g (30 mmole) of potassium carbonate and 0.06 g (1 mmole) of copper powder were dissolved in 100 ml of nitrobenzene. To this was added the oily compound and the resulting mixture was stirred under heating at 220° C. for 2 days. Then, the solvent was removed by distillation and 10 ml of diethylene glycol and a solution prepared by dissolving 30 g of potassium hydroxide into 100 ml of water were added to the residue. The reaction was allowed to proceed at 110° C. for one night. After the reaction was completed, a mixture of ethyl acetate and water was added to the reaction mixture. After the organic layer was separated, the solvent was removed by distillation and crude crystals were obtained.

Subsequently, in a 300 ml two-necked flask, the crude crystals obtained above, 2 g (5 mmole) of 4,4'-diiodobiphenyl, 3 g (30 mmole) of potassium carbonate and 0.06 g (1 mmole) of copper powder were dissolved in 100 ml of nitrobenzene and the resulting mixture was stirred under heating at 230° C. for 2 days. After the reaction was completed, precipitated crystals were separated by filtration, washed with methanol, dried -and purified in accordance with the column chromatography (silica gel, hexane/toluene=1/3) and 0.8 g of yellow powder was obtained. The powder was identified to be Compound (47) by the measurements in accordance with NMR, IR and FD-MS (the yield: 30%).

EXAMPLE 18

A cleaned glass plate having an ITO electrode was coated with a composition which contained Compound (30) obtained above as the light emitting material, 2,5-bis(1-naphthyl)-1,3,4-oxadiazole and a polycarbonate resin (manufactured by TEIJIN KASEI Co., Ltd.; PANLITE K-1300) in amounts such that the ratio by weight was 5:3:2 and was dissolved in tetrahydrofuran in accordance with the spin coating and a light emitting layer having a thickness of 100 nm was obtained. On the obtained light emitting layer, an electrode having a thickness of 150 nm was formed with an alloy prepared by mixing aluminum and lithium in amounts such that the content of lithium was 3% by weight and an organic EL device was obtained. The organic EL device exhibited a luminance of emitted light of 320 (cd/m$^2$), the maximum luminance of 14,000 (cd/m$^2$) and an efficiency of light emission of 2.5 (lm/W) under application of a direct current voltage of 5 V.

EXAMPLE 19

On a cleaned glass plate having an ITO electrode, Compound (37) obtained above was vacuum vapor deposited as the light emitting material and a light emitting layer having a thickness of 100 nm was formed. On the layer formed above, an inorganic electron injecting layer having a thickness of the film of 0.3 nm was formed with lithium fluoride. Then, an electrode having a thickness of 100 nm was formed with aluminum and an organic EL device was obtained. The light emitting layer was formed by vapor deposition under a vacuum of 10$^{-6}$ Torr while the temperature of the substrate was kept at the room temperature. The organic EL device exhibited a luminance of emitted light of about 110 (cd/m$^2$), the maximum luminance of 20,000 (cd/m$^2$) and an efficiency of light emission of 1.2 (lm/W) under application of a direct current voltage of 5 V.

EXAMPLE 20

On a cleaned glass plate having an ITO electrode, CuPc was vacuum vapor deposited as the hole injecting material and a hole injecting layer having a thickness of 40 nm was formed. Then, a hole transporting layer having a thickness of 20 nm was formed by using Compound (47) obtained above as the hole transporting material and a light emitting layer having a thickness of 60 nm was formed by vacuum vapor deposition of the compound (Alq) described above. Rubrene was added to the light emitting layer in an amount of 4% by weight. On the layers formed above, an electrode having a thickness of 100 nm was formed with an alloy prepared by mixing aluminum and lithium in amounts such that the content of lithium was 3% by weight and an organic EL device was obtained. The above layers were formed by vapor deposition under a vacuum of $10^{-6}$ Torr while the temperature of the substrate was kept at the room temperature. The organic EL emitted green light with a luminance of emitted light of about 700 (cd/m$^2$), the maximum luminance of 80,000 (cd/m$^2$) and an efficiency of light emission of 6.0 (lm/W) under application of a direct current voltage of 5 V. When the organic EL device was driven by a constant electric current at an initial luminance of emitted light of 600 (cd/m$^2$), the half life time was as long as 4,000 hours.

EXAMPLES 21 to 33

On a cleaned glass plate having an ITO electrode, a hole injecting layer having a thickness of 20 nm was formed by vacuum vapor deposition of the hole injecting material shown in Table 2. A light emitting layer having a thickness of 60 nm was formed by vapor deposition of the compound (Alq) described above as the light emitting material and rubrene was added to the light emitting layer in an amount of 4% by weight. On the layers formed above, an electrode having a thickness of 150 nm was formed with an alloy prepared by mixing aluminum and lithium in amounts such that the content of lithium was 3% by weight. Organic EL devices were obtained in this manner. The above layers were formed by vapor deposition under a vacuum of $10^{-6}$ Torr while the temperature of the substrate was kept at the room temperature. The light emitting properties of the obtained devices are shown in Table 2. The organic EL devices in these Examples all showed excellent luminances such as the maximum luminance of 10,000 (cd/m$^2$) or greater.

TABLE 2

| Example | Type of hole transporting material | Half life time (hour) |
|---|---|---|
| 21 | (30) | 5200 |
| 22 | (36) | 5600 |
| 23 | (37) | 4200 |
| 24 | (38) | 3200 |
| 25 | (41) | 4800 |
| 26 | (43) | 6700 |
| 27 | (48) | 2400 |
| 28 | (49) | 5700 |
| 29 | (50) | 5200 |
| 30 | (51) | 6000 |
| 31 | (53) | 4000 |
| 32 | (55) | 4000 |
| 33 | (56) | 3200 |

EXAMPLE 34

On a cleaned glass plate having an ITO electrode, compound (TPD 74) described above was vacuum vapor deposited as the hole injecting material and a layer having a thickness of 60 nm was formed. Then, the compound (NPD) obtained above was vacuum vapor deposited as the hole transporting material and a layer having a thickness of 20 nm was formed.

4,4'-bis(2,2-Diphenylvinyl)phenylanthracene (DPVDPAN) as the light emitting material and Compound (36) described above as the dopant were vapor deposited simultaneously and a layer which had a content of Compound (36) of 2% by weight and a thickness of 40 nm was formed. Then, the compound (Alq) described above was vapor deposited as the charge injecting material and a layer having a thickness of 20 nm was formed. After lithium fluoride was vapor deposited and a layer having a thickness of 0.5 nm was formed, aluminum was vapor deposited and an electrode having a thickness was 100 nm formed. Thus, an organic EL device was obtained. The above layers were formed by vapor deposition under a vacuum of $10^{-6}$ Torr while the temperature of the substrate was kept at the room temperature. The organic EL device exhibited a luminance of emitted light as high as 500 (cd/m$^2$) under application of a direct current voltage of 8 V and the emitted light had blue color of excellent purity. When the organic EL device was driven by a constant electric current at an initial luminance of emitted light of 100 (cd/m$^2$), the half life time was as long as 7,000 hours.

The spectrum of the light emitted by this device was measured and it was found that the spectrum was the same as that of the device using DPVBi. This means that Compound (36) did not affect the light emission but exhibited the effect of extending the life of the device.

Comparative Example 3

An organic EL device was prepared in accordance with the same procedures as those conducted in Example 34 except that Compound (36) described above was not added as the dopant. When the prepared organic EL device was driven by a constant electric current at an initial luminance of emitted light of 100 (cd/m$^2$), the half life time was shorter than the half life time in Example 34, i.e., 4,000 hours.

Comparative Example 4

An organic EL device was prepared in accordance with the same procedures as those conducted in Example 20 except that Compound of Comparative Example 2 described above was used as the hole transporting material.

The prepared organic EL device exhibited a luminance of emitted light of 300 (cd/m$^2$) and an efficiency of light emission of 4.2 (lm/W) under application of a direct current voltage of 5 V. However, when the organic EL device was driven by a constant electric current at an initial luminance of emitted light of 400 (cd/m$^2$), the half life time was as short as 300 hours.

Test of Heat Resistance

The organic EL devices prepared in Examples 20 and 27 and Comparative Example 4, which had been used for the measurement of luminance of emitted light, were placed in a chamber kept at the constant temperature of 105° C. After 500 hours, luminance of light emission was measured again. The values of luminance before and after the devices were kept in the chamber were compared and the retention of luminance was calculated.

The retentions of luminance of the organic EL devices prepared in Examples 20 and 27 and Comparative Example 4 thus obtained were 87%, 90% and 25%, respectively. As shown by this result, the compounds used as the light emitting material in Comparative Example 4 could not retain luminance because the compounds had a glass transition temperature lower than 105° C. In contrast, the compounds used for the light emitting material in Examples 20 and 27 exhibited excellent heat resistance and could retain luminance for a long time because the compounds had glass transition temperatures higher than 110° C.

Synthesis Example 8 (Compound (58))

Synthesis of Intermediate Compound F (5,11-dibromonaphthacene)

In a 2 liter round bottom flask, 50 g (0.19 mmole) of 5,12-naphthacene, 108 g (0.57 mmole) of tin(IV) chloride, 500 ml of acetic acid and 200 ml of concentrated hydrochloric acid were placed. The resulting mixture was stirred for reflux for 2 hours. After the reaction was completed, precipitated crystals were separated by filtration, washed with water and dried in a vacuum drying chamber and 48 g of crude crystals were obtained.

Subsequently, in a 2 liter four-necked flask, the crude crystals obtained above and 50 g (0.19 mmole) of triphenylphosphine were dissolved in 300 ml of dimethylformamide under an argon stream. To this was added 64 g (0.4 mmole) of bromine dissolved in 200 ml of dimethylformamide slowly dropwise and the resulting mixture was stirred at ambient temperature. After the addition was completed, the mixture was stirred under heating at 200° C. for one night. After the reaction was completed, dimethylformamide was removed by distillation in vacuo and 200 ml of water was added to the residue. The organic layer was extracted with toluene. The extract was dried with magnesium sulfate and concentrated in vacuo using a rotary evaporator and an oily compound was obtained. The oily compound was purified in accordance with the column chromatography (silica gel, hexane/toluene=1/1) and 30 g of yellow powder was obtained. The powder was identified to be Intermediate Compound F by the measurements in accordance with NMR, IR and FD-MS (the yield: 40%).

Synthesis of Compound (58)

In a 100 ml two-necked flask, 2 g (10 mmole) of 4-aminostilbene was dissolved in 20 ml of methylene chloride. To this was added 2.5 g (25 mmole) of acetic anhydride and the resulting mixture was stirred at the room temperature for 1 hour. Then, the reaction solvent was removed by distillation and an oily compound was obtained. In a 300 ml two-necked flask, 4.1 g (20 mmole) of iodobenzene, 3 g (30 mmole) of potassium carbonate, 0.06 g (1 mmole) of copper powder and 100 ml of nitrobenzene were added to the obtained oily compound and the obtained mixture was stirred under heating at 220° C. for 2 days. Then, the solvent was removed by distillation and 10 ml of diethylene glycol and a solution prepared by dissolving 30 g of potassium hydroxide into 100 ml of water were added to the residue. The reaction was allowed to proceed at 110° C. for one night. After the reaction was completed, a mixture of ethyl acetate and water was added to the reaction mixture. After the organic layer was separated, the solvent was removed and crude crystals were obtained.

Subsequently, in a 100 ml two-necked flask, the crude crystals obtained above, 1.9 g (5 mmole) of Intermediate Compound F, 1.3 g (12 mmole) of potassium t-butoxide and 40 mg (5% by mole) of $PdCl_2(PPh_3)_2$ were dissolved in 30 ml of xylene under an argon stream. The resulting mixture was stirred under heating at 130° C. for over night. After the reaction was completed, precipitated crystals were separated by filtration, washed with methanol, dried and purified in accordance with the column chromatography (silica gel, hexane/toluene=1/1) and 0.9 g of yellow powder was obtained. The powder was identified to be Compound (58) by the measurements in accordance with NMR, IR and FD-MS (the yield: 25%).

Synthesis Example 9

Synthesis of Compound (59)

In a 300 ml four-necked flask, 2 g (10 mmole) of 4-hydroxystilbene and 5.2 g (20 mmole) of triphenylphosphine were dissolved in 50 ml of dimethylformamide under an argon stream. To this mixture was added 5 g (20 mmole) of iodine dissolved in 50 ml of dimethylformamide slowly dropwise at the room temperature and the reaction was allowed to proceed. After the addition was completed, the reaction mixture was stirred at 200° C. for over night. After the reaction was completed, dimethylformamide was removed by distillation in vacuo and 200 ml of water was added to the residue. The organic layer was extracted with toluene. The extract was dried with magnesium sulfate and concentrated in vacuo using a rotary evaporator and an oily compound was obtained. The oily compound was purified in accordance with the column chromatography (silica gel, hexane/toluene=1/1) and 2.5 g of yellow powder was obtained.

Separately, in a 100 ml two-necked flask, 2 g (10 mmole) of 4-aminostilbene was dissolved in 20 ml of methylene chloride. To this was added 2.5 g (25 mmole) of acetic anhydride and the resulting mixture was stirred at the room temperature for 1 hour. Then, the reaction solvent was removed by distillation and an oily compound was obtained.

In a 300 ml two-necked flask, 2.5 g of the yellow powder obtained above, 3 g (30 mmole) of potassium carbonate, 0.06 g (1 mmole) of copper powder and 100 ml of nitrobenzene were added to the above oily compound. The resulting mixture was stirred under heating at 220° C. for 2 days. To the residue obtained by removing the solvent from the above mixture by distillation, 10 ml of diethylene glycol and 30 g of potassium hydroxide dissolved in 100 ml of water were added and the reaction was allowed to proceed at 110° C. for over night. After the reaction was completed, a mixture of ethyl acetate and water was added to the reaction mixture. After the organic layer was separated, the solvent was removed by distillation and crude crystals were obtained.

Subsequently, in a 300 ml two-necked flask, the above crude crystals, 2.4 g (5 mmole) of Intermediate Compound F, 1.3 g (12 mmole) of potassium t-butoxide and 40 mg (5% by mole) of $PdCl_2(PPh_3)_2$ were dissolved in 30 ml of xylene under an argon stream. The resulting mixture was stirred under heating at 130° C. and the reaction was allowed to proceed for over night. After the reaction was completed, precipitated crystals were separated by filtration, washed with methanol, dried and purified by the column chromatography (silica gel, hexane/toluene=1/1) and 0.2 g of yellow powder was obtained. The powder was identified to be Compound (59) by the measurements in accordance with NMR, IR and FD-MS (the yield: 5%).

Synthesis Example 10 (Compound (61))

Synthesis of Compound (61)

In a 300 ml four-necked flask, 9.7 g (30 mmole) of 4-bromotriphenylamine, 50 ml of toluene and 50 ml of diethyl ether were placed and the resulting mixture was cooled with ice water under an argon stream. To the cooled mixture, a mixture of 22 ml (33 mmole) of a hexane solution (1.52 mole/liter) of n-butyllithium and 100 ml of tetrahydrofuran were slowly added dropwise at the room temperature and the resulting mixture was stirred. After 4.3 g (10 mmole) of 6,13-dibromopenthacene was added to the reaction mixture, the obtained mixture was stirred at the same temperature for one night. After the reaction was completed, 500 ml of water was added to the reaction mixture and the organic layer was extracted with diethyl ether. The extract was dried with magnesium sulfate and concentrated in vacuo using a rotary evaporator and 7.4 g of an oily compound was obtained.

In a 300 ml four-necked flask, the above compound, 6.6 g (40 mmole) of potassium iodide and 100 ml of acetic acid were placed and the resulting mixture was heated under refluxing for 1 hour. After the reaction was completed, the reaction mixture was cooled to the room temperature and precipitated crystals were separated by filtration. The obtained crystals were washed with water and acetone and 2.7 g of orange solid was obtained. The orange solid was identified to be Compound (61) by the measurement in accordance with NMR, IR and FD-MS (the yield: 35%).

Synthesis Example 11 (Compound (62))

Synthesis of Intermediate Compound G (5,11-diiodonaphthacene)

In a 500 ml round bottom flask, 50 g (0.22 mmole) of naphthacene and 200 ml of tetrachloroethane were placed. To this was added 160 g (0.64 mole) of iodine dissolved in 200 ml of carbon tetrachloride slowly dropwise at the room temperature and the resulting mixture was stirred under heating for 5 hours. Precipitated crystals were separated by filtration and washed with 500 ml of methanol. The obtained crude crystals were recrystallized from 200 ml of toluene and 34 g of Intermediate Compound G was obtained (the yield: 40%).

Synthesis of Compound (62)

In a 100 ml four-necked flask, 1.0 g (41 mmole) of magnesium, 1 ml of tetrahydrofuran and a small piece of iodine were placed under an argon stream. To this was added 9.7 g (30 mmole) of 4-bromotriphenylamine dissolved in 100 ml of tetrahydrofuran slowly dropwise at the room temperature. After the addition was completed, the resulting mixture was stirred under heating at 60° C. for 1 hour and a Grignard reagent was prepared.

In a 300 ml four-necked flask, 4.8 g (10 mmole) of Intermediate Compound G, 0.28 g (0.4 mmole) of $PdCl_2(PPh_3)_2$ and 1.0 ml (1 mmole) of a 1.0 M toluene solution of $AlH(iso-Bu)_2$ were dissolved in 50 ml of tetrahydrofuran under an argon stream. To the this mixture, the Grignard reagent prepared above was added dropwise at the room temperature. The temperature was elevated and the reaction mixture was heated under refluxing for one night. After the reaction was completed, the reaction liquid was cooled with ice water. Precipitated crystals were separated by filtration and washed with acetone. The obtained crude crystals were recrystallized from 100 ml of acetone and 3.6 g of yellow powder was obtained. The powder was identified to be Compound (62) by the measurement in accordance with NMR, IR and FD-MS (the yield: 50%).

EXAMPLE 35

A cleaned glass plate having an ITO electrode was coated with a composition which contained Compound (58) obtained above as the light emitting material, 2,5-bis(1-naphthyl)-1,3,4-oxadiazole and a polycarbonate resin (manufactured by TEIJIN KASEI Co., Ltd.; PANLITE K-1300) in amounts such that the ratio by weight was 5:2:2 and was dissolved in tetrahydrofuran in accordance with the spin coating and a light emitting layer having a thickness of 100 nm was obtained. On the obtained light emitting layer, an electrode having a thickness of 150 nm was formed with an alloy prepared by mixing aluminum and lithium in amounts such that the content of lithium was 3% by weight and an organic EL device was obtained. The organic EL device emitted yellowish orange light with a luminance of emitted light of 130 (cd/m$^2$), the maximum luminance of 14,000 (cd/m$^2$) and an efficiency of light emission of 1.2 (lm/W) under application of a direct current voltage of 5 V.

EXAMPLE 36

On a cleaned glass plate having an ITO electrode, Compound (71) obtained above was vacuum vapor deposited as the light emitting material and a light emitting layer having a thickness of 100 nm was prepared. On the obtained light emitting layer, an electrode having a thickness of 100 nm was formed with an alloy prepared by mixing aluminum and lithium in amounts such that the content of lithium was 3% by weight and an organic EL device was obtained. The light emitting layer was formed by vapor deposition under a vacuum of $10^{-6}$ Torr while the temperature of the substrate was kept at the room temperature. The organic EL device emitted orange light with a luminance of emitted light of 120 (cd/m$^2$), the maximum luminance of 1,800 (cd/m$^2$) and an efficiency of light emission of 0.3 (lm/W) under application of a direct current voltage of 5 V.

EXAMPLE 37

On a cleaned glass plate having an ITO electrode, Compound (71) obtained above was vacuum vapor deposited as the light emitting material and a light emitting layer having a thickness of 50 nm was prepared. Then, the compound (Alq) described above was vacuum vapor deposited on the obtained light emitting layer and an electron injection layer having a thickness of 10 nm was formed. On the formed layer, an electrode having a thickness of 100 nm was formed with an alloy prepared by mixing aluminum and lithium in amounts such that the content of lithium was 3% by weight and an organic EL device was obtained. The light emitting layer and the electron injecting layer were formed by vapor deposition under a vacuum of $10^{-6}$ Torr while the temperature of the substrate was kept at the room temperature. The organic EL device emitted orange light with a luminance of emitted light of about 200 (cd/m$^2$), the maximum luminance of 12,000 (cd/m$^2$) and an efficiency of light emission of 1.0 (lm/W) under application of a direct current voltage of 5 V.

EXAMPLES 38 to 46

On a cleaned glass plate having an ITO electrode, a light emitting material shown in Table 3 was vacuum vapor deposited and a light emitting layer having a thickness of 80 nm was prepared. Then, the compound (Alq) described above was vacuum vapor deposited on the obtained light emitting layer and an electron injection layer having a thickness of 20 nm was formed. On the formed layer, an electrode having a thickness of 150 nm was formed with an alloy prepared by mixing aluminum and lithium in amounts such that the content of lithium was 3% by weight. In this manner, organic EL devices were obtained. The above layers were formed by vapor deposition under a vacuum of $10^{-6}$ Torr while the temperature of the substrate was kept at the room temperature. The properties of light emission of the obtained organic EL devices are shown in Table 3. The organic EL devices in these Examples all showed excellent luminances such as the maximum luminance of 5,000 (cd/m$^2$) or greater.

TABLE 3

| Example | Type of light emitting material | Efficiency of light emission (lm/W) | Half life time (hour) |
|---|---|---|---|
| 38 | (59) | 1.2 | 1400 |
| 39 | (60) | 1.4 | 1600 |
| 40 | (61) | 0.7 | 1700 |
| 41 | (62) | 0.8 | 850 |
| 42 | (65) | 0.4 | 1200 |
| 43 | (67) | 0.6 | 1700 |
| 44 | (70) | 1.6 | 2400 |
| 45 | (72) | 1.2 | 1600 |
| 46 | (74) | 0.5 | 1200 |

EXAMPLE 47

On a cleaned glass plate having an ITO electrode, the compound (TPD 74) described above was vacuum vapor deposited as the hole injecting material and a layer having a thickness of 60 nm was formed. Then, the compound (NPD) described later was vapor deposited as the hole transporting material and a layer having a thickness of 20 nm was formed.

Then, 4,4'-bis(2,2-diphenylvinyl)biphenyl (DPVBi) and Compound (58) described above were simultaneously vacuum deposited as the light emitting materials and a layer having a content of Compound (58) of 5% by weight and a thickness of 40 nm was formed. Compound (58) worked also as a fluorescent dopant. Then, the compound (Alq) described above was vapor deposited as the election injection material and a layer having a thickness of 20 nm was formed. On the formed layer, lithium fluoride was vapor deposited and a layer having a thickness of 0.5 nm was formed. Then, aluminum was vapor deposited and a layer having a thickness of 100 nm was formed. Thus, an electrode was formed and an organic EL device was obtained. The above layers were formed by vapor deposition under a vacuum of $10^{-6}$ Torr while the temperature of the substrate was kept at the room temperature. The organic EL device emitted yellow light with a luminance of emitted light of about 600 (cd/m$^2$) under application of a direct current voltage of 5 V. When the organic EL device was driven by a constant electric current at an initial luminance of emitted light of 400 (cd/m$^2$), the half life time was as long as 2,800 hours.

EXAMPLE 48

An organic EL device was prepared in accordance with the same procedures as those conducted in Example 47 except that the light emitting layer was formed by simultaneously vapor depositing the compound (Alq) described above as the light emitting material and Compound (61) described above as the dopant and a light emitting layer having the content of Compound (61) of 5% by weight was formed. The organic EL device emitted red light with a luminance of emitted light of about 240 (cd/m$^2$) under application of a direct current voltage of 5 V. When the organic EL device was driven by a constant electric current at an initial luminance of emitted light of 400 (cd/m$^2$), the half life time was as long as 3,200 hours.

Comparative Example 5

An organic EL device was prepared in accordance with the same procedures as those conducted in Example 35 except that (Compound of Comparative Example 1) described above was used as the light emitting material.

The organic EL device exhibited luminance of emitted light of about 60 (cd/m$^2$) and an efficiency of light emission of 0.34 (lm/W) under application of a direct current voltage of 5 V. Sufficient properties could not be obtained. The emitted light was blue light.

Comparative Example 6

An organic EL device was prepared in accordance with the same procedures as those conducted in Example 37 except that (Compound of Comparative Example 2) described above was used as the light emitting material.

The organic EL device exhibited a luminance of emitted light of about 200 (cd/m$^2$) and an efficiency of light emission of 1.2 (lm/W) under application of a direct current voltage of 5 V. However, when the organic EL device was driven by a constant electric current at an initial luminance of emitted light of 400 (cd/m$^2$), the half life time was as short as 600 hours. The emitted light was blue light.

Comparative Example 7

An organic EL device was prepared in accordance with the same procedures as those conducted in Example 47 except that (Compound of Comparative Example 1) described above was used in place of Compound (58).

The organic EL device exhibited a luminance of emitted light of about 200 (cd/m$^2$) under application of a direct current voltage of 5 V. However, when the organic EL device was driven by a constant electric current at an initial luminance of emitted light of 400 (cd/m$^2$), the half life time was as short as 700 hours. The emitted light was blue light.

Synthesis Example 12 (Compound (75))

Synthesis of Compound (75)

In a 200 ml three-necked flask, 2.16 g (5.5 mmole) of 6,12-dibromonaphthacene (40577-78-4), 0.06 g (0.3 mmole) of Pd(OAc)$_2$, 0.23 g (1.1 mmole) of P(tBu)$_3$, 1.51 g (15.7 mmole) of NaOtBu and 1.89 g (11.2 mmole) of Ph$_2$NH were dissolved in 25 ml of toluene under an argon stream. The resulting mixture was stirred under heating at 120° C. and the reaction was allowed to proceed for 7 hours. After the reaction was completed, the reaction mixture was left standing and cooled. After red crystals were separated by filtration, the crystals were washed with toluene and water and dried in vacuo and 3.02 g of red powder was obtained. The powder was identified to be Compound (75) by the measurements in accordance with NMR, IR and FD-MS (the yield: 96%). The data obtained in NMR (CDCl$_3$, TMS) were as follows: 6.8~7.0 (m, 2H), 7.0~7.4 (m, 10H), 7.8~7.9 (m, 1H), 8.0~8.1 (m, 1H) and 8.85 (s, 1H).

EXAMPLE 49

On a cleaned glass plate having an ITO electrode, Compound (TPD74) described above was vacuum vapor deposited as the hole injecting material and a layer having a thickness of 60 nm was formed. Then, the compound (NPD) described above was vacuum vapor deposited as the hole transporting material and a layer having a thickness of 20 nm was formed.

Then, the compound (Alq) described above as the light emitting material and Compound (75) described above as the dopant were simultaneously vapor deposited and a layer having a content of Compound (75) of 2% by weight and a thickness of 40 nm was formed. Then, the compound (Alq) described above was vapor deposited as the electron injecting material and a layer having a thickness of 20 nm was formed. After lithium fluoride was vapor deposited and a layer having a thickness of 20 nm was formed, aluminum was vapor deposited and a layer having a thickness of 100 nm was formed. Thus, an electrode was formed and an organic EL device was prepared. The above layers were formed by vapor deposition under a vacuum of $10^{-6}$ vorr while the temperature of the substrate was kept at the room temperature. The organic EL device exhibited a luminance of emitted light as high as 500 (cd/m$^2$) under application of a direct current voltage of 8 V and the emitted light was orange light. The organic EL device exhibited a luminance of emitted light as high as 500 (cd/m$^2$) under application of a direct current voltage of 8 V and the emitted light was orange light. When the organic EL device was driven by a constant electric current at an initial luminance of emitted light of 500 (cd/m$^2$), the organic EL device had a particularly long half life time, which was longer than 2,000 hours.

EXAMPLE 50

An organic EL device was prepared in accordance with the same procedures as those conducted in Example 49 except that Compound (86) described above was used as the dopant in place of Compound (75). When the organic EL device was driven by a constant electric current at an initial luminance of emitted light of 500 (cd/m$^2$), the organic EL device had a half life time as long as 2,000 hours. The emitted light was vermilion light.

EXAMPLE 51

An organic EL device was prepared in accordance with the same procedures as those conducted in Example 49 except that Compound (82) described above was used as the dopant in place of Compound (75). The organic EL device exhibited an initial luminance of emitted light of 500 (cd/m$^2$) and the organic EL device had a half life time as long as 2,800 hours or longer when the organic EL device was driven by a constant electric current. The emitted light was red light.

Synthesis Example 13 (Compound (100))

Synthesis of Intermediate Compound H

In a 1 liter three-necked flask equipped with a condenser, 22.7 g (0.1 mole) of 4-bromophthalic anhydride and 42.4 g (0.4 mole) of sodium carbonate were suspended in 300 ml of water and the components were dissolved by heating at 60° C. under an argon stream. After the mixture was dissolved, the resulting mixture was cooled to the room temperature. To the cooled mixture, 18.3 g (0.15 mole) of phenylboric acid and 0.7 g (3% by mole) of palladium acetate were added and the obtained mixture was stirred at the room temperature for one night. After the reaction was completed, separated crystals were dissolved by adding water. After the catalyst was removed by filtration, crystals were precipitated by adding concentrated hydrochloric acid. The crystals were separated by filtration and washed with water. The obtained crystals were dissolved in ethyl acetate and the organic layer was extracted. The extract was dried with magnesium sulfate and concentrated in vacuo using a rotary evaporator and 23.7 g (the yield: 98%) of Intermediate Compound H of the object compound was obtained.

Synthesis of Intermediate Compound I

In a 500 ml flask having an egg plant shape and equipped with a condenser, 23.7 g (98 mmole) of Intermediate Compound H and 200 ml of acetic anhydride were placed and the resulting mixture was stirred at 80° C. for 3 hours. After the reaction was completed, acetic anhydride in an excess amount was removed by distillation and 22 g (the yield: 10%) of Intermediate Compound I of the object compound was obtained.

Synthesis of Intermediate Compound J

In a 500 ml three-necked flask equipped with a condenser, 7.7 g (50 mmole) of biphenyl, 13.4 g (0.1 mole) of anhydrous aluminum chloride and 200 ml of 1,2-dichloroethane were placed under an argon stream and the resulting mixture was cooled to 0° C. To the cooled mixture, 22 g (98 mmole) of Intermediate Compound I was slowly added and the resulting mixture was stirred at 40° C. for 2 hours. After the reaction was completed, ice water was added to the reaction mixture and the resulting mixture was extracted with chloroform. The extract was dried with magnesium sulfate and concentrated in vacuo using a rotary evaporator and 19.0 g (the yield: 100%) of Intermediate Compound J of the object compound was obtained.

Synthesis of Intermediate Compound K

In a 500 ml flask having an egg plant shape and equipped with a condenser, 200 ml of polyphosphoric acid was placed and heated to 150° C. Then, 19 g (50 mmole) of Intermediate Compound J was added in small portions and the resulting mixture was stirred at the same temperature for 3 hours. After the reaction was completed, ice water was added to the reaction mixture and the resulting mixture was extracted with chloroform. The extract was dried with magnesium sulfate and concentrated in vacuo using a rotary evaporator. The obtained crude crystals were purified in accordance with the column chromatography (silica gel, chloroform/methanol=99/1) and 19 g (the yield: 55%) of Intermediate Compound K of the object compound was obtained.

Synthesis of Intermediate Compound L

In a 500 ml flask having an egg plant shape and equipped with a condenser, 19.0 g (28 mmole) of Intermediate Compound K, 0.19 g (1 mmole) of tin chloride, 100 ml of acetic acid and 50 ml of concentrated hydrochloric acid were placed under an argon stream and the resulting mixture was heated under refluxing for 2 hours. After the reaction was completed, the reaction mixture was cooled with ice water and precipitated crystals were separated, washed with water to give 19 g (the yield: 100%) of Intermediate Compound L of the object compound.

Synthesis of Intermediate Compound M

In a 500 ml three-necked flask equipped with a condenser, 19.0 g (28 mmole) of Intermediate Compound L, 16 g (60 mmole) of triphenylphosphine and 200 ml of dimethylformamide were placed under an argon stream. To this was added 9.6 g (60 mmole) of iodine dissolved in 50 ml of dimethylformamide slowly dropwise and the resulting mixture was stirred under heating at 200° C. for 8 hours. After the reaction was completed, the reaction mixture was cooled with ice water and precipitated crystals were separated. The obtained crystals were washed with water and methanol and 6.7 g (the yield: 50%) of Intermediate Compound M of the object compound was obtained.

Synthesis of Compound (100)

In a 200 ml three-necked flask equipped with a condenser, 4.9 g (10 mmole) of Intermediate Compound M, 5.1 g (30 mmole) of diphenylamine, 0.14 g (1.5% by mole) of tris(dibenzylideneacetone)dipalladium, 0.91 g (3% by mole) of tri-o-toluylphosphine, 2.9 g (30 mmole) of sodium t-butoxide and 50 ml of dry toluene were placed under an argon stream. The resulting mixture was stirred overnight under heating at 100° C. After the reaction was completed, precipitated crystals were separated by filtration and washed with 100 ml of methanol and 4.0 g of yellow powder was obtained. The obtained powder was identified to be Compound (100) by the measurements in accordance with NMR, IR and FD-MS (the yield: 60%).

The chemical structures of Intermediate Compounds and the route of synthesis of Compound (100) are shown in the following.

Synthesis of Intermediate Compound O

In a 500 ml three-necked flask equipped with a condenser, 10.7 g (40 mmole) of Intermediate Compound N and 200 ml of dry tetrahydrofuran were placed under an argon stream and the resulting mixture was cooled to −40° C. To the cooled mixture, 53 ml (80 mmole) of a 1.5 M hexane solution of phenyllithium was added slowly dropwise. After the addition was completed, the reaction mixture was stirred

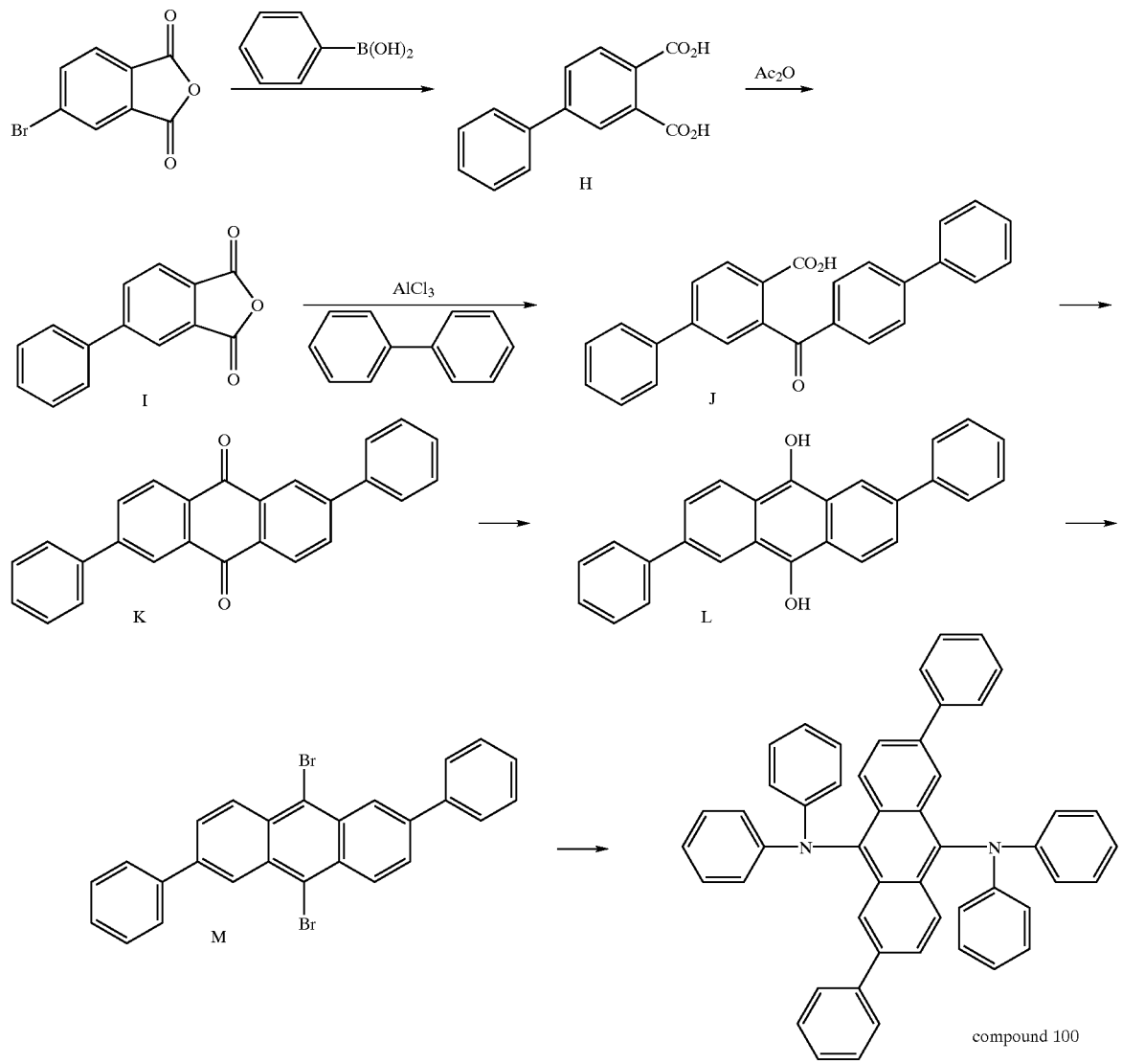

Synthesis Example 14 (Compound (101))

Synthesis of Intermediate Compound N

In a 500 ml flask having an egg plant shape and equipped with a condenser, 12 g (50 mmole) of 2,6-dihydroxyanthraquinone, 42.5 g (0.3 mole) of methyl iodide, 17 g (0.3 mole) of potassium hydroxide and 200 ml of dimethylsulfoxide were placed under an argon stream and the resulting mixture was stirred at the room temperature for 2 hours. After the reaction was completed, precipitated crystals were separated by filtration. The obtained crystals were washed with 100 ml of methanol and 10.7 g (the yield: 80%) of Intermediate Compound N of the object compound was obtained.

at the room temperature for one night. After the reaction was completed, precipitated crystals were separated by filtration and washed with 100 ml of methanol and 100 ml of acetone. The obtained crude crystals of a diol was used in the following reaction without further purification.

In a 500 ml flask having an egg plant shape and equipped with a condenser, the crude crystals obtained above, 100 ml of a 57% aqueous solution of hydrogen iodide and 200 ml of acetic acid were placed and the resulting mixture was heated under refluxing for 3 hours. After the reaction was cooled to the room temperature, a small amount of hypophosphorous acid was added to quench hydrogen iodide in an excess amount. Precipitated crystals were separated by filtration and washed with 100 ml of water, 100 ml of methanol and 100 ml of acetone, successively, and 10.1 g (the yield: 70%) of Intermediate Compound O of the object compound was obtained.

Synthesis of Intermediate Compound P

In a 500 ml flask having an egg plant shape and equipped with a condenser, 10.1 g (28 mmole) of Intermediate Compound O, 7.9 g (30 mmole) of triphenylphosphine and 200 ml of dimethylformamide were placed under an argon stream. To the resulting mixture, 4.8 g (30 mmole) of bromine dissolved in 50 ml of dimethylformamide was slowly added dropwise and the obtained mixture was stirred under heating at 200° C. for 8 hours. After the reaction was completed, the reaction mixture was cooled with ice water and precipitated crystals were separated by filtration. The obtained crystals were washed with water and methanol and 8.2 g (the yield: 60%) of Intermediate Compound P of the object compound was obtained.

Synthesis of Compound (101)

In a 200 ml three-necked flask equipped with a condenser, 4.9 g (30 mmole) of Intermediate Compound P, 5.1 g (30 mmole) of diphenylamine, 0.14 g (1.5% by mole) of tris(dibenzylideneacetone)dipalladium, 0.91 g (3% by mole) of tri-o-toluylphosphine, 2.9 g (30 mmole) of sodium t-butoxide and 50 ml of dry toluene were placed under an argon stream. The resulting mixture was stirred overnight under heating at 100° C. After the reaction was completed, precipitated crystals were separated by filtration and washed with 100 ml of methanol and 4.0 g of yellow powder was obtained. The obtained powder was identified to be Compound (101) by the measurements in accordance with NMR, IR and FD-MS (the yield: 60%).

The chemical structures of Intermediate Compounds and the route of synthesis of Compound (101) are shown in the following.

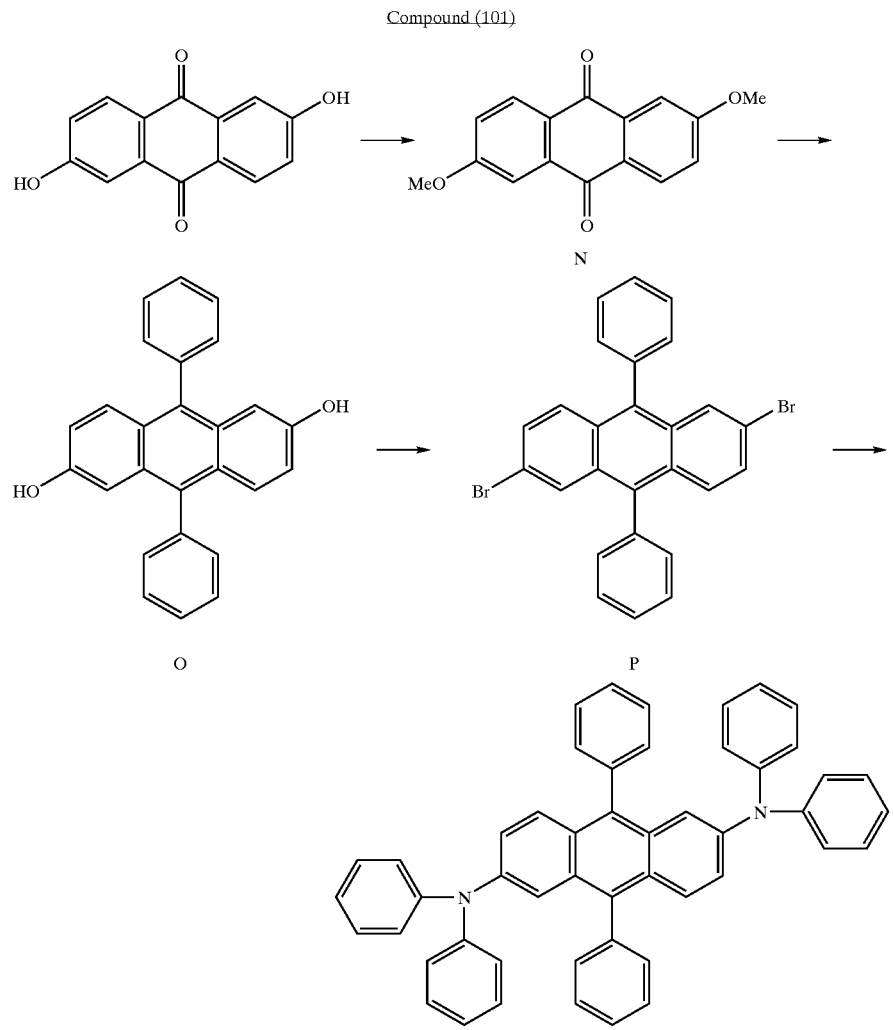

Synthesis Example 15 (Compound (93))

Synthesis of Intermediate Compound Q

In a 300 ml three-necked flask equipped with a condenser, 11.7 g (50 mmole) of 2-bromobiphenyl, 19 g (0.2 mole) of aniline, 0.69 g (1.5% by mole) of tris(dibenzylideneacetone)dipalladium, 0.46 g (3% by mole) of tri-o-toluylphosphine, 7.2 g (75 mmole) of sodium t-butoxide and 100 ml of dry toluene were placed under an argon stream. The resulting mixture was stirred overnight under heating at 100° C. After the reaction was completed, precipitated crystals were separated by filtration and washed with 100 ml of methanol. The obtained crude crystals were recrystallized from 50 ml of ethyl acetate and 9.8 g (the yield: 80%) of Intermediate Compound Q of the object compound was obtained.

Synthesis of Compound (93)

In a 200 ml three-necked flask equipped with a condenser, 2.4 g (10 mmole) of 9,10-dibromoanthracene, 7.4 g (30 mmole) of Intermediate Compound Q, 0.14 g (1.5% by mole) of tris(dibenzylidene-acetone)dipalladium, 0.91 g (3% by mole) of tri-o-toluylphosphine, 2.9 g (30 mmole) of sodium t-butoxide and 50 ml of dry toluene were placed under an argon stream. The resulting mixture was stirred overnight under heating at 100° C. After the reaction was completed, precipitated crystals were separated by filtration and washed with 100 ml of methanol and 4.3 g of yellow powder was obtained. The obtained powder was identified to be Compound (93) by the measurements in accordance with NMR, IR and FD-MS (the yield: 65%).

The chemical structure of Intermediate Compound and the route of synthesis of Compound (93) are shown in the following.

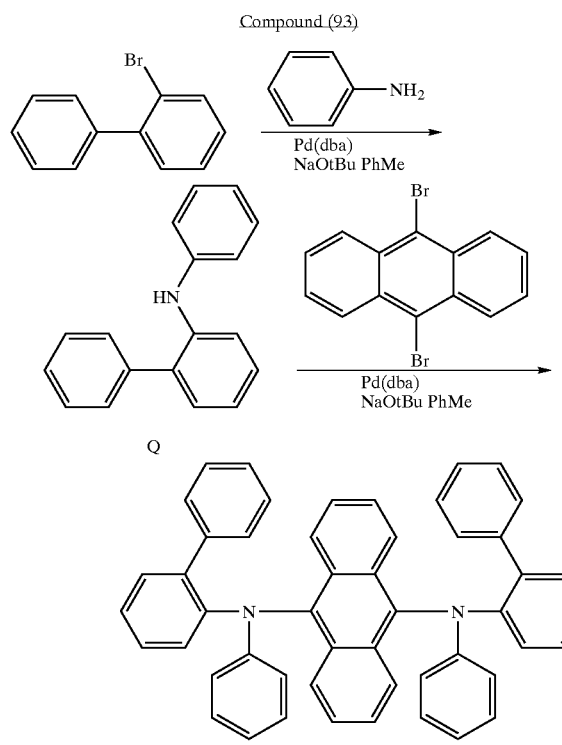

Synthesis Example 16 (Compound (95))

Synthesis of Intermediate Compound R

In a 1 liter three-necked flask equipped with a condenser, 34 g (0.2 mole) of 3-phenylphenol, 58 g (0.22 mmole) of triphenylphosphine and 300 ml of dimethylformamide were placed under an argon stream. To the resulting mixture, 35 g (0.22 mmole) of bromine dissolved in 100 ml of dimethylformamide was slowly added dropwise and the obtained mixture was stirred at 200° C. for 8 hours. After the reaction was completed, the reaction mixture was cooled with ice water and precipitated crystals were separated by filtration. The obtained crystals were washed with water and methanol and 37 g (the yield: 80%) of Intermediate Compound R of the object compound was obtained.

Synthesis of Intermediate Compound S

In a 300 ml three-necked flask equipped with a condenser, 19 g (0.2 mmole) of aniline, 0.69 g (1.5% by mole) of tris(dibenzylidene-acetone)dipalladium, 0.46 g (3% by mole) of tri-o-toluylphosphine, 7.2 g (75 mmole) of sodium t-butoxide and 100 ml of dry toluene were placed under an argon stream. The resulting mixture was stirred overnight under heating at 100° C. After the reaction was completed, precipitated crystals were separated by filtration and washed with 100 ml of methanol. The obtained crude crystals were recrystallized from 50 ml of ethyl acetate and 9.8 g (the yield: 80%) of Intermediate Compound S of the object compound was obtained.

Synthesis of Compound (95)

In a 200 ml three-necked flask equipped with a condenser, 2.4 g (10 mmole) of 9,10-dibromoanthracene, 7.4 g (30 mmole) of Intermediate Compound S, 0.14 g (1.5% by mole) of tris(dibenzylidene-acetone)dipalladium, 0.91 g (3% by mole) of tri-o-toluylphosphine, 2.9 g (30 mmole) of sodium t-butoxide and 50 ml of dry toluene were placed under an argon stream. The resulting mixture was stirred overnight under heating at 100° C. After the reaction was completed, precipitated crystals were separated by filtration and washed with 100 ml of methanol and 4.2 g of yellow powder was obtained. The obtained powder was identified to be Compound (95) by the measurements in accordance with NMR, IR and FD-MS (the yield: 70%).

The chemical structures of Intermediate Compounds and the route of synthesis of Compound (95) are shown in the following.

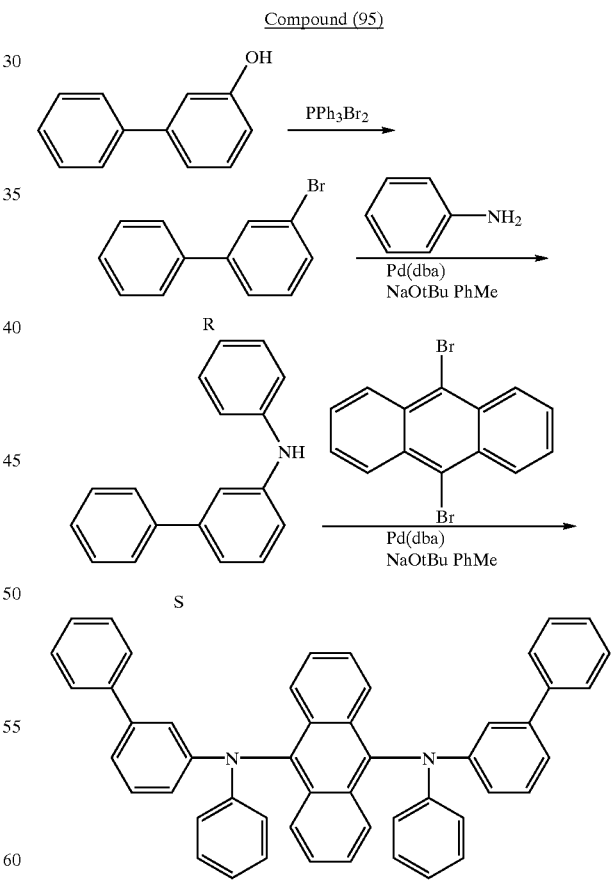

Synthesis Example 17 (Compound (104))

Synthesis of Intermediate Compound T

In a 300 ml three-necked flask equipped with a condenser, 23 g (0.1 mole) of 4-bromobiphenyl, 9.8 g (50 mmole) of aminostilbene, 0.69 g (1.5% by mole) of tris(dibenzylideneacetone)dipalladium, 0.46 g (3% by mole) of tri-o-toluylphosphine, 7.2 g (75 mmole) of sodium t-butoxide and 100 ml of dry toluene were placed under an argon stream. The resulting mixture was stirred overnight under heating at 100° C. After the reaction was completed, precipitated crystals were separated by filtration and washed with 100 ml of methanol. The obtained crude crystals were recrystallized from 50 ml of ethyl acetate and 13.9 g (the yield: 80%) of Intermediate Compound T of the object compound was obtained.

Synthesis of Compound (104)

Into a 200 ml three-necked flask equipped with a condenser, 2.4 g (10 mmole) of 9,10-dibromoanthracene, 7.4 g (30 mmole) of Intermediate Compound T, 0.14 g (1.5% by mole) of tris(dibenzylidene-acetone)dipalladium, 0.91 g (3% by mole) of tri-o-toluylphosphine, 2.9 g (30 mmole) of sodium t-butoxide and 50 ml of dry toluene were placed under an argon stream. The resulting mixture was stirred overnight under heating at 100° C. After the reaction was completed, precipitated crystals were separated by filtration and washed with 100 ml of methanol and 4.5 g of yellow powder was obtained. The obtained powder was identified to be Compound (104) by the measurements in accordance with NMR, IR and FD-MS (the yield: 70%).

The chemical structure of Intermediate Compound and the route of synthesis of Compound (104) are shown in the following.

Synthesis Example 18 (Compound (105))

Synthesis of Intermediate Compound U

In a 500 ml three-necked flask equipped with a condenser, 25 g (0.1 mole) of triphenylamine, 18 g (0.1 mole) of N-bromosuccimide, 0.82 g (5% by mole) of 2,2'-azobisisobutyronitrile and 200 ml of dimethylformamide were placed under an argon stream. The resulting mixture was stirred under heating at 110° C. for 4 hours. After the reaction was completed, impurities were removed by filtration and the filtrate was concentrated in vacuo using a rotary evaporator. The obtained crude crystals were purified in accordance with the column chromatography (silica gel, methylene chloride) and 19 g (the yield: 60%) of Intermediate Compound U of the object compound was obtained.

Synthesis of Intermediate Compound V

In a 1 liter three-necked flask equipped with a condenser, 1.6 g (66 mmole) of magnesium, a small piece of iodine and 100 ml of tetrahydrofuran were placed under an argon stream. After the resulting mixture was stirred at the room temperature for 30 minutes, 19 g (60 mole) of Intermediate Compound U dissolved in 300 ml of tetrahydrofuran was added dropwise. After the addition was completed, the reaction mixture was stirred under heating at 60° C. for 1 hour and a Grignard reagent was prepared.

In a 1 liter three-necked flask equipped with a condenser, 42 g (0.18 mmole) of 1,3-dibromobenzene, 2.1 (5% by mole) of dichlorobis(triphenylphosphine)palladium, 6 ml (6 mmole) of a 1 M toluene solution of diisobutylaluminum

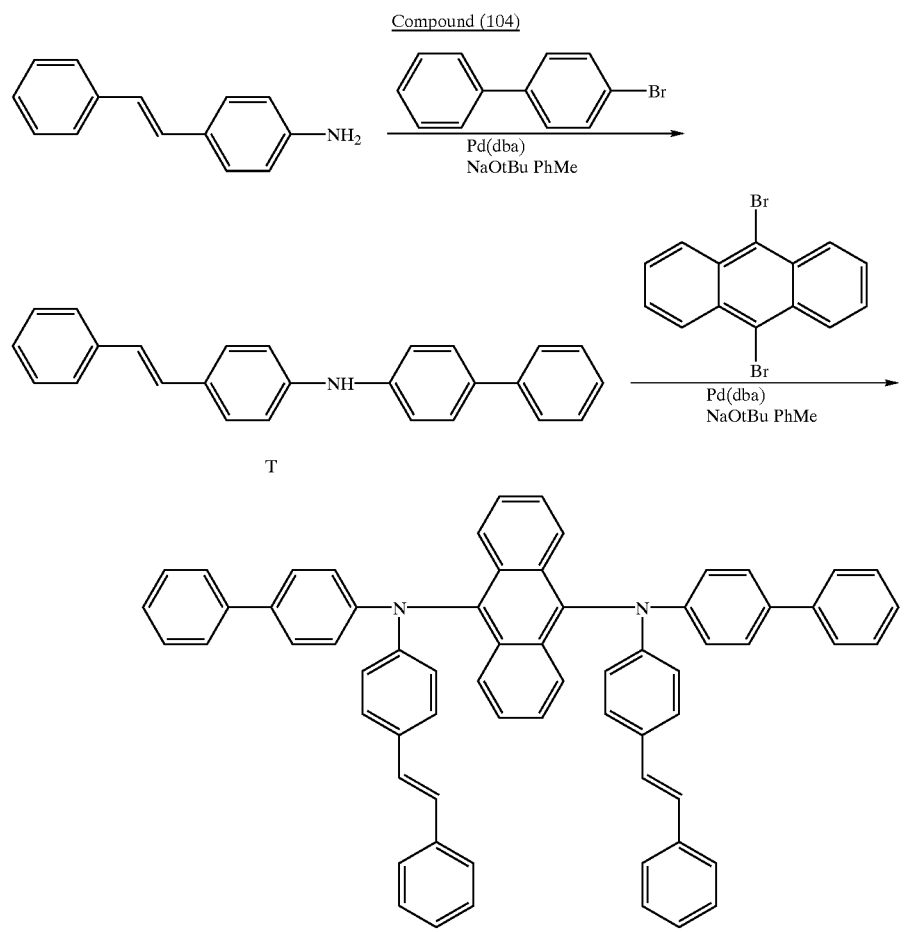

hydride and 200 ml of tetrahydrofuran were placed under an argon stream. To the mixture, the Grignard reagent prepared above was added dropwise and the obtained mixture was stirred under heating for one night. After the reaction was completed, the reaction liquid was cooled with ice water. Precipitated crystals were separated by filtration and washed with acetone and 14 g (the yield: 60%) of Intermediate Compound V of the object compound was obtained.

Synthesis of Compound (105)

In a 500 ml three-necked flask equipped with a condenser, 0.8 g (33 mmole) of magnesium, a small piece of iodine and 50 ml of tetrahydrofuran were placed under an argon stream. After the resulting mixture was stirred at the room temperature for 30 minutes, 12 g (30 mmole) of Intermediate Compound V dissolved in 100 ml of tetrahydrofuran was added dropwise. After the addition was completed, the reaction mixture was stirred under heating at 60° C. for 1 hour and a Grignard reagent was prepared.

In a 500 ml three-necked flask equipped with a condenser, 3.4 g (10 mmole) of 9,10-dibromoanthracene, 0.4 (5% by mole) of dichlorobis(triphenylphosphine)palladium, 0.46 g (3% by mole) of tri-o-toluylphosphine, 1 ml (1 mmole) of a 1 M toluene solution of diisobutylaluminum hydride and 100 ml of tetrahydrofuran were placed under an argon stream. To the obtained mixture, the Grignard reagent prepared above was added dropwise at the room temperature and the resulting mixture was refluxed overnight. After the reaction was completed, the reaction liquid was cooled with ice water. Precipitated crystals were separated by filtration and washed with 50 ml of methanol and 50 ml of acetone, successively, and 4.1 g of yellow powder was obtained. The obtained powder was identified to be Compound (105) by the measurements in accordance with NMR, IR and FD-MS (the yield: 50%).

The chemical structures of Intermediate Compounds and the route of synthesis of Compound (105) are shown in the following.

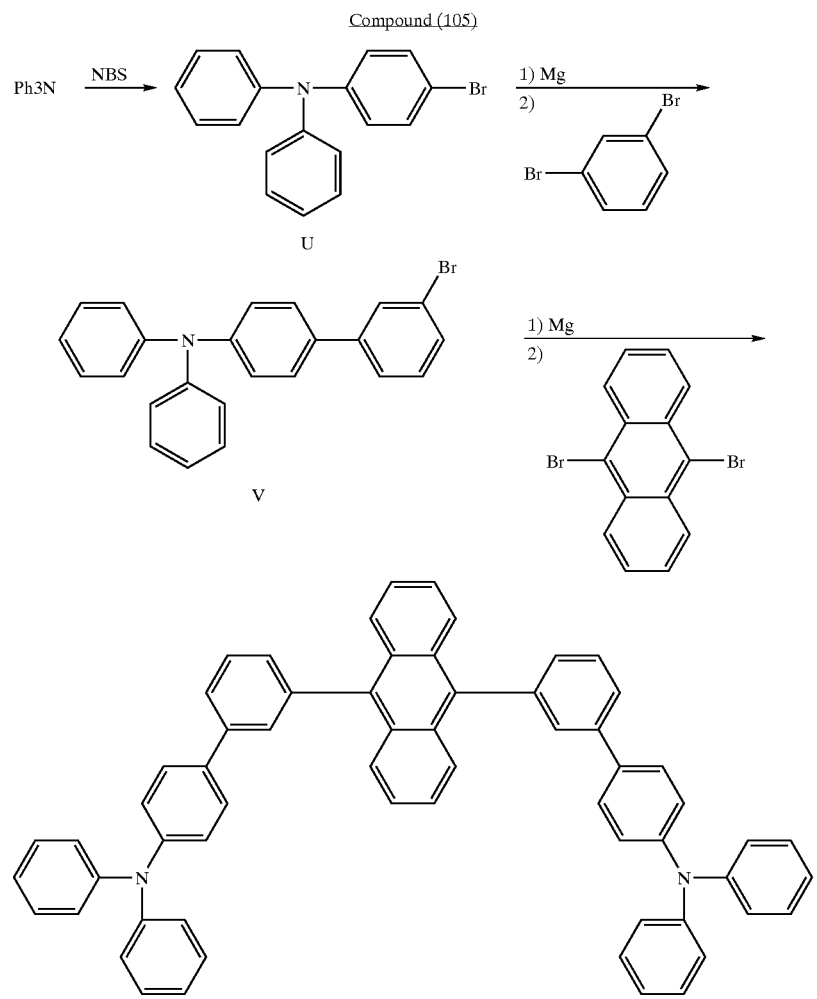

Synthesis Example 19 (Compound (122))

Synthesis of Intermediate Compound W

In a 300 ml three-necked flask equipped with a condenser, 19 g (80 mmole) of 1,3-dibromobenzene, 6.5 g (20 mmole) of diphenylamine, 0.27 g (1.5% by mole) of tris (dibenzylideneacetone)dipalladium, 0.18 g (3% by mole) of tri-o-toluylphosphine, 2.9 g (30 mmole) of sodium t-butoxide and 100 ml of dry toluene were placed under an argon stream. The resulting mixture was stirred overnight under heating at 100° C. After the reaction was completed, precipitated crystals were separated by filtration and washed with 100 ml of methanol. The obtained crude crystals were recrystallized from 50 ml of ethyl acetate and 4.9 g (the yield: 75%) of Intermediate Compound W of the object compound was obtained.

Synthesis of Compound (122)

In a 300 ml three-necked flask equipped with a condenser, 0.5 g (20 mmole) of magnesium, a small piece of iodine and 50 ml of tetrahydrofuran were placed under an argon stream. After the resulting mixture was stirred at the room temperature for 30 minutes, 4.9 g (15 mmole) of Intermediate Compound W dissolved in 100 ml of tetrahydrofuran was added dropwise. After the addition was completed, the reaction mixture was stirred under heating at 60° C. for 1 hour and a Grignard reagent was prepared.

In a 500 ml three-necked flask equipped with a condenser, 1.7 g (5 mmole) of 9,10-dibromoanthracene, 0.2 g (5% by mole) of dichlorobis(triphenylphosphine)palladium, 0.5 ml (0.5 mmole) of a 1 M toluene solution of diisobutylaluminum hydride and 100 ml of tetrahydrofuran were placed under an argon stream. To the mixture, the Grignard reagent prepared above was added dropwise at the room temperature and the resulting mixture was stirred overnight under heating. After the reaction was completed, the reaction liquid was cooled with ice water. Precipitated crystals were separated by filtration and washed with 50 ml of methanol and 50 ml of acetone, successively, and 1.7 g of yellow powder was obtained. The obtained powder was identified to be Compound (122) by the measurements in accordance with NMR, IR and FD-MS (the yield: 50%).

The chemical structure of Intermediate Compound and the route of synthesis of Compound (122) are shown in the following.

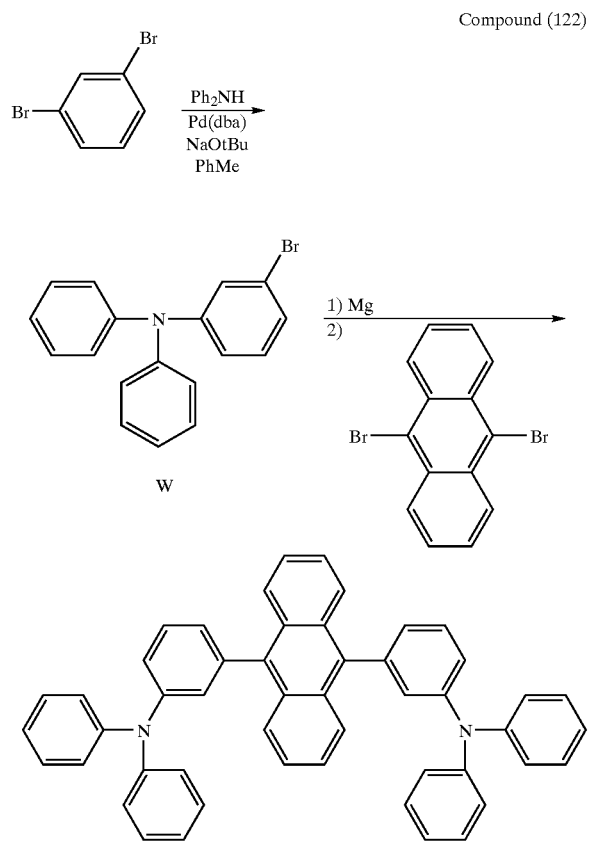

Compound (122)

Synthesis Example 20 (Compound (123))

Synthesis of Intermediate Compound X

In a 300 ml three-necked flask equipped with a condenser, 16 g (0.1 mole) of bromobenzene, 9.8 g (50 mmole) of aminostilbene, 0.69 g (1.5% by mole) of tris(dibenzylideneacetone)dipalladium, 0.46 g (3% by mole) of tri-o-toluylphosphine, 7.2 g (75 mmole) of sodium t-butoxide and 100 ml of dry toluene were placed under an argon stream. The resulting mixture was stirred overnight under heating at 100° C. After the reaction was completed, precipitated crystals were separated by filtration and washed with 100 ml of methanol. The obtained crude crystals were recrystallized from 50 ml of ethyl acetate and 11 g (the yield: 80%) of Intermediate Compound X of the object compound was obtained.

Synthesis of Intermediate Compound Y

In a 500 ml three-necked flask equipped with a condenser, 38 g (0.16 mole) of bromobenzene, 11 g (40 mmole) of Intermediate Compound X, 0.55 g (1.5% by mole) of tris(dibenzylideneacetone)-dipalladium, 0.37 g (3% by mole) of tri-o-toluylphosphine, 5.8 g (60 mmole) of sodium t-butoxide and 300 ml of dry toluene were placed under an argon stream. The resulting mixture was stirred overnight under heating at 120° C. After the reaction was completed, precipitated crystals were separated by filtration and washed with 100 ml of methanol. The obtained crude crystals were recrystallized from 50 ml of ethyl acetate and 13 g (the yield: 75%) of Intermediate Compound Y of the object compound was obtained.

Synthesis of Compound (123)

In a 300 ml three-necked flask equipped with a condenser, 0.97 g (40 mmole) of magnesium, a small piece of iodine and 50 ml of tetrahydrofuran were placed under an argon stream. After the resulting mixture was stirred at the room temperature for 30 minutes, 12 g (30 mole) of Intermediate Compound Y dissolved in 100 ml of tetrahydrofuran was added dropwise. After the addition was completed, the reaction mixture was stirred under heating at 60° C. for 1 hour and a Grignard reagent was prepared.

In a 500 ml three-necked flask equipped with a condenser, 3.4 g (10 mmole) of 9,10-dibromoanthracene, 0.4 g (5% by mole) of dichlorobis(triphenylphosphine)palladium, 1 ml (1 mmole) of a 1 M toluene solution of diisobutylaluminum hydride and 100 ml of tetrahydrofuran were placed under an argon stream. To the obtained mixture, the Grignard reagent prepared above was added dropwise at the room temperature and the resulting mixture was refluxed overnight. After the reaction was completed, the reaction liquid was cooled with ice water. Precipitated crystals were separated by filtration and washed with 50 ml of methanol and 50 ml of acetone, successively, and 5.4 g of yellow powder was obtained. The obtained powder was identified to be Compound (123) by the measurements in accordance with NMR, IR and FD-MS (the yield: 50%).

The chemical structures of Intermediate Compounds and the route of synthesis of Compound (123) are shown in the following.

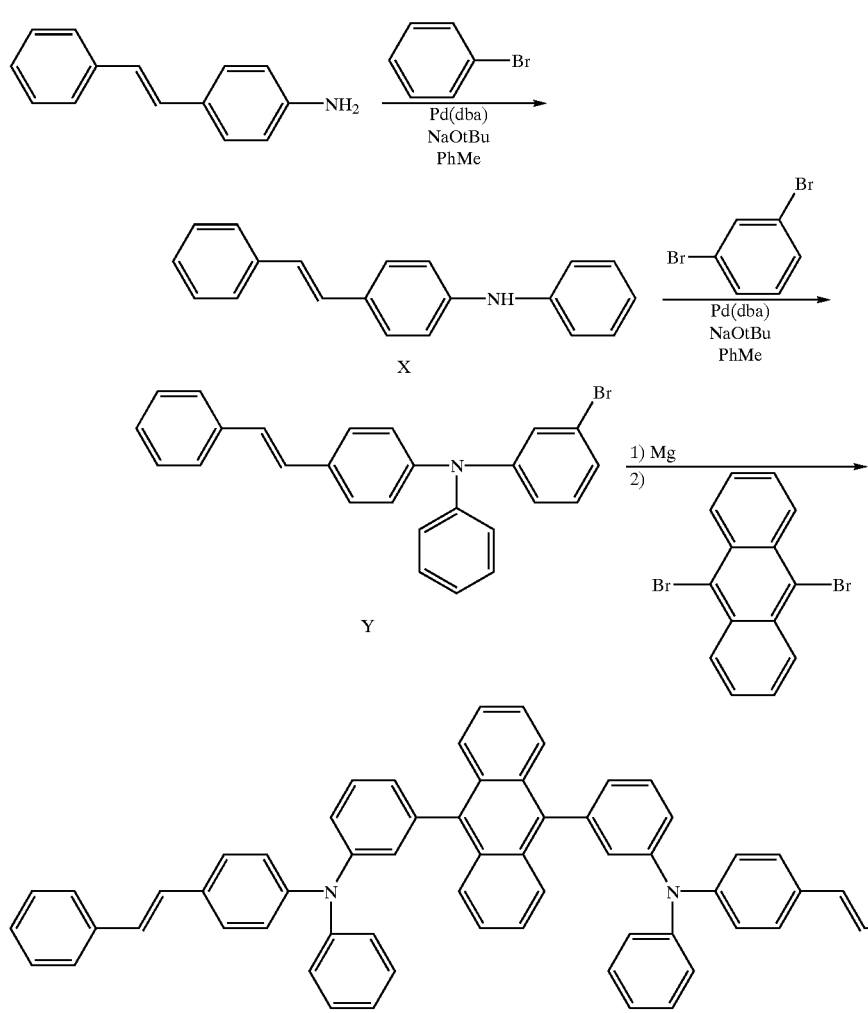

Compound (123)

Synthesis Example 21 (Compound (124))

Synthesis of Compound (124)

In a 500 ml three-necked flask equipped with a condenser, 2.5 g (5 mmole) of 10,10'-dibromo-9,9'-bianthryl, 0.2 g (5% by mole) of dichlorobis(triphenylphosphine)palladium, 0.5 ml (0.5 mmole) of a 1 M toluene solution of diisobutylaluminum hydride and 100 ml of tetrahydrofuran were placed under an argon stream. To the mixture, the Grignard reagent prepared in Synthesis Example 19 was added dropwise at the room temperature and the resulting mixture was refluxed overnight. After the reaction was completed, the reaction liquid was cooled with ice water. Precipitated crystals were separated by filtration and washed with 50 ml of methanol and 50 ml of acetone, successively, and 2.0 g of yellow powder was obtained. The obtained powder was identified to be Compound (124) by the measurements in accordance with NMR, IR and FD-MS (the yield: 60%).

The route of synthesis of Compound (124) is shown in the following.

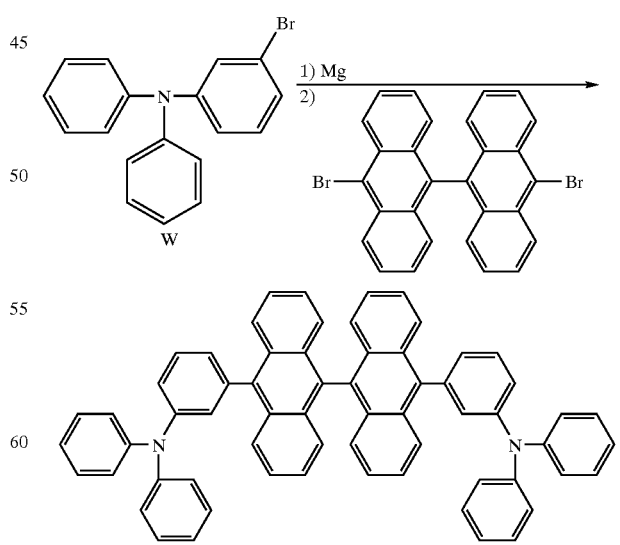

Compound (124)

Synthesis Example 22 (Compound (125))

Synthesis of Compound (125)

In a 500 ml three-necked flask equipped with a condenser, 1.9 g (5 mmole) of 6,12-dibromochrysene, 0.2 g (5% by mole) of dichlorobis(triphenylphosphine)palladium, 0.5 ml (0.5 mmole) of a 1 M toluene solution of diisobutylaluminum hydride and 100 ml of tetrahydrofuran were placed under an argon stream. To the mixture, the Grignard reagent prepared in Synthesis Example 19 was added dropwise at the room temperature and the resulting mixture was stirred under heating overnight. After the reaction was completed, the reaction liquid was cooled with ice water. Precipitated crystals were separated by filtration and washed with 50 ml of methanol and 50 ml of acetone, successively, and 2.1 g of yellow powder was obtained. The obtained powder was identified to be Compound (125) by the measurements in accordance with NMR, IR and FD-MS (the yield: 60%).

The route of synthesis of Compound (125) is shown in the following.

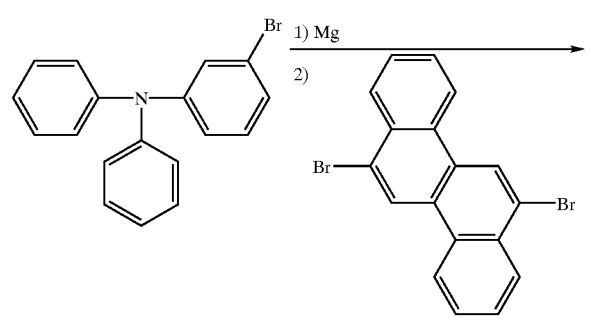

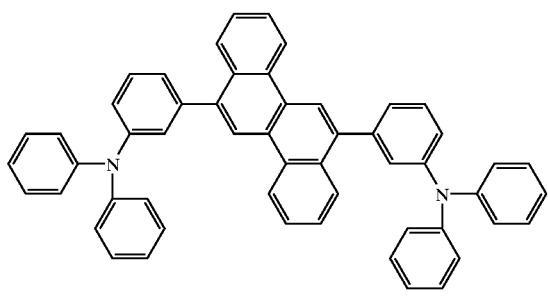

Compound (125)

Synthesis Example 23 (Compound (126))

Synthesis of Compound (126)

In a 500 ml three-necked flask equipped with a condenser, 1.9 g (5 mmole) of 5,12-dibromonaphthacene, 0.2 g (5% by mole) of dichlorobis(triphenylphosphine)palladium, 0.5 ml (0.5 mmole) of a 1 M toluene solution of diisobutylaluminum hydride and 100 ml of tetrahydrofuran were placed under an argon stream. To the mixture, the Grignard reagent prepared in Synthesis Example 19 was added dropwise at the room temperature and the resulting mixture was stirred under heating overnight. After the reaction was completed, the reaction liquid was cooled with ice water. Precipitated crystals were separated by filtration and washed with 50 ml of methanol and 50 ml of acetone, successively, and 2.1 g of yellow powder was obtained. The obtained powder was identified to be Compound (126) by the measurements in accordance with NMR, IR and FD-MS (the yield: 60%).

The route of synthesis of Compound (126) is shown in the following.

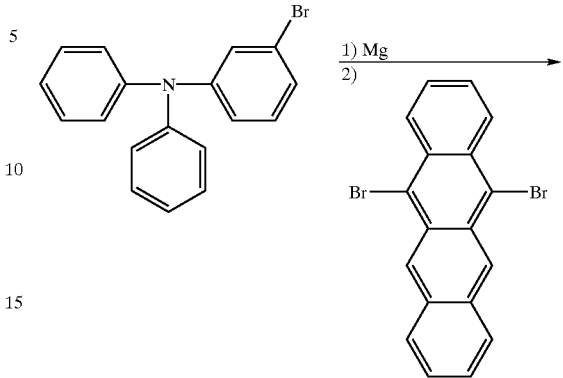

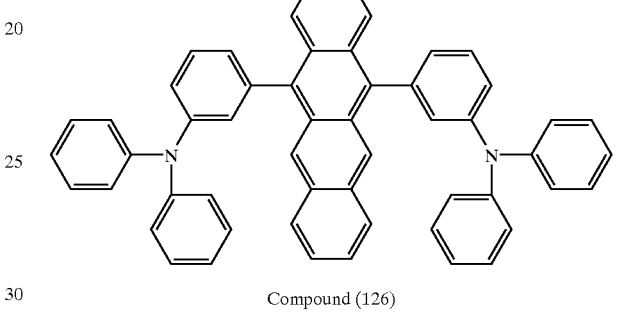

Compound (126)

EXAMPLE 52

On a glass substrate having a size of 25 mm×75 mm×1.1 mm, a transparent anode of a film of indium tin oxide having a thickness of 100 nm was formed and cleaned for 10 minutes by using ultraviolet light and ozone in combination.

This glass substrate was placed into an apparatus for vacuum vapor deposition (manufactured by NIPPON SHINKUU GIJUTU Co., Ltd.) and the pressure was reduced to about $10^{-4}$ Pa. TPD74 described above was vapor deposited at a speed of 0.2 nm/second and a layer having a thickness of 60 nm was formed. Then, TPD78 having the structure shown below was vapor deposited at a speed of 0.2 nm/second and a layer having a thickness of 20 nm was formed.

On the layer formed above, DPVDPAN having the structure shown below and Compound (100) described above as the light emitting material were simultaneously vapor deposited and a light emitting layer having a thickness of 40 nm was formed. The speed of vapor deposition of DPVDPAN was 0.4 nm/second and the speed of vapor deposition of Compound (100) was 0.01 nm/second. On the layer formed above, Alq described above was vapor deposited at a speed of 0.2 nm/second. Finally, aluminum and lithium were vapor deposited simultaneously and a cathode having a thickness of 150 nm was formed. Thus, an organic EL device was obtained. The speed of vapor deposition of aluminum was 1 nm/second and the speed of vapor deposition of lithium was 0.004 nm/second.

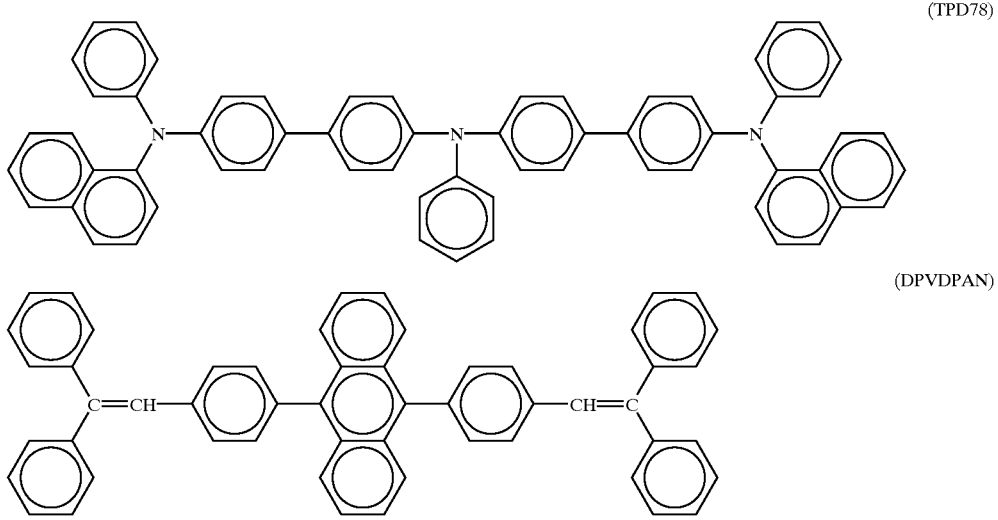

(TPD78)

(DPVDPAN)

The properties of the obtained organic EL device were evaluated. Luminance of emitted light at the voltage shown in Table 4 was measured and the efficiency of light emission was calculated. The color of emitted light was observed. The organic EL device was driven by a constant electric current under a nitrogen stream at an initial luminance of emitted light of 500 (cd/m$^2$) and the half life time which was the time before the luminance decreases to 250 (cd/m$^2$) was measured. The results are shown in Table 4.

EXAMPLES 53 to 62

Organic EL devices were prepared in accordance with the same procedures as those conducted in Example 52 except that the compounds shown in Table 4 were used as the light emitting material in place of Compound (100) and the properties were evaluated. The results are shown in Table 4.

Comparative Example 8

An organic EL devices was prepared in accordance with the same procedures as those conducted in Example 52 except that the diamine compound shown below was used as the light emitting material in place of Compound (100) and the properties were evaluated. The results are shown in Table 4.

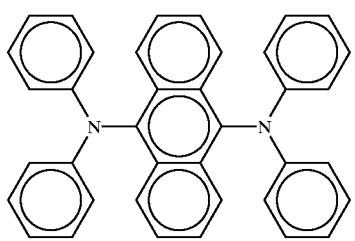

TABLE 4

| | Voltage (V) | Luminance of emitted light (cd/m$^2$) | Efficiency of light emission (lm/W) | Half life time (hour) | Color of emitted light |
|---|---|---|---|---|---|
| Example | | | | | |
| 52 | 6.0 | 120 | 4.50 | 1800 | green |
| 53 | 6.0 | 240 | 3.90 | 2000 | bluish green |
| 54 | 6.0 | 130 | 4.60 | 1700 | green |
| 55 | 6.0 | 210 | 4.90 | 2500 | green |
| 56 | 7.0 | 230 | 4.00 | 1500 | yellowish green |
| 57 | 6.0 | 120 | 2.90 | 2100 | blue |
| 58 | 6.0 | 180 | 3.40 | 1800 | bluish green |
| 59 | 5.5 | 220 | 4.62 | 1700 | blue |
| 60 | 5.5 | 420 | 3.10 | 2200 | bluish green |
| 61 | 5.5 | 180 | 4.25 | 3100 | blue |
| 62 | 5.0 | 240 | 4.90 | 3200 | bluish green |
| Comparative Example | | | | | |
| 8 | 6.0 | 150 | 3.70 | 1200 | green |

As shown in Table 4, the organic EL devices of Examples 52 to 62 in which the compounds represented by general formulae [9] and [10] of the present invention were used as the light emitting material or the hole transporting material exhibited more excellent luminance of emitted light and efficiencies of light emission and longer lives in comparison with the organic EL device of Comparative Example 8 in which the diamine compound was used.

Synthesis Example 24 (Compound a)

Synthesis of Intermediate Compound A

In a 500 ml three-necked flask, 50 g (0.27 mole) of p-bromobenzaldehyde, 50 g (0.22 mmole) of diethyl benzylphosphonate and 200 ml of dimethylsulfoxide were placed under an argon stream. To this was added 30 g (0.27 mole) of potassium t-butoxide in small portions. The resulting mixture was stirred overnight at the room temperature. After the reaction was completed, the reaction liquid was poured into 500 ml of water and extracted with ethyl acetate. The extract was dried with magnesium sulfate and concentrated in vacuo using a rotary evaporator. The obtained crude crystals were recrystallized from 100 ml of ethyl acetate and 46 g (the yield: 81%) of Intermediate Compound A was obtained.

Synthesis of Intermediate Compound B

Into a 300 ml three-necked flask equipped with a condenser, 10 g (38 mmole) of Intermediate Compound A, 14 g (150 mmole) of aniline, 0.53 g (1.5% by mole) of tris(dibenzylideneacetone)dipalladium, 0.35 g (3% by mole) of tri-o-toluylphosphine, 7.4 g (77 mole) of sodium t-butoxide and 100 ml of dry toluene were placed under an argon stream. The resulting mixture was stirred overnight under heating at 100° C. After the reaction was completed, precipitated crystals were separated by filtration and washed with 100 ml of methanol. The obtained crude crystals were recrystallized from 50 ml of ethyl acetate and 7.7 g (the yield: 73%) of Intermediate Compound B was obtained.

Synthesis of Intermediate Compound C

In a 100 ml flask having an egg plant shape and equipped with a condenser, 12.5 g (50 mmole) of 4-bromobenzyl bromide and 12.5 (75 mmole) of triethyl phosphite were placed. The resulting mixture was stirred under heating at 100° C. for 7 hours. After the reaction was completed, triethyl phosphite in an excess amount was removed by distillation in vacuo and 15.4 g of Intermediate Compound C was obtained. Intermediate Compound C was used in the following reaction without further purification.

Synthesis of Intermediate Compound D

In a 300 ml three-necked flask, 9.2 g (50 mmole) of p-bromobenzaldehyde, 15.4 g (50 mmole) of Intermediate Compound C and 100 ml of dimethylsulfoxide were placed under an argon stream. To this was added 6.7 g (60 mmole) of potassium t-butoxide in small portions and the resulting mixture was stirred overnight at the room temperature. After the reaction was completed, the reaction liquid was poured into 200 ml of water and extracted with ethyl acetate. The extract was dried with magnesium sulfate and concentrated in vacuo using a rotary evaporator. The obtained crystals were washed with 100 ml of methanol and 13 g (the yield: 77%) of Intermediate compound D was obtained.

Synthesis of Compound a

In a 200 ml three-necked flask equipped with a condenser, 4 g (15 mmole) of Intermediate Compound B, 2 g (6 mmole) of Intermediate Compound D, 0.16 g (3% by mole) of tris(dibenzylideneacetone)dipalladium, 0.22 g (6% by mole) of (S)-BINAP, 1.4 g (15 mmole) of sodium t-butoxide and 50 ml of dry toluene were placed under an argon stream. The resulting mixture was stirred overnight under heating at 100° C. After the reaction was completed, precipitated crystals were separated by filtration, washed with methanol and dried by heating at 60° C. for one night. The obtained crude crystals were purified in accordance with the column chromatography (silica gel, hexane/toluene=8/2) and 1.4 g of yellow powder was obtained. The obtained powder was identified to be Compound a by the measurements in accordance with NMR, IR and FD-MS (the field desorption mass spectroscopy) (the yield: 32%, in $^1H_{NMR}$ (90 Hz): δ 7.0~7.4 ppm (42H, m)). The NMR chart of Compound a is shown in FIG. 1.

The chemical reactions to obtain Compound a are shown in the following:

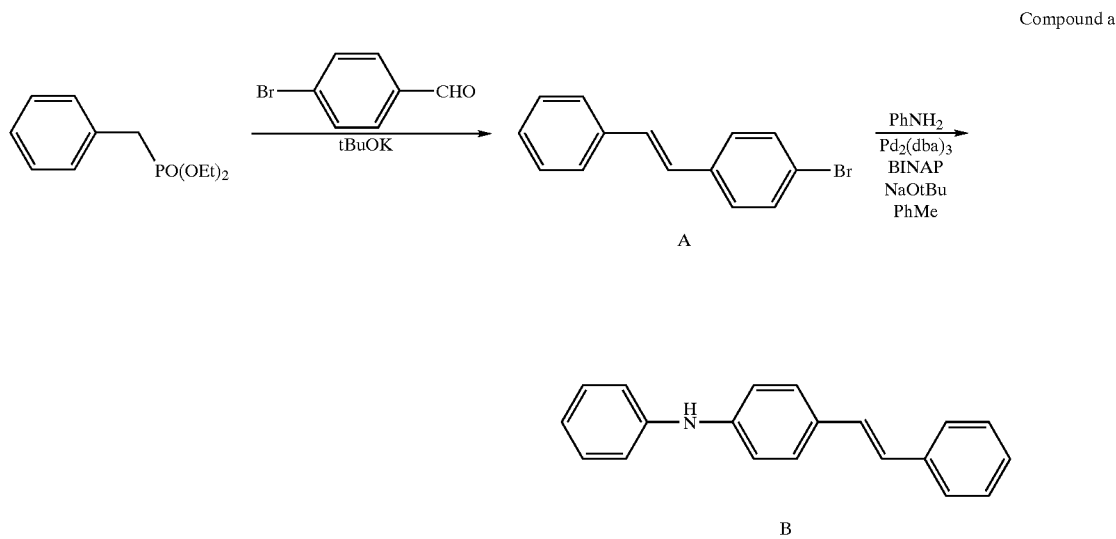

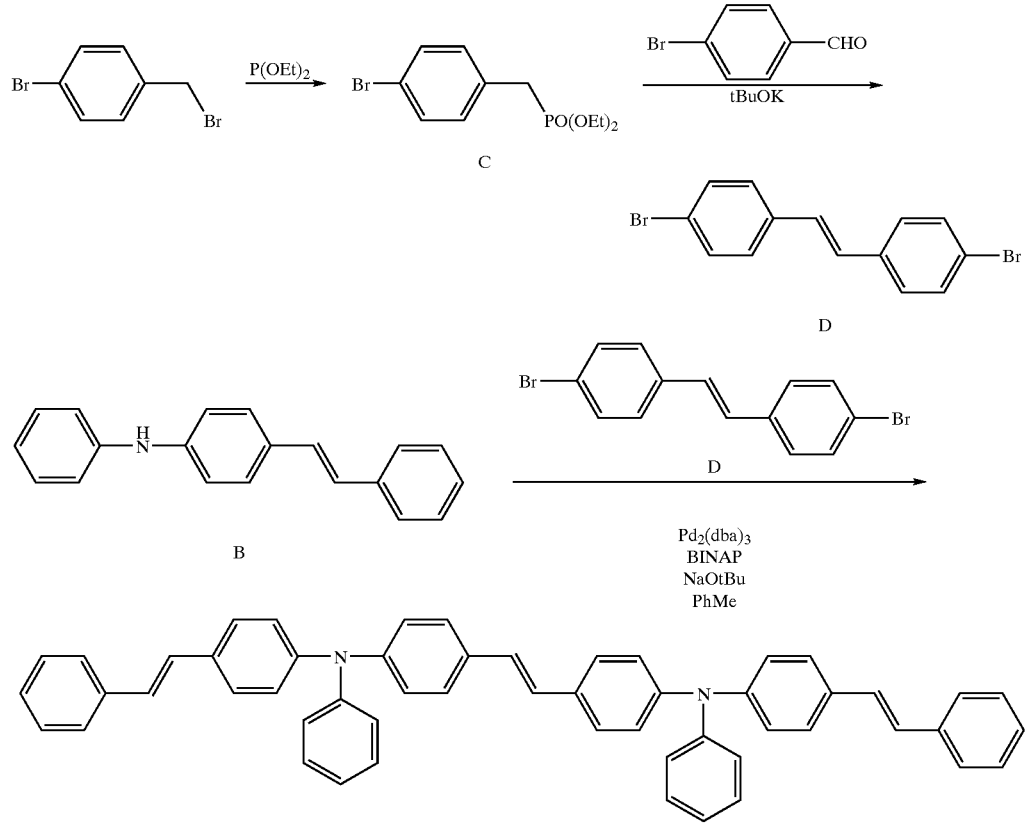

Synthesis Example 25 (Compound b)

Synthesis of Intermediate Compound E

In a 300 ml three-necked flask, 6 g (50 mmole) of p-tolualdehyde, 15.4 g (50 mmole) of Intermediate Compound C and 100 ml of dimethylsulfoxide were placed under an argon stream. To this was added 6.7 g (60 mmole) of potassium t-butoxide in small portions and the resulting mixture was stirred overnight at the room temperature. After the reaction was completed, the reaction liquid was poured into 200 ml of water and extracted with ethyl acetate. The extract was dried with magnesium sulfate and concentrated in vacuo using a rotary evaporator. The obtained crystals were washed with 100 ml of methanol and 9.2 g (the yield: 67%) of Intermediate Compound E was obtained.

Synthesis of Compound b

Figure 2:
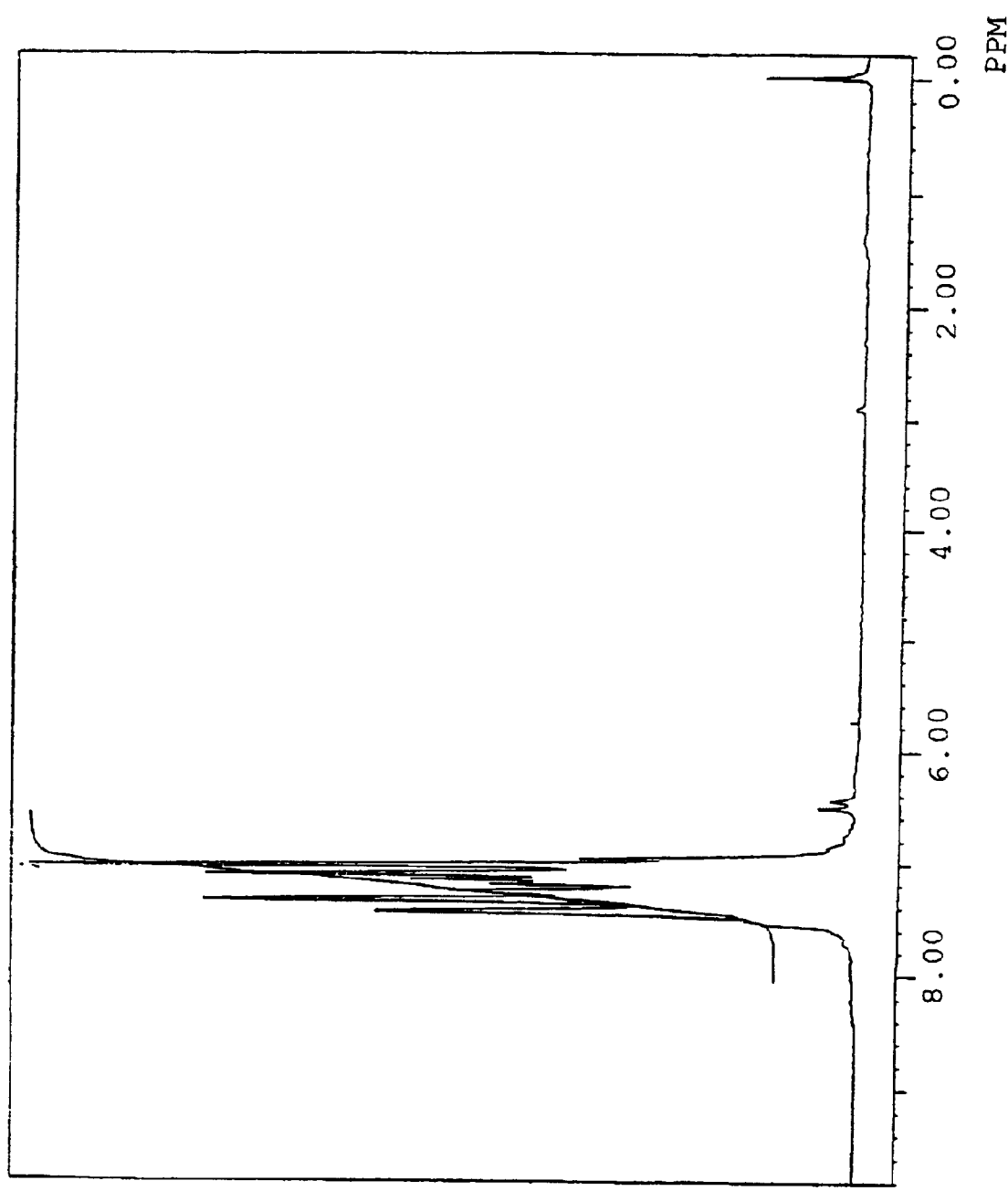
FIG. 2 shows a $^1H_{NMR}$ chart of compound b synthesized in accordance with the process of the present invention.

In a 200 ml three-necked flask equipped with a condenser, 4 g (15 mmole) of Intermediate Compound E, 2 g (6 mmole) of N,N'-diphenylbenzidine, 0.16 g (3% by mole) of tris(dibenzylideneacetone)dipalladium, 0.22 g (6% by mole) of (S)-BINAP, 1.4 g (15 mmole) of sodium t-butoxide and 50 ml of dry toluene were placed under an argon stream. The resulting mixture was stirred overnight under heating at 100° C. After the reaction was completed, precipitated crystals were separated by filtration, washed with methanol and dried by heating at 60° C. for one night. The obtained crude crystals were purified in accordance with the column chromatography (silica gel, hexane/toluene=8/2) and 2.5 g of yellow powder was obtained. The obtained powder was identified to be Compound b by the measurements in accordance with NMR, IR and FD-MS (the yield: 58%, in $^1H_{NMR}$ (90 Hz): δ 7.0~7.4 ppm (40H, m), δ 2.34 ppm (6H,s)). The NMR chart of Compound b is shown in FIG. 2.

The chemical reactions to obtain Compound b are shown in the following:

Compound b

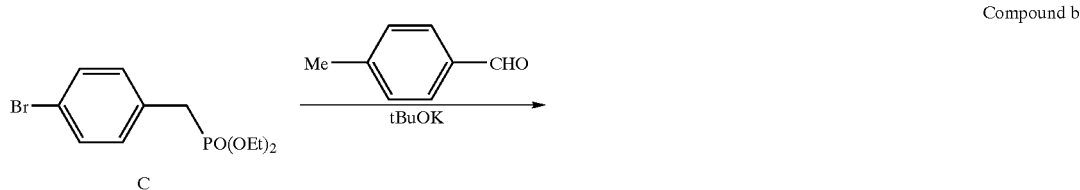

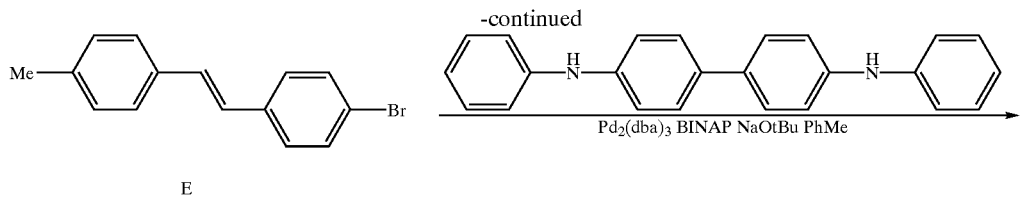

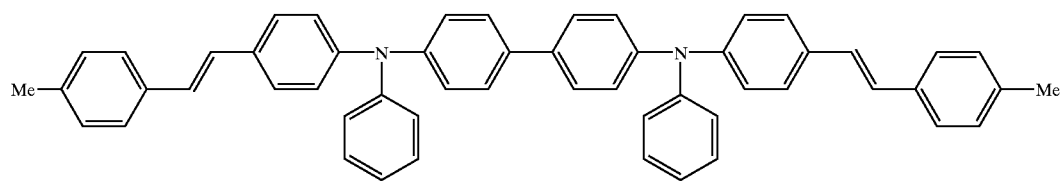

E

Synthesis Example 26 (Compound c)

Synthesis of Compound c

In a 200 ml three-necked flask equipped with a condenser, 4 g (15 mmole) of Intermediate Compound B, 1.7 g (6 mmole) of 1,4-dibromonaphthalene, 0.16 g (3% by mole) of tris(dibenzylideneacetone)dipalladium, 0.22 g (6% by mole) of (S)-BINAP, 1.4 g (15 mmole) of sodium t-butoxide and 50 ml of dry toluene were placed under an argon stream. The resulting mixture was stirred over night under heating at 100° C. After the reaction was completed, precipitated crystals were separated by filtration, washed with methanol and dried by heating at 60° C. for one night. The obtained crude crystals were purified in accordance with the column chromatography (silica gel, hexaneltoluene=8/2) and 2.0 g of yellow powder was obtained. The obtained powder was identified to be Compound c by the measurements in accordance with NMR, IR and FD-MS (the yield: 50%, in $^1H_{NMR}$ (90 Hz): δ 7.0~7.4 ppm (68H, m)).

The chemical reaction to obtain Compound c is shown in the following:

Synthesis Example 27 (Compound d)

Synthesis of Compound d

In a 200 ml three-necked flask equipped with a condenser, 4 g (15 mmole) of Intermediate Compound B, 2 g (6 mmole) of 9,10-dibromoanthracene, 0.16 g (3% by mole) of tris (dibenzylideneacetone)dipalladium, 0.07 g (6% by mole) of tri-t-butylphosphine, 1.4 g (15 mmole) of sodium t-butoxide and 50 ml of dry toluene were placed under an argon stream. The resulting mixture was stirred overnight under heating at 100° C. After the reaction was completed, precipitated crystals were separated by filtration, washed with methanol and dried by heating at 60° C. for one night. The obtained crude crystals were purified in accordance with the column chromatography (silica gel, hexane/toluene=8/2) and 1.9 g of yellow powder was obtained. The obtained powder was identified to be Compound d by the measurements in accordance with NMR, IR and FD-MS (the yield: 44%, in $^1H_{NMR}$ (90 Hz): δ 7.0~7.4 ppm (40H, m)).

The chemical reaction to obtain Compound d is shown in the following:

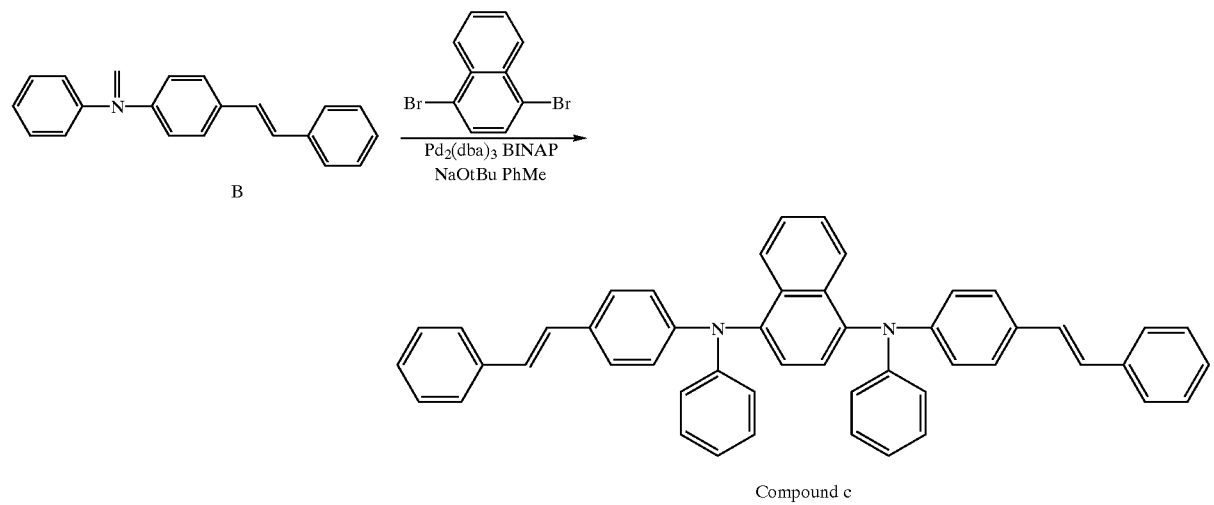

Compound c

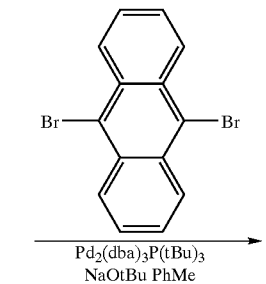
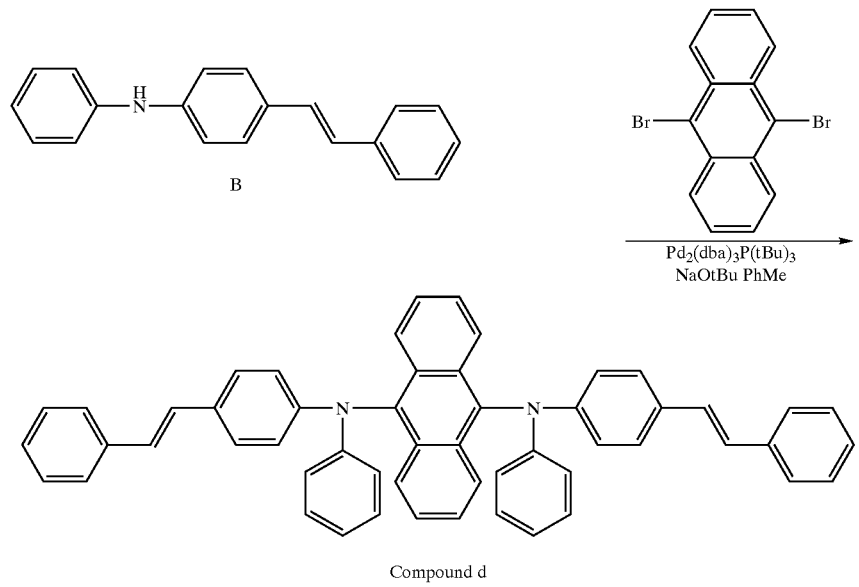

Compound d

Synthesis Example 28 (Compound e)

Synthesis of Intermediate Compound E

In a 300 ml three-necked flask, 10.4 g (50 mmole) of trans-4-stilbenealdehyde, 15.4 g (50 mmole) of Intermediate Compound C and 100 ml of dimethylsulfoxide were placed under an argon stream. To this was added 6.7 g (60 mmole) of potassium t-butoxide in small portions and the resulting mixture was stirred overnight at the room temperature. After the reaction was completed, the reaction liquid was poured into 200 ml of water and extracted with ethyl acetate. The extract was dried with magnesium sulfate and concentrated in vacuo using a rotary evaporator. The obtained crystals were washed with 100 ml of methanol and 12.5 g (the yield: 69%) of Intermediate Compound F was obtained.

Synthesis of Compound e

Figure 3:
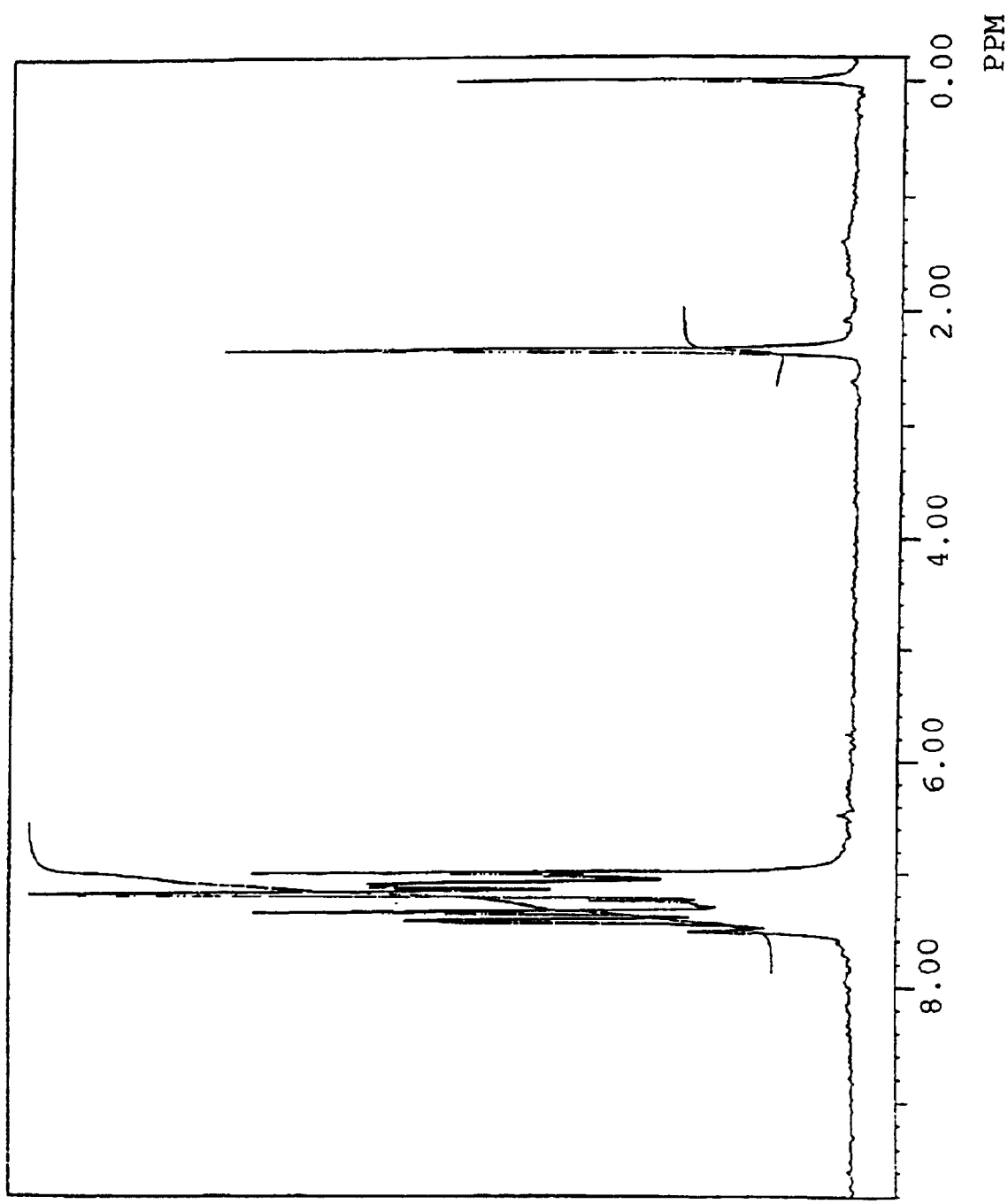
FIG. 3 shows a $^1H_{NMR}$ chart of compound e synthesized in accordance with the process of the present invention.

In a 200 ml three-necked flask equipped with a condenser, 5.4 g (15 mmole) of Intermediate Compound F, 2 g (6 mmole) of N,N'-diphenylbenzidine, 0.16 g (3% by mole) of tris(dibenzylideneacetone)dipalladium, 0.11 g (6% by mole) of tri-o-toluylphosphine, 1.4 g (15 mmole) of sodium t-butoxide and 50 ml of dry toluene were placed under an argon stream. The resulting mixture was stirred overnight under heating at 100° C. After the reaction was completed, precipitated crystals were separated by filtration, washed with methanol and dried by heating at 60° C. for one night. The obtained crude crystals were purified in accordance with the column chromatography (silica gel, hexane/toluene=6/4) and 1.0 g of yellow powder was obtained. The obtained powder was identified to be Compound e by the measurements in accordance with NMR, IR and FD-MS (the yield: 19%, in $^1H_{NMR}$ (90 Hz): δ 7.0~7.5 ppm (52H, m)). The NMR chart of Compound e is shown in FIG. 3.

The chemical reactions to obtain Compound e are shown in the following:

-continued

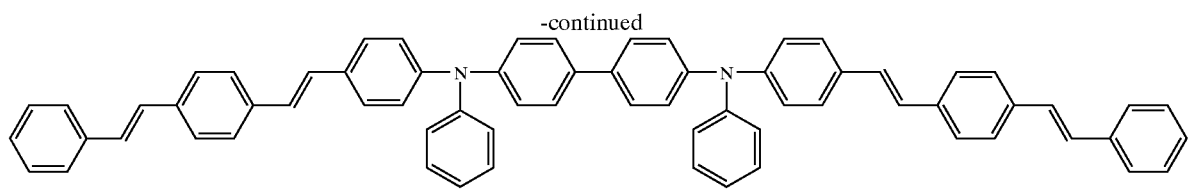

Synthesis of Compound f

In a 200 ml three-necked flask equipped with a condenser, 7.8 g (30 mmole) of Intermediate Compound A, 1.7 g (6 mmole) of 4,4'-diaminostilbene carbon dioxide, 0.16 g (3% by mole) of tris(dibenzylideneacetone)dipalladium, 0.22 g (6% by mole) of (S)-BINAP, 9.6 g (0.1 mole) of sodium t-butoxide and 50 ml of dry toluene were placed under an argon stream. The resulting mixture was stirred overnight under heating at 100° C. After the reaction was completed, precipitated crystals were separated by filtration, washed with methanol and dried by heating at 60° C. for one night. The obtained crude crystals were purified in accordance with the column chromatography (silica gel, hexane/toluene=6/4) and 2.0 g of yellow powder was obtained. The obtained powder was identified to be Compound f by the measurements in accordance with NMR, IR and FD-MS (the yield: 36%, in $^1H_{NMR}$ (90 Hz): δ 7.0~7.5 ppm (54H, m)).

The chemical reaction to obtain Compound f is shown in the following:

derivative and Compound a described above were simultaneously vapor deposited and a layer having a content of Compound a of 2% by weight and a thickness of 40 nm was formed. Compound a works as a fluorescent dopant or the light emitting center. On the layer formed above, Alq described above was vapor deposited as the electron injecting material and a layer having a thickness of 20 nm was formed. After lithium fluoride was vapor deposited and a layer having a thickness of 0.5 nm was formed, aluminum was vapor deposited and a layer having a thickness of 100 nm was formed. Thus, an electrode was formed and an organic EL device was obtained. The layers were vapor deposited in a vacuum of $10^{-6}$ Torr while the substrate was kept at the room temperature. The device exhibited a luminance of emitted light of 100 (cd/m$^2$) and an efficiency of light emission of 2.1 (lm/W) under application of a direct current voltage of 6 V. The color coordinate was (0.146, 0.140) and blue light of a high purity could be emitted. When the organic EL device was driven by a constant electric current at an initial luminance of emitted light of 200 (cd/m$^2$), the half life time was as long as 2,000 hours. The properties of light emission are shown in Table 5.

The energy gap of Compound a was 2.78 eV and the energy gap of DPVBi was 3.0 eV.

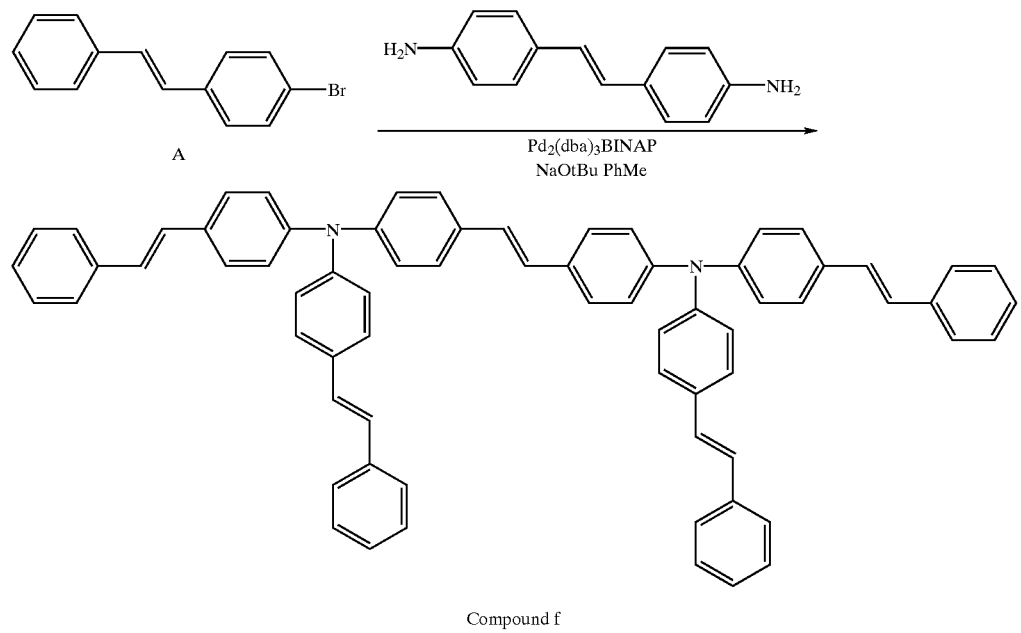

Compound f

EXAMPLE 63

On a cleaned glass plate having an ITO electrode, TPD74 described above was vacuum vapor deposited as the hole injecting material and a layer having a thickness of 60 nm was formed.

Then, NPD described above was vacuum vapor deposited as the hole transporting material and a layer having a thickness of 20 nm was formed.

Subsequently, as the light emitting materials, 4,4'-bis(2, 2-diphenylvinyl)biphenyl (DPVBi) which is a stilbene

EXAMPLE 64

An organic EL device was prepared in accordance with the same procedures as those conducted in Example 63 except that Compound b was used as the dopant or the light emitting center. The device exhibited a luminance of emitted light of 110 (cd/m$^2$) and an efficiency of light emission of 1.3

(lm/W) under application of a direct current voltage of 6 V. The color coordinate was (0.152, 0.163) and blue light of a high purity could be emitted. When the organic EL device was driven by a constant electric current at an initial luminance of emitted light of 200 (cd/m$^2$), the half life time was as long as 1,500 hours. The properties of light emission are shown in Table 5.

The energy gap of Compound b was 2.90 eV and the energy gap of DPVBi was 3.0 eV.

EXAMPLE 65

An organic EL device was prepared in accordance with the same procedures as those conducted in Example 63 except that Compound c was used as the dopant or the light emitting center. The device exhibited a luminance of emitted light of 130 (cd/m$^2$) and an efficiency of light emission of 2.1 (lm/W) under application of a direct current voltage of 6 V. The color coordinate was (0.162, 0.181) and blue light of a high purity could be emitted. When the organic EL device was driven by a constant electric current at an initial luminance of emitted light of 200 (cd/m$^2$), the half life time was as long as 2,800 hours. The properties of light emission are shown in Table 5.

The energy gap of Compound b was 2.83 eV and the energy gap of DPVBi was 3.0 eV.

EXAMPLE 66

An organic EL device was prepared in accordance with the same procedures as those conducted in Example 63 except that Compound d was used as the dopant or the light emitting center. The device exhibited a luminance of emitted light of 300 (cd/m$^2$) and an efficiency of light emission of 4.6 (lm/W) under application of a direct current voltage of 6 V. Light of green color could be emitted with a high efficiency. When the organic EL device was driven by a constant electric current at an initial luminance of emitted light of 200 (cd/m$^2$), the half life time was as long as 3,400 hours. The properties of light emission are shown in Table 5.

The energy gap of Compound d was 2.78 eV and the energy gap of DPVBi was 3.0 eV.

Comparative Example 9

An organic EL device was prepared in accordance with the same procedures as those conducted in Example 63 except that the following compound (TPD):

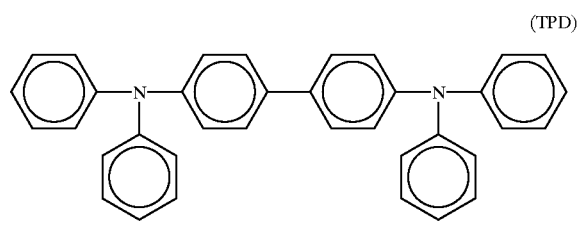

(TPD)

was used as the dopant or the light emitting center. The device exhibited a luminance of emitted light of 60 (cd/m$^2$) and an efficiency of light emission of 0.7 (lm/W) under application of a direct current voltage of 5 V. Sufficient properties could not be obtained. TPD did not work as the light emitting center and light emitted from DPVTP was obtained. When the organic EL device was driven by a constant electric current at an initial luminance of emitted light of 200 (cd/m$^2$), the half life time was as short as 100 hours. The properties of light emission are shown in Table 5.

The energy gap of TPD was 3.10 eV and the energy gap of DPVBi was 3.0 eV.

Comparative Example 10

An organic EL device was prepared in accordance with the same procedures as those conducted in Example 63 except that Compound a described above was used as the dopant or the light emitting material and the compound Alq was used as the light emitting material. The device exhibited a luminance of emitted light of 210 (cd/m$^2$) and an efficiency of light emission of 1.3 (lm/W) under application of a direct current voltage of 6 V. However, light of pink color from Alq alone was obtained. When the organic EL device was driven by a constant electric current at an initial luminance of emitted light of 200 (cd/m$^2$), the half life time was as short as 200 hours. The properties of light emission are shown in Table 5. Compound a did not work as the light emitting center.

The energy gap of Compound a was 2.95 eV and the energy gap of Alq was 2.7 eV.

Comparative Example 11

An organic EL device was prepared in accordance with the same procedures as those conducted in Example 63 except that no dopant or light emitting material was used and Compound c described above was used as the single light emitting material. The device exhibited luminance of emitted light of 40 (cd/m$^2$) and an efficiency of light emission of 0.9 (lm/W) under application of a direct current voltage of 6 V. Sufficient properties could not be obtained. When the organic EL device was driven by a constant electric current at an initial luminance of emitted light of 200 (cd/m$^2$), the half life time was as short as 180 hours. The properties of light emission are shown in Table 5.

The properties of light emission obtained above are shown in Table 5.

TABLE 4

| | Dopant or light emitting center | Light emitting material | Applied voltage (V) | Luminance of emitted light (cd/m$^2$) | Efficiency of light emission (lm/W) | Color of emitted light | Half life time (hour) |
|---|---|---|---|---|---|---|---|
| Example | | | | | | | |
| 63 | Compound a | DPVBi | 6 | 100 | 2.1 | blue | 2000 |
| 64 | Compound b | DPVBi | 6 | 110 | 1.3 | blue | 1500 |
| 65 | Compound c | DPVBi | 6 | 130 | 2.1 | blue | 2800 |
| 66 | Compound d | DPVBi | 6 | 300 | 4.6 | green | 3400 |
| Comparative Example | | | | | | | |
| 9 | TPD | DPVBi | 5 | 60 | 0.7 | blue | 100 |
| 10 | Compound a | Alq | 6 | 210 | 1.3 | green | 200 |
| 11 | none | Compound c | 6 | 40 | 0.9 | blue | 180 |

As shown in Table 5, the organic EL devices of Examples 63 to 66 in which a small amount (1 to 20% by weight) of a compound represented by general formula [1] was added to the host material as the dopant or the light emitting center exhibited higher efficiencies of light emission and much longer lives in comparison with the organic EL devices of Comparative Examples 9 to 11.

Industrial Applicability

The organic EL devices of the present invention in which the materials for organic EL devices represented by general formulae [1], [3] to [6] and [9] to [10] described above are used as the light emitting material, the hole injecting material, the hole transporting material or the doping material exhibit luminances of light emission sufficient for practical use and high efficiencies of light emission under application of a low voltage, have long lives because the decrease in the properties after use for a long time is suppressed and show no deterioration in the properties in the environment of high temperatures due to excellent heat resistance.

The organic EL devices described above in which the materials for organic EL devices represented by general formulae [7] and [8] are used as the light emitting material, the hole injecting material, the hole transporting material or the doping material exhibit, in the region of yellow color and orange to red color, luminances of light emission sufficient for practical use and high efficiencies of light emission under application of a low voltage and have long life times because the decrease in the properties after use for a long time is suppressed.

The organic EL devices in which the material for organic EL devices comprising the compound represented by general formula [11] of the present invention or the novel compound represented by general formula [11'] of the present invention is used as the dopant or the light emitting center exhibit luminances of emitted light sufficient for practical use under application of a low voltage and high efficiencies of light emission and have long lives because the decrease in the properties after use for a long time is suppressed.

By producing materials for organic EL devices in accordance with the process of the present invention, materials for organic EL devices exhibiting a high efficiency of light emission, having a long life, showing high activity and containing little impurities can be produced in a high yield.

What is claimed is:

1. A material for organic electroluminescence devices represented by formula [19]:

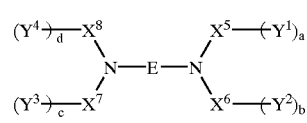

wherein

E represents a divalent group comprising an anthracene nucleus which is substituted with at least two aryl groups, $X^5$ to $X^8$ each independently represent a substituted or unsubstituted arylene group having 6 to 20 carbon atoms, $X^5$ and $X^6$ may be bonded to each other, $X^7$ and $X^8$ may be bonded to each other, $Y^1$ to $Y^4$ each independently represent an organic group represented by formula [2]:

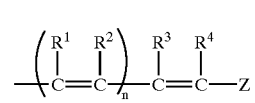

wherein $R^1$ to $R^4$ each independently represent hydrogen atom, a substituted or unsubstituted alkyl group having 1 to 20 carbon atoms, a substituted or unsubstituted aryl group having 6 to 20 carbon atoms, cyano group or form a triple bond by a linkage of $R^1$ and $R^2$ or $R^3$ and $R^4$, Z represents a substituted or unsubstituted aryl group having 6 to 20 carbon atoms, and n represents 0 or 1, and a to d each represent an integer of 0 to 2.

2. A material for organic electroluminescence devices represented by formula [9]:

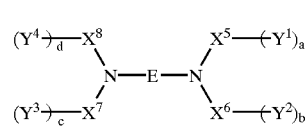

wherein

E represents a group represented by the formula:

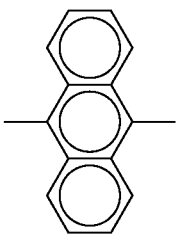

$X^5$ to $X^8$ each independently represent a substituted or unsubstituted arylene group having 6 to 20 carbon atoms, $X^5$ and $X^6$ may be bonded to each other, $X^7$ and $X^8$ may be bonded to each other, at least two of $X^5$ to $X^8$ contain a substituted or unsubstituted group represented by the formula:

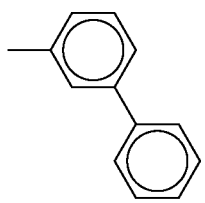

$Y^1$ to $Y^4$ each independently represent an organic group represented by formula [2]:

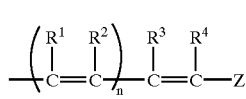

[2]

wherein $R^1$ to $R^4$ each independently represent hydrogen atom, a substituted or unsubstituted alkyl group having 1 to 20 carbon atoms, a substituted or unsubstituted aryl group having 6 to 20 carbon atoms, cyano group or form a triple bond by a linkage of $R^1$ and $R^2$ or $R^3$ and $R^4$, Z represents a substituted or unsubstituted aryl group having 6 to 20 carbon atoms, and n represents 0 or 1, and a to d each represent an integer of 0 to 2.

3. The material for organic electroluminescence devices according to claim 1 or 2, which is a light emitting material for organic electroluminescence devices.

4. An organic electroluminescence device which comprises a light emitting layer or a plurality of thin films of organic compounds comprising a light emitting layer disposed between a pair of electrodes, wherein the light emitting layer or at least one of the thin films of organic compounds is a layer comprising a material for organic electroluminescence devices described in claim 1 or 2.

5. An organic electroluminescence device which comprises a light emitting layer or a plurality of thin films of organic compounds comprising a light emitting layer disposed between a pair of electrodes, wherein a layer comprising a material for organic electroluminescence devices described in claim 1 or 2 as at least one material selected from a group consisting of a hole injecting material, a hole transporting material and a doping material is disposed between the pair of electrodes.

6. An organic electroluminescence device which comprises a light emitting layer or a plurality of thin films of organic compounds comprising a light emitting layer disposed between a pair of electrodes, wherein the light emitting layer comprises 0.1 to 20% by weight of a material for organic electroluminescence devices described in claim 1 or 2.

7. An organic electroluminescence device which comprises a light emitting layer or a plurality of thin films of organic compounds comprising a light emitting layer disposed between a pair of electrodes, wherein one or more materials selected from a group consisting of a hole injecting material, a hole transporting material and a doping material each independently comprise 0.1 to 20% by weight of a material for organic electroluminescence devices described in claim 1 or 2.

8. An organic electroluminescence device which comprises a light emitting layer or a plurality of thin films of organic compounds comprising a light emitting layer disposed between a pair of electrodes, wherein the light emitting layer is a layer comprising a stilbene derivative and a material for organic electroluminescence devices described in claim 1 or 2.

9. The material for organic electroluminescence devices according to claim 1, wherein E represents a divalent group comprising an anthracene nucleus substituted with at least two aryl groups at the positions 9 and 10 or 2 and 6 of the anthracene nucleus.

* * * * *